United States Patent
Haning et al.

(10) Patent No.: US 6,555,580 B2
(45) Date of Patent: Apr. 29, 2003

(54) AMINO- AND AMIDO-DIPHENYL ETHERS

(75) Inventors: Helmut Haning, Wuppertal (DE); Josef Pernerstorfer, Wuppertal (DE); Gunter Schmidt, Wuppertal (DE); Michael Woltering, Wuppertal (DE); Hilmar Bischoff, Wuppertal (DE); Verena Vöhringer, Wuppertal (DE); Axel Kretschmer, Wuppertal (DE); Christiane Faeste, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/918,741

(22) Filed: Jul. 31, 2001

(65) Prior Publication Data

US 2003/0027862 A1 Feb. 6, 2003

(30) Foreign Application Priority Data

Aug. 4, 2000 (DE) .......................... 100 38 007

(51) Int. Cl.[7] .................. C07C 233/01; A61K 31/24
(52) U.S. Cl. .................. 514/563; 564/123; 564/160
(58) Field of Search ................ 564/123, 160; 514/563

(56) References Cited

FOREIGN PATENT DOCUMENTS

| EP | 0188351 | 7/1986 |
|---|---|---|
| EP | 0580550 | 1/1994 |
| WO | 9900353 | 1/1999 |
| WO | 9926966 | 6/1999 |
| WO | 0051971 | 9/2000 |
| WO | 0058279 | 10/2000 |

OTHER PUBLICATIONS

Yokoyama, N., Walker, G. N., Main, A. J., Stanton, J. L., Morrissey, M. M., Boehm, C., Engle, A., Neubert, A. D., Wasvary, J. M., Stephan, Z. F., and Steele, R. E., "Synthesis and Structure–Activity Relationships of Oxamic Acid and Acetic Acid Derivatives Related to L–Thyronine", J. Med. Chem., 38: 695–707 (1995).

Bruno, J. G., Chang, M. N., Choi–Sledeski, Y. M., Green, D. M., McGarry, D. G., Regan, J. R., Volz, F. A., "Synthesis of Functionalized Aromatic Oligomers from a Versatile Diphenylmethane Template", J. Org. Chem., 62: 5174–5190 (1997).

James, I. W., Tetrahedron, 55: 4855–4946 (1999).

Nicolaou, K. C., Xiao, X.–Y., Parandoosh, Z., Senyei, A., Nova, M. P., "Radiofrequency Encoded Combinatorial Chemistry", Angew. Chem. Int. Ed. Engl., 34(20): 2289–2291 (1995).

Bergmann, M., Dangschat, P., Chem. Berg., 52: 371–387 (1919).

*Primary Examiner*—Joseph K. McKane
*Assistant Examiner*—Kamal Saeed
(74) *Attorney, Agent, or Firm*—Jerrie L. Chiu

(57) ABSTRACT

The invention relates to novel amino- and amido-diphenyl ethers, processes for their preparation and their use in pharmaceuticals, in particular for the indications of arteriosclerosis and hypercholesterolaemia.

8 Claims, No Drawings

AMINO- AND AMIDO-DIPHENYL ETHERS

The invention relates to novel amino- and amido-diphenyl ethers, processes for their preparation and their use in pharmaceuticals, in particular for the indications of arteriosclerosis and hypercholesterolaemia.

European Application 580 550 A (Ciba Geigy; 1994) describes oxamic acid derivatives having cholesterol-lowering properties in mammals. This application describes an in vitro test based on the binding to thyroid hormone cell receptors (so-called $T_3$ nuclear receptors). The pharmacological property which is stressed is the reduction in plasma cholesterol, in particular LDL cholesterol. Cholesterol-lowering effects are also described in the European Application EP-A-188 351 (SKF; 1986) for certain diphenyl ethers with thyroid hormone-like effects.

It has now been found that the compounds of the general formula (I)

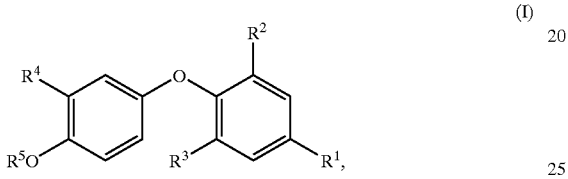

(I)

in which
R$^1$ represents nitro, amino, acetamido or represents a group of the formula —NH—CO—CO—A or —NH—CH$_2$—CO—A, in which
  A represents hydroxyl or (C$_1$–C$_4$)-alkoxy,
R$^2$ and R$^3$ are identical or different and denote halogen, C$_1$–C$_4$-alkyl or trifluoromethyl,
R$^4$ represents a group of the formula

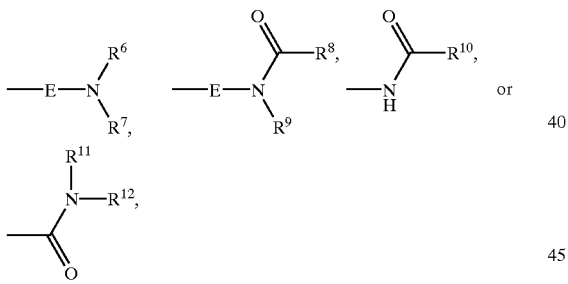

in which
E represents straight-chain or branched (C$_1$–C$_4$)-alkyl,
R$^6$ and R$^7$ are identical or different and, independently of one another, represent straight-chain or branched (C$_1$–C$_{10}$)-alkyl which can be substituted one or more times, identically or differently, by (C$_3$–C$_8$)-cycloalkyl, (C$_1$–C$_6$)-alkoxy, amino, mono- or di-(C$_1$–C$_6$)-alkyl amino, (C$_1$–C$_4$)-alkoxycarbonyl amino, aminocarbonyl, (C$_1$–C$_6$)-alkoxycarbonyl, or by (C$_6$–C$_{10}$)-aryl or 5 to 6-membered saturated or aromatic heterocyclyl with up to three heteroatoms from the series N, O and/or S, where aryl and heterocyclyl in turn are optionally substituted one or more times, identically or differently, by (C$_1$–C$_4$)-alkyl, aminocarbonyl, (C$_1$–C$_4$)-alkanoylamino or halogen,
  represent (C$_6$–C$_{10}$)-aryl or (C$_3$–C$_8$)-cycloalkyl, each of which can be substituted by (C$_1$–C$_4$)-alkoxy, or
  represent a 4- to 8-membered saturated heterocycle with up to two heteroatoms from the series N, O and/or S, which can be substituted one or more times, identically or differently, by (C$_1$–C$_4$)-alkoxycarbonyl, oxo or (C$_1$–C$_4$)-alkyl, or
R$^6$ and R$^7$ form, together with the nitrogen atom to which they are bonded, a 4- to 7-membered saturated heterocycle which optionally contains up to two other heteroatoms from the series N, O and/or S,
R$^8$ represents straight-chain or branched (C$_1$–C$_{10}$)-alkyl which can be substituted by (C$_3$–C$_8$)-cycloalkyl, phenyl or phenoxy, or represents (C$_3$–C$_8$)-cycloalkyl, (C$_6$–C$_{10}$)-aryl, biphenylyl or (C$_1$–C$_6$)-alkoxy,
R$^9$ represents straight-chain or branched (C$_1$–C$_8$)-alkyl whose carbon chain can be interrupted by —O— and which can be substituted by (C$_3$–C$_8$)-cycloalkyl or phenyl, or represents (C$_3$–C$_8$)-cycloalkyl, (C$_2$–C$_6$)-alkenyl, phenyl or pyridyl,
  where the aromatic ring systems mentioned both in R$^8$ and in R$^9$ can, in each case independently of one another, in turn be substituted by trifluoromethyl, halogen, (C$_1$–C$_4$)-alkoxy, (C$_1$–C$_4$)-alkyl or amino, or
R$^8$ and R$^9$ form, together with the nitrogen atom and the carbonyl group to which they are bonded, a 4- to 7-membered saturated heterocycle which optionally contains up to two other heteroatoms from the series N, O and/or S,
R$^{10}$ represents straight-chain or branched (C$_1$–C$_{15}$)-alkyl which can be substituted by (C$_3$–C$_8$)-cycloalkyl, (C$_1$–C$_4$)-alkoxy, phenyl, phenoxy or benzyloxy, where the said aromatic radicals can in turn each be substituted up to three times, identically or differently, by halogen, (C$_1$–C$_6$)-alkyl or (C$_1$–C$_4$)-alkoxy,
  represents (C$_3$–C$_8$)-cycloalkyl which can be substituted by (C$_1$–C$_4$)-alkoxy or phenyl,
  represents (C$_6$–C$_{10}$)-aryl which can be substituted up to three times, identically or differently, by (C$_1$–C$_6$)-alkyl, (C$_1$–C$_6$)-alkoxy, halogen, cyano, amino, trifluoromethyl or phenyl, or
  represents a 5- to 6-membered saturated or aromatic, optionally benzo-fused heterocycle with up to two heteroatoms from the series N, O and/or S, or
  denotes a group of the formula —OR$^{13}$ or NR$^{14}$R$^{15}$,
  in which
    R$^{13}$ represents straight-chain or b ranched (C$_1$–C$_6$)-alkyl, and
    R$^{14}$ and R$^{15}$ are identical or different and, independently of one another,
      represent hydrogen, straight-chain or branched (C$_1$–C$_{12}$)-alkyl, which can be substituted by aminocarbonyl, a group of the formula —NR$^{16}$R$^{17}$, 5- to 6-membered heteroaryl which contains up to 3 heteroatoms selected from the series N, O and/or S or can be substituted by phenyl, where phenyl is optionally substituted up to twice, identically or differently, by halogen, (C$_1$–C$_4$)-alkyl, trifluoromethyl or (C$_1$–C$_4$)-alkoxy,
      represent (C$_3$–C$_8$)-cycloalkyl which can be substituted by (C$_1$–C$_4$)-alkyl,
      represent (C$_6$–C$_{10}$)-aryl which can be substituted up to three times, identically or differently, by halogen, (C$_1$–C$_4$)-alkyl, trifluoromethyl, (C$_1$–C$_4$)-alkoxy, amino, phenyl or phenoxy, or
      represent a 5- to 7-membered, saturated or unsaturated heterocycle which contains one or two nitrogen atoms and which can be bonded via a carbon or nitrogen atom and is optionally substituted by $(C_1-C_4)$-alkyl or an oxo group, where $R^{16}$ and $R^{17}$ are identical or different and, independently of one another, represent hydrogen, $(C_1-C_6)$-alkyl, phenyl or $(C_6-C_{10})$-arylsulphonyl, or form, together with the nitrogen atom to which they are bonded, a 3- to 7-membered saturated heterocycle which optionally contains up to two other heteroatoms from the series N, O and/or S, or $R^{14}$ and $R^{15}$ form, together with the nitrogen atom to which they are bonded, a 4- to 7-membered saturated heterocycle which can contain up to two other heteroatoms from the series N, O and/or S and be substituted by amino, $(C_1-C_6)$-alkyl, $(C_1-C_4)$-alkanoyl, aminocarbonyl, $(C_1-C_4)$-alkoxycarbonyl, $(C_1-C_4)$-alkoxycarbonylamino, phenyl or pyridyl, $R^{11}$ and $R^{12}$ are identical or different and, independently of one another, represent hydrogen, straight-chain or branched $(C_1-C_6)$-alkyl, which can be substituted one or more times, identically or differently, by mono-$(C_1-C_6)$-alkylamino, di-$(C_1-C_6)$-alkylamino, $(C_1-C_4)$-alkoxy, $(C_1-C_6)$-alkoxycarbonyl, carboxyl, pyridyl or $(C_6-C_{10})$-aryl, where the latter in turn is optionally substituted by halogen, trifluoromethyl, $(C_1-C_6)$-alkyl or $(C_1-C_6)$-alkoxy, represent $(C_3-C_8)$-cycloalkyl or represent a 5- to 7-membered heterocycle which contains one to two nitrogen atoms and which can be bonded via a carbon or nitrogen atom, where cycloalkyl and heterocycle are optionally substituted by $(C_1-C_4)$-alkyl, or $R^{11}$ and $R^{12}$ form, together with the nitrogen atom to which they are bonded, a 5- to 7-membered saturated, optionally benzo-fused heterocycle which can contain up to two other heteroatoms from the series N, O and/or S and be substituted by amino, $(C_1-C_6)$-alkyl, $(C_1-C_4)$-alkoxycarbonyl, $(C_1-C_4)$-alkoxy-carbonylamino or phenyl, and $R^5$ denotes hydrogen, $(C_1-C_4)$-alkyl or $(C_1-C_4)$-alkanoyl, and the respective salts and hydrates thereof show a pharmacological effect and can be used as pharmaceuticals or for producing pharmaceutical formulations.

Heteroaryl is intended to mean for the purposes of the invention in general a 5- to 8-membered aromatic, optionally benzo-fused heterocycle with up to 4 heteroatoms from the series S, N and/or O. Examples which may be mentioned are: pyridyl, thienyl, thiazolyl, oxazolyl, imidazolyl, triazolyl, tetrazolyl.

Heterocycles are intended to mean for the purposes of the invention generally a 5- to 8-membered, saturated, partially unsaturated or aromatic, optionally benzo-fused heterocycle with up to 4 heteroatoms from the series S, N and/or O, that is to say a heterocycle which may contain one or more double bonds and which is linked via a ring carbon atom or a ring nitrogen atom. Examples which may be mentioned are: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin-3-yl, 1,2-dihydropyridin-1-yl, 1,4-dihydropyridin-1-yl, piperazin-1-yl, morpholin-1-yl, azepin-1-yl, 1,4-diazepin-1-yl, furan-2-yl, furan-3-yl, pyrrol-1-yl, pyrrol-2-yl, pyrrol-3-yl, pyrimidyl, pyrazinyl, pyrimidinonyl, pyridazinonyl.

Those in this list which are preferred are: pyrimidyl, pyridazinyl, pyrimidinonyl, pyridazinonyl.

$(C_1-C_{15})$-Alkyl, $(C_1-C_{12})$-alkyl, $(C_1-C_{10})$-alkyl, $(C_1-C_8)$-alkyl, $(C_1-C_6)$-alkyl, $(C_1-C_4)$-alkyl and $(C_1-C_3)$-alkyl represent for the purposes of the invention a straight-chain or branched alkyl radical respectively with 1 to 15, 1 to 12, 1 to 10, 1 to 8, 1 to 6, 1 to 4 and 1 to 3 carbon atoms. A straight-chain or branched alkyl radical with 1 to 3 carbon atoms is preferred. Preferred examples which may be mentioned are: methyl, ethyl, n-propyl, isopropyl, n-, i-, s- or t-butyl, n-pentyl and n-hexyl.

$(C_6-C_{10})$-Aryl represents for the purposes of the invention an aromatic radical with 6 to 10 carbon atoms. Preferred aryl radicals are phenyl and naphthyl.

$(C_3-C_8)$-Cycloalkyl, $(C_3-C_7)$-cycloalkyl and $(C_3-C_6)$-cycloalkyl represent for the purposes of the invention a cycloalkyl group respectively with 3 to 8, 3 to 7 and 3 to 6 carbon atoms. Those which may be mentioned as preferred are: cyclopropyl, cyclobutyl, cyclopentyl, cyclohexyl and cycloheptyl.

$(C_2-C_6)$-Alkenyl represents for the purposes of the invention straight-chain or branched alkenyl with 1 to 3 double bonds and 2 to 6 carbon atoms, preferably 1 or 2 double bonds and 2 to 4 carbon atoms, particularly preferably 1 double bond and 2 or 3 carbon atoms. Examples are: vinyl, allyl, prop-1-en-1-yl, isopropenyl, but-1-enyls, but-2-enyls, buta-1,2-dienyls, buta-1,3-dienyls.

$(C_1-C_6)$-Monoalkylamino represents a straight-chain or branched alkylamino radical with 1 to 6 carbon atoms. A straight-chain or branched alkylamino radical with 1 to 4 carbon atoms is preferred. Examples which may be mentioned are: methylamino, ethylamino, n-propylamino, isopropylamino, tert-butylamino, n-pentylamino and n-hexylamino. A straight-chain or branched alkylamino radical with 1 to 3 carbon atoms is particularly preferred.

$(C_1-C_6)$-Dialkylamino represents a straight-chain or branched dialkylamino radical where the alkyl radicals can be identical or different and each contains 1 to 6 carbon atoms. A straight-chain or branched dialkylamino radical where each alkyl radical contains 1 to 4 carbon atoms is preferred. Examples which may be mentioned are: dimethylamino, diethylamino, di-n-propylamino, diisopropylamino, di-t-butylamino, di-n-pentylamino, di-n-hexylamino, ethylmethylamino, isopropylmethylamino, n-butylethylamino, n-hexyl-i-pentylamino. A straight-chain or branched dialkylamino radical with 1 to 3 carbon atoms is particularly preferred.

$(C_1-C_6)$-Alkoxycarbonylamino represents a straight-chain or branched alkoxycarbonylamino radical with 1 to 6 carbon atoms. A straight-chain or branched alkoxycarbonylamino radical with 1 to 4 carbon atoms is preferred. Examples which may be mentioned are: methoxycarbonylamino, ethoxycarbonylamino, n-propoxycarbonylamino, isopropoxycarbonylamino, tert-butoxycarbonylamino, n-pentoxy-carbonylamino and n-hexoxycarbonylamino. A straight-chain or branched alkoxycarbonylamino radical with 1 to 3 carbon atoms is particularly preferred.

$(C_1-C_6)$-Alkoxycarbonyl represents a straight-chain or branched alkoxycarbonyl radical with 1 to 6 carbon atoms. A straight-chain or branched alkoxycarbonyl radical with 1 to 4 carbon atoms is preferred. Examples which may be mentioned are: methoxycarbonyl, ethoxycarbonyl, n-propoxycarbonyl, isopropoxycarbonyl and tert-butoxycarbonyl. A straight-chain or branched alkoxycarbonyl radical with 1 to 3 carbon atoms is particularly preferred.

($C_1$–$C_6$)-Alkoxy represents for the purposes of the invention a straight-chain or branched alkoxy radical with 1 to 6 carbon atoms. A straight-chain or branched alkoxy radical with 1 to 3 carbon atoms is preferred. Examples which may be mentioned are: methoxy, ethoxy, n-propoxy, isopropoxy, t-butoxy, n-pentoxy and n-hexoxy.

($C_1$–$C_4$)-Alkanoyl represents for the purposes of the invention a straight-chain or branched alkyl radical with 1 to 4 carbon atoms which has a doubly bonded oxygen atom in the 1 position and is linked via the 1 position. Examples which may be mentioned are: formyl, acetyl, propionyl, n-butyryl, i-butyryl.

($C_1$–$C_4$)-Alkanoylamino represents for the purposes of the invention a radical of the formula Alk-CO—NH— in which the group Alk-CO— represents a ($C_1$–$C_4$)-alkanoyl radical as defined above.

Amino represents for the purposes of the invention the $NH_2$ group.

Aminocarbonyl represents for the purposes of the invention the $H_2NCO$— group.

($C_1$–$C_4$)-Alkoxycarbonyl amino represents for the purposes of the invention a radical of the formula AlkO—CO—NH— in which the group AlkO-CO— represents a ($C_1$–$C_4$)-alkoxycarbonyl radical as defined above.

Halogen includes for the purposes of the invention fluorine, chlorine, bromine, and iodine. Fluorine, chlorine or bromine is preferred.

The compounds according to the invention may, depending on the substitution pattern, exist in stereoisomeric forms which either are related as image and mirror image (enantiomers) or are not related as image and mirror image (diastereomers). The invention relates both to the enantiomers or diastereomers and to respective mixtures thereof. The racemic forms can, just like the diastereomers, be separated into the stereoisomerically pure constituents in a known manner.

Certain compounds may furthermore exist in tautomeric forms. This is known to the skilled person, and such compounds are likewise encompassed by the scope of the invention.

The compounds according to the invention may also be in the form of salts. Physiologically acceptable salts are preferred for the purposes of the invention.

Physiologically acceptable salts may be salts of the compounds of the invention with inorganic or organic acids. Preference is given to salts with inorganic acids, such as, for example, hydrochloric acid, bromic acid, phosphoric acid or sulphuric acid, or salts with organic carboxylic or sulphonic acids such as, for example, acetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Physiologically acceptable salts may likewise be salts of the compounds according to the invention with bases, such as, for example, metal or ammonium salts. Preferred examples are alkali metal salts (for example sodium or potassium salts), alkaline earth metal salts (magnesium or calcium salts), and ammonium salts which are derived from ammonia or organic amines such as, for example, ethylamine, di- or triethylamine, ethyldiisopropylamine, ethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylenediamine or 2-phenylethylamine.

The compounds according to the invention may also be in the form of their solvates, in particular in the form of their hydrates.

Preference is given to compounds of the general formula (I) in which $R^1$ represents acetamido or represents a group of the formula —NH—CO—CO—A or —NH—$CH_2$—CO—A, in which
A represents hydroxyl or ($C_1$–$C_4$)-alkoxy, $R^2$ and $R^3$ are identical or different and denote halogen, methyl or trifluoro-methyl, $R^4$ represents a group of the formula

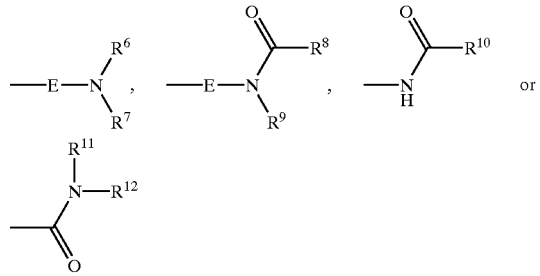

in which

E represents straight-chain or branched ($C_1$–$C_4$)-alkyl, $R^6$ and $R^7$ are identical or different and, independently of one another,
represent straight-chain or branched $C_1$–$C_{10}$-alkyl which can be substituted one or more times, identically or differently, by ($C_3$–$C_8$)-cycloalkyl, ($C_1$–$C_4$)-alkoxy, 5- to 6-membered saturated or aromatic heterocyclyl with up to three heteroatoms from the series N, O and/or S, or by ($C_6$–$C_{10}$)-aryl which in turn is optionally substituted one or more times, identically or differently, by aminocarbonyl, ($C_1$–$C_4$)-alkanoylamino or halogen,
represent ($C_3$–$C_8$)-cycloalkyl which can be substituted by ($C_1$–$C_4$)-alkoxy, or
represent a 4- to 8-membered saturated heterocycle with up to two heteroatoms from the series N, O and/or S which can be substituted one or more times, identically or differently, by ($C_1$–$C_4$)-alkyl, $R^8$ represents straight-chain or branched ($C_1$–$C_8$)-alkyl, ($C_3$–$C_8$)-cycloalkyl, ($C_3$–$C_6$)-cycloalkylmethyl or phenyl, $R^9$ represents straight-chain or branched ($C_1$–$C_8$)-alkyl whose carbon chain can be interrupted by —O— and which can be substituted by phenyl, or ($C_3$–$C_8$)-cycloalkyl or phenyl which can be substituted by halogen, trifluoromethyl or ($C_1$–$C_4$)-alkyl, $R^{10}$ represents straight-chain or branched ($C_1$–$C_{10}$)-alkyl which can be substituted by ($C_3$–$C_8$)-cycloalkyl, ($C_1$–$C_4$)-alkoxy, phenyl or phenoxy, where the said aromatic radicals can in turn each be substituted up to three times, identically or differently, by halogen, ($C_1$–$C_3$)-alkyl or ($C_1$–$C_4$)-alkoxy,
represents ($C_3$–$C_8$)-cycloalkyl or represents phenyl which can be substituted up to three times, identically or differently, by ($C_1$–$C_4$)-alkyl, ($C_1$–$C_4$)-alkoxy, halogen or phenyl, or represents a 5- to 6-membered saturated or aromatic, optionally benzo-fused heterocycle with up to two heteroatoms from the series N, O and/or S, or denotes a group of the formula —$OR^{13}$ or —$NR^{14}R^{15}$, in which $R^{13}$ represents straight-chain or branched ($C_1$–$C_6$)-alkyl, and $R^{14}$ and $R^{15}$ are identical or different and, independently of one another, represent hydrogen or straight-chain or branched ($C_1$–$C_6$)-alkyl which can be substituted by phenyl which in turn is optionally substituted up to twice, identically or differently, by halogen, ($C_1$–$C_4$)-alkyl, trifluoromethyl or ($C_1$–$C_4$)-alkoxy, represent ($C_3$–$C_8$)-cycloalkyl which can be substituted by ($C_1$–$C_4$)-alkyl, or represent phenyl, naphthyl or biphenylyl, $R^{11}$ and $R^{12}$ are identical or different and, independently of one another, represent hydrogen or straight-chain or branched ($C_1$–$C_6$)-alkyl which can be substituted by phenyl which in turn is optionally substituted by halogen, trifluoromethyl, ($C_1$–$C_4$)-alkyl or ($C_1$–$C_4$)-alkoxy, or represent ($C_3$–$C_8$)-cycloalkyl which can be substituted by ($C_1$–$C_4$)-alkyl, and $R^5$ denotes hydrogen or ($C_1$–$C_4$)-alkanoyl, and the respective salts and hydrates thereof.

Particular preference is given to compounds according to the invention of the general formula (I) in which $R^1$ represents a group of the formula —NH—CO—COOH or —NH—$CH_2$—COOH, $R^2$ and $R^3$ are identical or different and denote chlorine, bromine, methyl or trifluoromethyl, $R^4$ represents a group of the formula

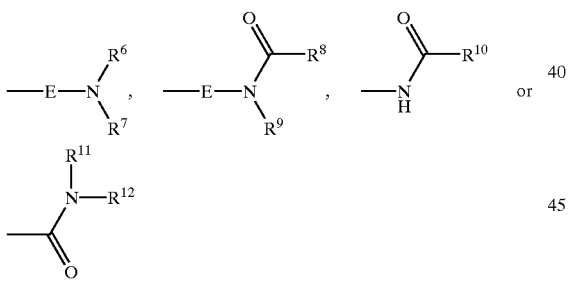

in which $R^6$ and $R^7$ are identical or different and, independently of one another, represent a straight-chain or branched ($C_1$–$C_8$)-alkyl which can be substituted by ($C_5$–$C_8$)-cycloalkyl, pyridyl, furyl, tetrahydrofuryl or one to three times by methoxy or ethoxy, or which is substituted by phenyl which in turn is optionally substituted once to twice, identically or differently, by fluorine, chlorine, aminocarbonyl or acetamido, represent ($C_3$–$C_8$)-cycloalkyl which can be substituted by methoxy or ethoxy, or represent pyrrolidinyl or piperidinyl, each of which can be substituted one or more times by methyl, $R^8$ represents straight-chain ($C_1$–$C_7$)-alkyl, ($C_3$–$C_6$)-cycloalkylmethyl, ($C_3$–$C_6$)-cycloalkyl or phenyl, $R^9$ denotes straight-chain or branched ($C_1$–$C_4$)-alkyl which can be substituted by phenyl, or ($C_3$–$C_6$)-cycloalkyl or phenyl which can be substituted by chlorine or fluorine, $R^{10}$ represents straight-chain or branched ($C_1$–$C_4$)-alkyl which can be substituted by ($C_3$–$C_6$)-cycloalkyl, phenyl or phenoxy, where the said aromatic radicals can in turn each be substituted up to three times, identically or differently, by fluorine, chlorine or ($C_1$–$C_3$)-alkyl, or represents biphenylyl, 2,3-dihydro-1-benzofuranyl, 3,4-dihydro-2H-1-benzopyranyl or 3,4-dihydro-1H-2-benzopyranyl, or represents a group of the formula —$NR^{14}R^{15}$, in which $R^{14}$ denotes hydrogen or straight-chain or branched ($C_1$–$C_3$)-alkyl, and $R^{15}$ represents straight-chain or branched ($C_1$–$C_4$)-alkyl which can be substituted by phenyl which in turn is optionally substituted by methyl, methoxy, trifluoromethyl, fluorine or chlorine, or represents naphthyl, biphenylyl or ($C_3$–$C_6$)-cycloalkyl, $R^{11}$ denotes hydrogen or straight-chain or branched ($C_1$–$C_3$)-alkyl, and $R^{12}$ represents straight-chain or branched ($C_1$–$C_4$)-alkyl which can be substituted by phenyl which in turn is optionally substituted by methyl, methoxy, trifluoromethyl, fluorine or chlorine, or represents cyclopentyl or cyclohexyl, each of which can be substituted by ($C_1$–$C_3$)-alkyl, and $R^5$ denotes ($C_1$–$C_4$)-alkyl or, in particular, hydrogen, and the respective salts and hydrates thereof Very particular preference is given to compounds according to the invention of the general formula (I) in which $R^1$ represents a group of the formula —NH—CO—COOH or —NH—$CH_2$—COOH, $R^2$ and $R^3$ are identical or different and denote chlorine, bromine, methyl or trifluoromethyl, $R^4$ represents a group of the formula

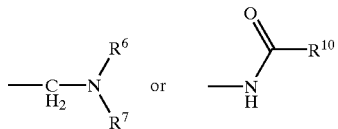

in which $R^6$ and $R^7$ are identical or different and, independently of one another, represent straight-chain or branched ($C_1$–$C_8$)-alkyl which can be substituted by phenyl which in turn is optionally substituted once to twice, identically or differently, by fluorine, chlorine, aminocarbonyl or acetamido, or can be substituted by ($C_5$–$C_8$)-cycloalkyl, pyridyl, furyl, tetrahydrofuryl or once to three times by methoxy or ethoxy, represent ($C_5$–$C_8$)-cycloalkyl which can be substituted by methoxy or ethoxy, or represent pyrrolidinyl or piperidinyl, each of which can be substituted one or more times by methyl, and $R^{10}$ represents straight-chain or branched ($C_1$–$C_4$)-alkyl which can be substituted by ($C_3$–$C_6$)-cycloalkyl, phenyl or phenoxy, where the said aromatic radicals can in turn each be substituted up to three times, identically or differently, by fluorine, chlorine or ($C_1$–$C_3$)-alkyl, or represents biphenylyl, 2,3-dihydro-1-benzofuranyl, 3,4-dihydro-2H-1-benzopyranyl or 3,4-dihydro-1H-2-benzopyranyl, and $R^5$ denotes hydrogen, and the respective salts and hydrates thereof.

Particularly preferred compounds of the general formula (I) are those in which E represents methylene.

Particularly preferred compounds are likewise those in which $R^5$ represents hydrogen.

The radical definitions listed above in general or indicated in preferred ranges apply both to the final products of the formula (I) and correspondingly to the starting materials and intermediates required for the preparation in each case.

The radical definitions specifically indicated in the respective combinations or preferred combinations of radicals are also replaced by radical definitions of other combinations as desired, irrespective of the combinations of radicals indicated in each case.

A process for preparing the compounds according to the invention of the general formula (I) has additionally been found and is characterized in that (A) compounds of the formula (II)

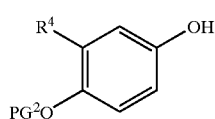

(II)

in which $PG^2$ denotes a hydroxyl protective group or a resin suitable for solid-phase synthesis, and $R^4$ has the meaning indicated above, are reacted in the presence of a base with compounds of the general formula (III)

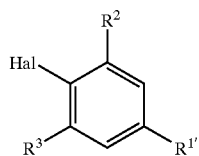

(III)

in which $R^2$ and $R^3$ have the meaning indicated above, and $R^{1'}$ represents a suitable group from the scope of meanings of $R^1$, preferably represents the $NO_2$ group, and Hal represents chlorine or fluorine, to give compounds of the formula (IV)

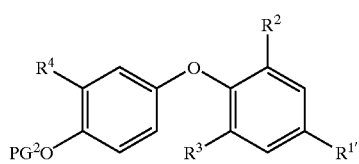

(IV)

in which $R^{1'}$, $R^2$, $R^3$, $R^4$ and $PG^2$ have the meaning indicated above, or (B) compounds of the formula (V)

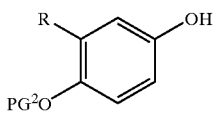

(V)

in which $PG^2$ has the meaning indicated above, and

R represents a suitable precursor of the $R^4$ group, preferably represents CHO, $(C_1-C_6)$-alkoxycarbonyl or nitro, are reacted in the presence of a base with a compound of the formula (III)

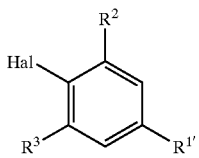

(III)

in which $R^{1'}$, $R^2$, Hal and $R^3$ have the meaning indicated above, to give a compound of the formula (VI)

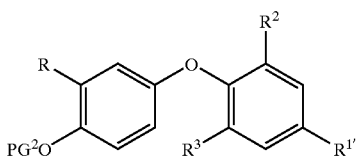

(VI)

in which

R, $R^{1'}$, $R^2$, $R^3$ and $PG^2$ have the meaning given above, and the latter is converted into compounds of the formula (IV) by converting the substituent R in a suitable manner to the substituent $R^4$, and in that finally the protective group $PG^2$ is eliminated from the compound of the formula (IV) and, where appropriate, the substituents are modified or derivatized in a suitable way by standard reactions.

The coupling reactions on compounds of the formulae (II) and (III) or (V) and (III) are normally carried out in a solvent which is inert under the reaction conditions. Examples which may be mentioned are dimethylformamide, dimethylacetamide, N-methylpyrrolidinone, acetonitrile and, in particular, dimethyl sulphoxide.

Suitable bases are sodium carbonate, potassium carbonate, triethylamine, ethyldiisopropylamine, sodium bicarbonate and, in particular, $Cs_2CO_3$. The reaction is normally carried out at a temperature of from 0 to 100° C., preferably 20 to 60° C.

Hydroxyl protective groups and suitable conditions for their introduction and elimination are described in detail in T. W. Greene, P. G. M. Wuts, "Protective Groups in Organic Synthesis, John Wiley and Sons, New York, 2nd edition, 1991. Examples of hydroxyl protective groups which may be mentioned are: trimethylsilyl, triisopropylsilyl, tert-butyldimethylsilyl, benzyl, benzyloxycarbonyl, 2-nitrobenzyl, 4-nitrobenzyl, tert-butoxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxycarbonylmethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl.

Compounds of the formula (II) can be prepared by the free OH group in compounds of the formula (VII) being protected with a protective group $PG^2$ or attached to a resin suitable for solid-phase synthesis, and in the group R being converted by standard reactions into the group $R^4$,

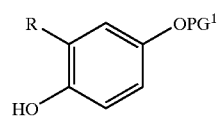

in which

R has the meaning indicated above, and $PG^1$ represents a hydroxyl protective group, in particular benzoyl.

The compounds of the formula (V) are obtained analogously from compounds of the formula (VII) by introducing the group $PG^2$ and then eliminating the group $PG^1$ selectively.

The process with its two variants is explained by way of example by the following diagram:

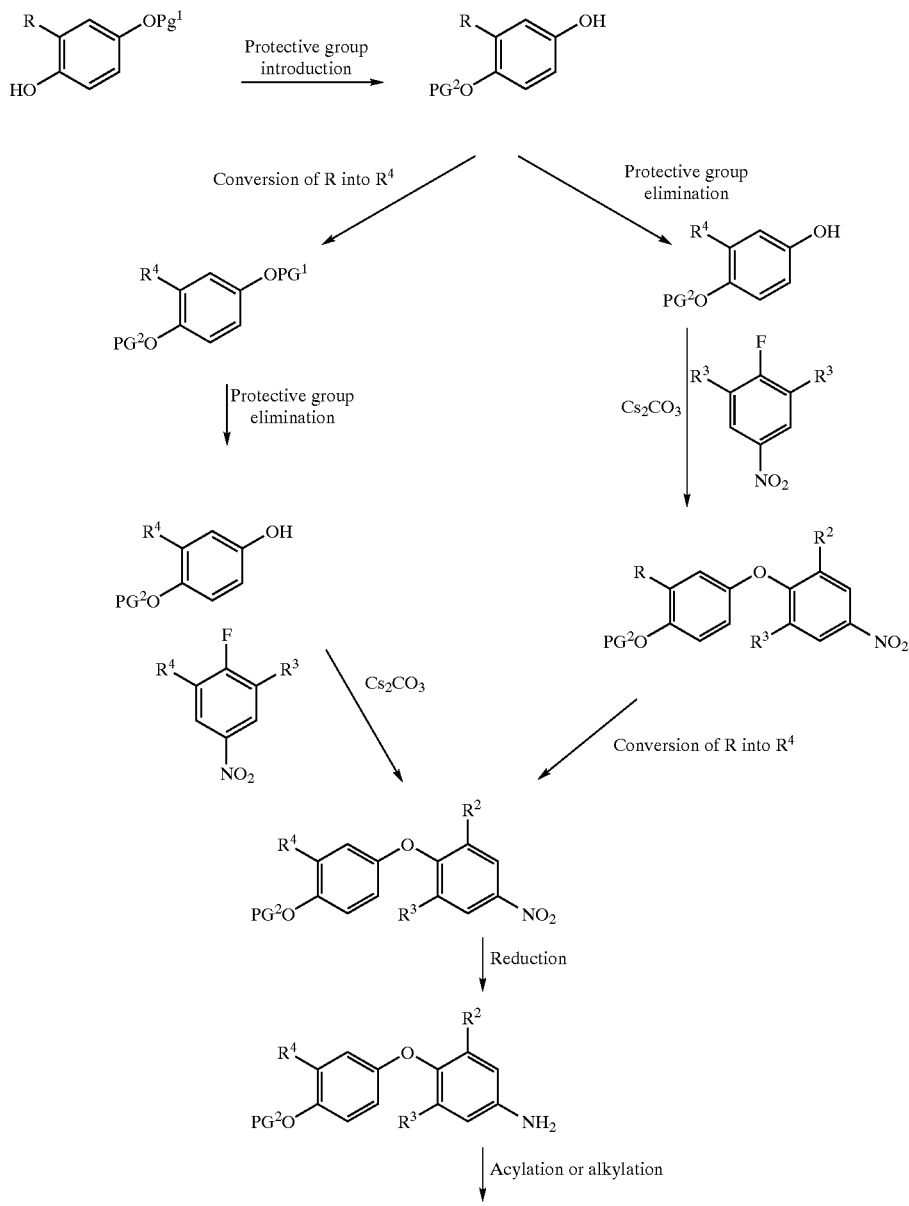

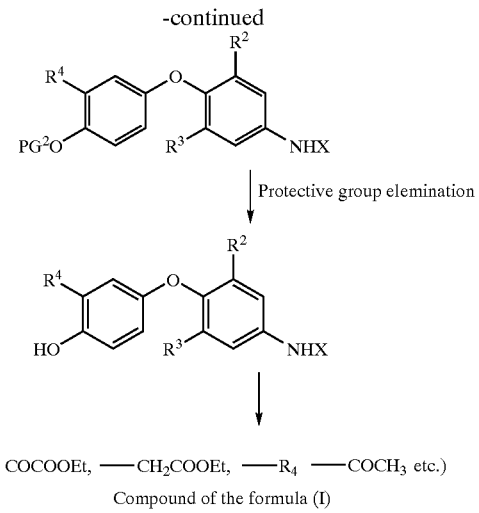

(X = COCOOEt, ——CH₂COOEt, ——R₄ ——COCH₃ etc.)

Compound of the formula (I)

The overall process can also be carried out as solid-phase synthesis. In this case, the compound of the formula (VII) is attached via its free OH group to a suitable resin, in which case $PG^2$ in the previous description of the synthesis represents the appropriate resin. The subsequent reactions are carried out on the solid phase, and the resulting compound is finally eliminated from the resin. Where it is intended to prepare compounds of the general formula (I) in which $R^5$ does not represent hydrogen, it is possible to modify the resulting compound further.

Solid-phase synthesis and the attachment of and elimination from the resin are familiar standard techniques. As an example of the comprehensive literature, reference may be made to the article "Linkers for Solid Phase Organic Synthesis, Ian W. James, Tetrahedron 55 (1999), 4855–4946".

The compounds according to the invention of the formula (I) show a surprising and valuable range of pharmacological actions and can therefore be employed as versatile medicaments. In particular, they can be employed for all indications which can be treated with natural thyroid hormones, such as, for example and preferably, depression, goitre or thyroid cancer. It is possible and preferred to use the compounds according to the invention of the formula (I) to treat arteriosclerosis, hypercholesterolaemia and dyslipidaemia. It is additionally possible to treat adiposity and corpulence (obesity), cardiac arrhythmias and heart failure, and achieve a postprandial reduction in triglycerides.

The compounds are also suitable for the treatment of certain airway disorders, in particular pulmonary emphysemas, and for medically promoting maturation of the lungs.

The compounds are also suitable for treatment of Alzheimer's disease.

The compounds are furthermore suitable for the treatment of osteoporosis.

The compounds can additionally be employed for the promotion and regeneration of hair growth and for the treatment of glaucoma.

The active substances according to the invention open up a further treatment alternative and represent an enrichment of pharmacy. Compared with known and previously employed thyroid hormone products, the compounds according to the invention show an improved range of action. They are preferably distinguished by great specificity, good tolerability and fewer side effects, in particular in the cardiovascular area.

Administration forms suitable for administering the compounds of the general formula (I) are all conventional ones, that is to say oral, parenteral, inhalation, nasal, sublingual, rectal or externals, such as, for example, transdermal, particularly preferably oral or parenteral. In connection with parenteral administration, particular mention should be made of intravenous, intramuscular, subcutaneous administration, for example as subcutaneous depot. Oral administration is very particularly preferred.

The active substances can in this connection be administered alone or in the form of pharmaceutical preparations. Preparations suitable for oral administration are, inter alia, tablets, capsules, pellets, coated tablets, pills, granules, solid and liquid aerosols, syrups, emulsions, suspensions and solutions. The active substance must be present in an amount such that a therapeutic effect is achieved. In general, the active substance can be present in a concentration of from 0.1 to 100% by weight, in particular 0.5 to 90% by weight, preferably from 5 to 80% by weight. The concentration of active substance should, in particular, be 0.5–90% by weight, that is to say the active substance should be present in amounts sufficient to reach the stated dose range.

For this purpose, the active substances can be converted in a manner known per se into the customary preparations. This takes place by use of inert, nontoxic, pharmaceutically acceptable carriers, excipients, solvents, vehicles, emulsifiers and/or dispersants.

Examples of excipients which may be mentioned are: water, nontoxic organic solvents such as, for example, paraffins, vegetable oils (for example sesame oil), alcohols (for example ethanol, glycerol), glycols (for example polyethylene glycol), solid carriers such as natural or synthetic ground minerals (for example talc or silicates), sugars (for example lactose), emulsifiers, dispersants (for example polyvinylpyrrolidone) and lubricants (for example magnesium sulphate).

In the case of oral administration, tablets can, of course, also contain additions such as sodium citrate together with additives such as starch, gelatin and the like. Aqueous preparations for oral administration may furthermore include flavour improvers or colorants.

The dosages administered on oral administration are preferably from 0.001 to 5 mg/kg, preferably 0.005 to 3 mg/kg, of body weight every 24 hours.

The activity of the compounds according to the invention can be tested for example in vitro by the known T3 promoter assay cell test which is described below.

The following examples are intended to explain the invention by way of example without having a restricted effect on the scope of protection.

| List of abbreviations | |
|---|---|
| DMF | dimethylformamide |
| DIEA | ethyldiisopropylamine |
| DMSO | dimethyl sulphoxide |
| TBTU | O-(benzotriazol-1-yl)-N,N,N',N'-tetra-methyluronium tetrafluoroborate |
| DCM | dichloromethane |
| TFA | trifluoroacetic acid |
| HPLC | high performance liquid chromatography |
| RP | reversed phase |
| RT | room temperature |
| ESI | electrospray ionization |

T3 Promoter Assay Cell Test

The test is carried out with a stably transfected human HepG2 hepatocarcinoma cell which expresses a luciferase gene under the control of a thyroid hormone-regulated promoter. The vector used for the transfection has upstream of the luciferase gene a minimal thymidine kinase promoter with a thyroid hormone-responsive element (TRE) which consists of two inverted palindromes each of 12 bp and of an 8 bp spacer.

For the test, the cell cultures are seeded in Eagle's minimal essential medium in 96-well plates with the following additions: glutamine, tricine, sodium pyruvate, non-essential amino acids, insulin, selenium and transferrin. The cultures are grown at 37° C. with a 10% $CO_2$ atmosphere for 48 hours. In serial dilutions of test substance or reference compound (triiodothyronine=T3, thyroxine=T4) and costimulator retinoic acid are added to the test cultures and the latter are incubated as previously for a further 48 or 72 hours. Each substance concentration is tested in four replicates. To determine the luciferase induced by T3 or other substances, the cells are subsequently lysed by adding a Triton- and luciferin-containing buffer and measured immediately in a luminometer. The $EC_{50}$ values for each compound are calculated (see Table 1).

TABLE 1

| Example | $EC_{50}$ [nM] |
|---|---|
| 8 | 20 |
| 16 | 28 |
| 29 | 2.4 |
| 54 | 6.7 |
| 122 | 55 |
| 190 | 14 |
| 204 | 61 |
| 260 | 12 |

The compounds according to the invention also show surprisingly advantageous properties in the in vivo test described below:

Description of Test for Finding Pharmacologically Active Substances Which Lower the Serum Cholesterol in Mice The substances to be investigated for their serum cholesterol-lowering effect in vivo are administered orally to male mice with a body weight between 25 and 35 g. One day before starting the test, the animals are divided into groups with an identical number of animals, usually n=7–10. Throughout the test drinking water and feed are available ad libitum to the animals. The substances are administered orally once a day for 7 days. For this purpose, the test substances are dissolved in a solution of Solutol HS 15+ethanol+saline (0.9%) in the ratio 1+1+8 or in a solution of Solutol HS 15+saline (0.9%) in the ratio 2+8. The dissolved substances are administered by gavage in a volume of 10 ml/kg of body weight. Animals treated in exactly the same way but receiving only the solvent (10 ml/kg of body weight) without test substance serve as control group.

Before the first administration of substance, blood is taken from each mouse by puncture of the retroorbital venous plexus for determination of the serum cholesterol (initial value). The test substance is then administered to the animals by gavage for the first time. 24 hours after the last administration of substance (on the 8th day after the start of treatment), blood is again taken from each animal by puncture of the retroorbital venous plexus for determination of the serum cholesterol. The blood samples are centrifuged and, after the serum is obtained, the cholesterol is determined by photometry using an EPOS analyser 5050 (Eppendorf-Gerätebau, Netheler & Hinz GmbH, Hamburg). The determination takes place with a commercially available enzyme assay (Boehringer Mannheim, Mannheim).

The effect of the test substances on the serum cholesterol concentration is determined by subtracting the cholesterol level in the 1st blood sample (initial value) from the cholesterol level in the 2nd sample (after treatment). The differences of all the cholesterol levels in a group are averaged and compared with the average of the differences in the control group.

Statistical analysis takes place using Student's t test after previous checking of the variants for homogeneity.

Substances which reduce the serum cholesterol in the treated animals compared with the control group statistically significantly (p<0.05) by at least 10% are judged as pharmacologically active.

Attachment of 5-benzoyloxy-2-hydroxybenzaldehyde to Wang Bromide Resin

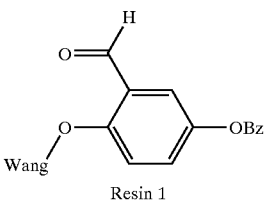

Resin 1

Wang bromide resin (32.0 g, 45.8 mmol, NovaBiochem) is suspended in acetonitrile/dioxane (1:1, 300 ml) and, after addition of diisopropylethylamine (17.7 g, 3.00 eq), caesium iodide (5.94 g, 0.50 eq), 18-crown-6 (6.05 g, 0.50 eq) and 5-benzoyloxy-2-hydroxybenzaldehyde (14.4 g, 1.3 eq) [J. G. Bruno, M. N. Chang, Y. M. Choi-Sledeski, D. M. Green, D. G. McGarry, J. R. Regan, F. A. Volz, J.Org.Chem. (1997), 62, 5174–5190], shaken at 55° C. for 20 h. The reaction mixture is filtered and the resulting resin 1 is washed repeatedly with water, methanol, DCM and diethyl ether and dried. The loading is determined by elimination with TFA/DCM, 1:1, from a resin sample. A loading of 1.35 mmol/g 5-benzoyloxy-2-hydroxybenzaldehyde is found by quantitative HPLC.

Solid-phase Ester Hydrolysis

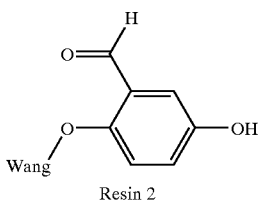

Resin 2

Resin 1 (32.0 g) is suspended in dioxane (180 ml) and, after addition of a solution of KOH (5.13 g, 2 eq) in methanol (60 ml), shaken at room temperature for 15 minutes. The resulting resin 2 is filtered and washed repeatedly with methanol, water, methanol, DCM and diethyl ether and dried.

Solid-phase Formation of the Phenyl Ether

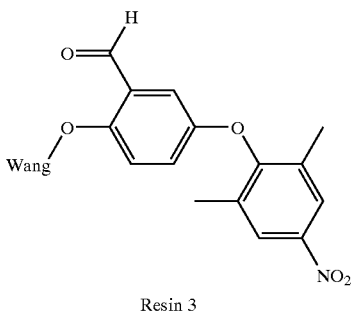

Resin 3

Resin 2 (32 g) is suspended in DMSO (300 ml) and reacted with $Cs_2CO_3$ (29.8 g, 2 eq), 18-crown-6 (12.1 g, 1 eq) and 2-fluoro-1,3-dimethyl-5-nitrobenzene (11.6 g, 1.5 eq) at 40° C. for 1 h. The resin is then washed repeatedly with water/DMF (1:1), water, DMF, methanol, DCM and diethyl ether and dried.

Preparation of a Library Ia

This and the following libraries are prepared in MiniKans (IRORI) by the mix and split method [K. C. Nicolaou, X.-Y. Xiao, Z. Parandoosh, A. Senyei, M. P. Nova, Angew. Chem. Int. Ed. Engl. (1995), 35, 2289–2290].

Preparation of the library Ia is depicted by way of example in diagram 1.

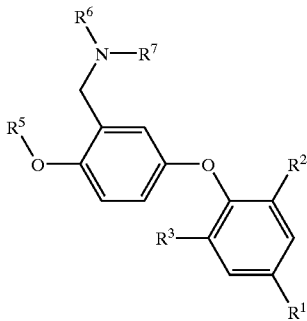

Ia

Resin 3 is suspended in DCM/DMF, 2:1 in IRORI MiniKans (about 120 mg/Kan in each case) and washed repeatedly with DCM and diethyl ether and dried.

The resin compartmented in this way is suspended in DCM/trimethyl orthoformate (1:1) in separate reaction vessels to each of which an amine (5 eq, "amine A") is added at room temperature and shaken for 18 h. The resin in the separate reaction vessels is washed several times with DMF and suspended in DMF and, at room temperature, tetrabutylammonium borohydride (2 eq) is added. After shaking at room temperature for 5 minutes, the reaction mixture is cooled to −40° C. and, after addition of glacial acetic acid (100 eq), warms to room temperature again. The resin is washed repeatedly with water, methanol, DCM/10% of DIEA, methanol, DCM and diethyl ether and dried. The resin is resuspended in dioxane in separate reaction vessels and, after addition of DIEA (20 eq), tetrabutylammonium iodide (2 eq) and alkyl or benzyl halide (10 eq each, "halide B"), stirred at 70° C. for 18 h. To synthesize secondary amines ($R^7$=H), in place of the alkylation the resin is suspended in dioxane/2-propanol, 3/1, and, after addition of triethylamine (2 eq) and bis-tert-butyl pyrocarbonate (10 eq), shaken at RT for 2 h.

The resin is filtered again and washed repeatedly with water, DMF, methanol, DCM and diethyl ether and dried. The resin is suspended in DMF/water, 9:2, and, after addition of tin(II) chloride dihydrate (5 eq), reacted at 60° C. for 2 hours and washed repeatedly with water, DMF, methanol, DCM and diethyl ether. The resin compartments are again distributed to separate reaction vessels, suspended in DCM and reacted with DIEA (10 eq) and various acid chlorides or chloroformic esters (5 eq of each "acid chloride C") at room temperature for 18 h. The resin is reacted analogously in a reaction vessel with ethyl bromoacetate (5 eq) at 40° C. overnight. The resin is finally washed repeatedly with methanol, DMF, water, DMF, methanol, DCM and diethyl ether and dried. The products are then cleaved off the solid phase with TFA/dichloromethane (1:1), the resin is filtered off, and the reaction solutions are evaporated in order to obtain a set of amines Ia.

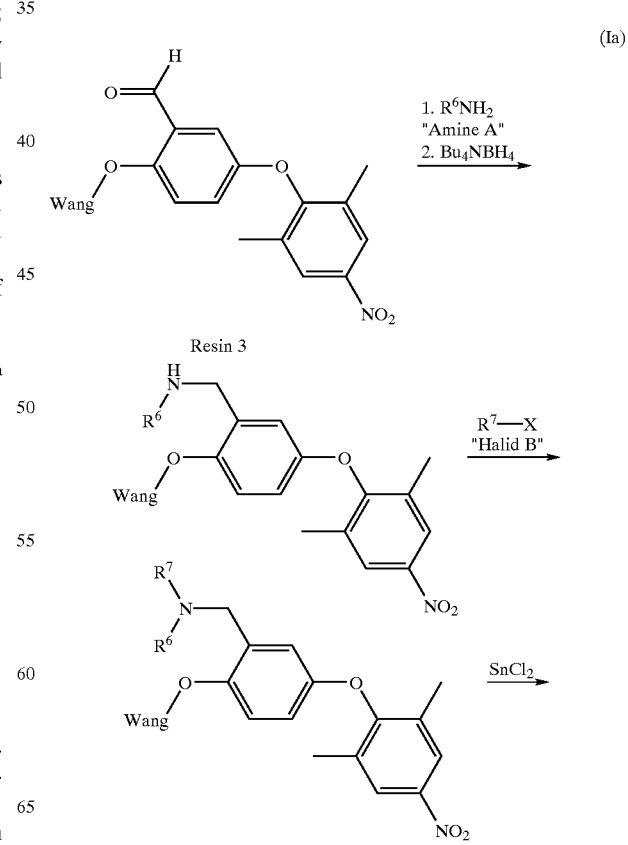

-continued

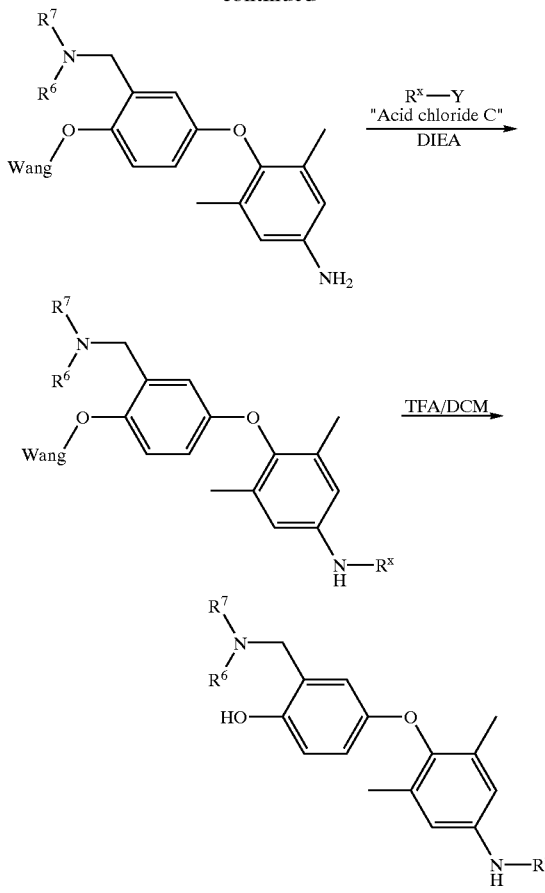

$R^x$ corresponds to a radical of the formula $CH_3CO—$, $C_2H_5OOCCH_2—$ or $C_2H_5OOCCO—$, Y corresponds to a suitable leaving group such as, for example, Cl, Br.

Diagram 1

Preparation of a Library Ib

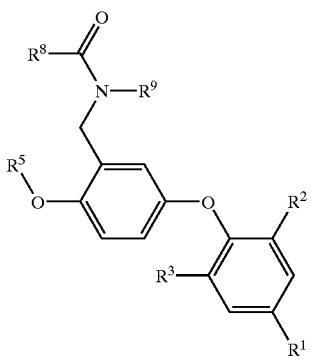

Preparation of the library Ib is depicted by way of example in diagram 2.

Resin 3 is suspended in DCM/DMF, 2:1, in IRORI MiniKans (in each case about 120 mg/Kan) and washed repeatedly with DCM and diethyl ether and dried.

The resin compartmented in this way is suspended in DCM/trimethyl orthoformate (1:1) in separate reaction vessels to each of which an amine (5 eq, "amine A") is added at room temperature and shaken for 18 h. The resin in the separate reaction vessels is washed several times with DMF and suspended in DMF and, at room temperature, tetrabutylammonium borohydride (2 eq) is added. After shaking at room temperature for 5 minutes, the reaction mixture is cooled to −40° C. and, after addition of glacial acetic acid (100 eq), warmed to room temperature again. The resin is washed repeatedly with 20% glacial acetic acid in methanol, water, DMF, 10% triethylamine in DCM, DCM and diethyl ether and dried. The resin is again suspended in DCM in separate reaction vessels and, after addition of DIEA (10 eq) and one acid chloride (5 eq, "acid chloride B") in each case, shaken at room temperature for 2 h. The resin is filtered and washed repeatedly with methanol, DCM and diethyl ether and dried. The resin is suspended in DMF/water, 9:2, and, after addition of tin(II) chloride dihydrate (5 eq), reacted at 40° C. for 4 hours and washed repeatedly with water, DMF, methanol, DCM and diethyl ether. The resin compartments are again distributed to separate reaction vessels, suspended in DCM and reacted with DIEA (10 eq) and in each case one acid chloride or chloroformic ester (5 eq, "acid chloride C") at room temperature for 18 h. The resin is reacted analogously in a reaction vessel with ethyl bromoacetate (5 eq) at 40° C. overnight. The resin is finally washed repeatedly with methanol, DMF, water, DMF, methanol, DCM and diethyl ether and dried. The products are then cleaved off the solid phase with TFA/dichloromethane (1:1), the resin is filtered off, and the reaction solutions are separated in order to obtain a set of amides Ib.

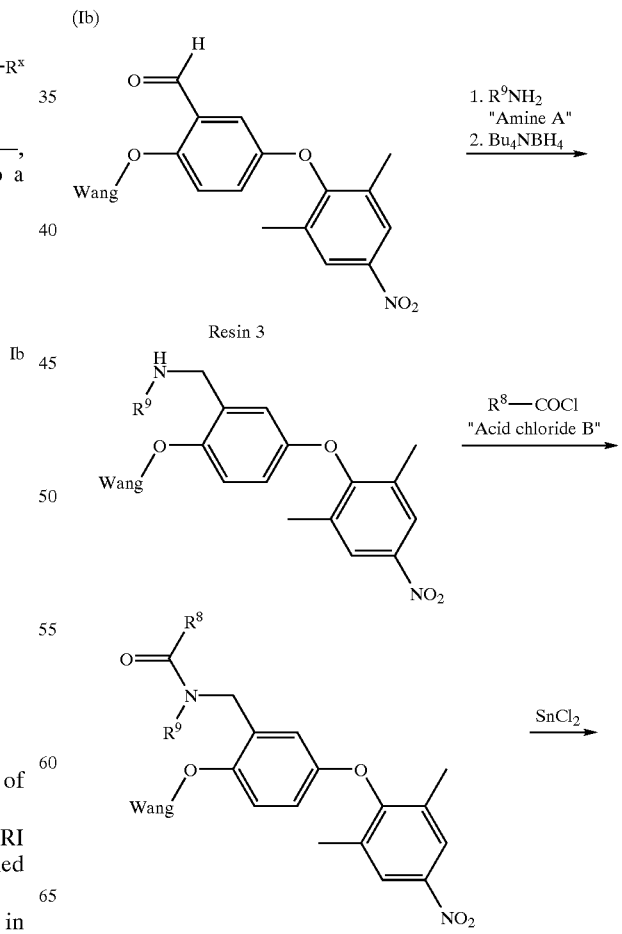

-continued

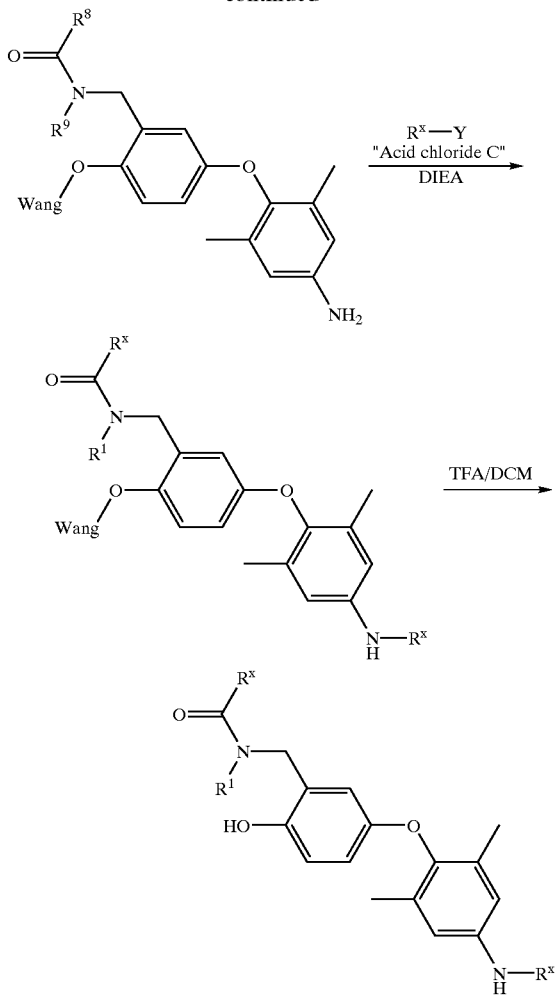

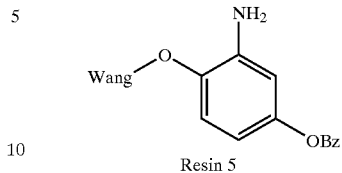

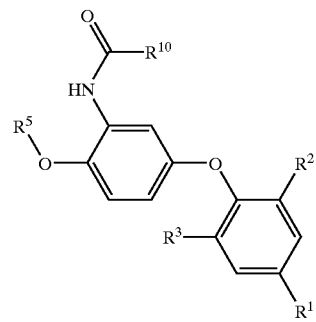

$R^x$ corresponds to a radical of the formula $CH_3CO—$, $C_2H_5OOCCH_2—$ or $C_2H_5OOCCO—$, Y corresponds to a suitable leaving group such as, for example, Cl, Br.

Diagram 2

Attachment of 4-benzoyloxy-2-nitrophenol to Wang Bromide Resin

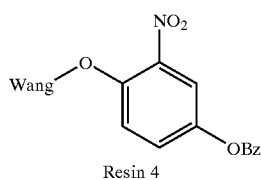

Resin 4

Wang bromide resin (25.0 g, 35.0 mmol, NovaBiochem) is suspended in dimethylacetamide (150 ml) and, after addition of diisopropylethylamine (22.6 g, 5.0 eq), caesium iodide (4.55 g, 0.50 eq) and 4-hydroxy-3-nitrophenyl benzoate (27.2 g, 3.0 eq) [M. Svensson, B. Helgee, K. Skarp, G. Andersson, J.Mater.Chem.(1998), 8, 353–362], shaken at room temperature overnight. The reaction mixture is filtered and the resin 4 is washed repeatedly with methanol, water, DMF, methanol, DCM and diethyl ether and dried. The loading is determined by elimination with TFA/DCM 1:1, from a resin sample. A loading of 0.87 mmol/g 4-benzoyloxy-2-nitrophenol is found by quantitative HPLC.

Reduction of the Nitro Group on Resin 4

Resin 4 (60 g) is suspended with tin(II) chloride dihydrate (94.8 g, 420 mmol) in DMF/water, 9:1, and stirred at 60° C. for 2 h. The reaction mixture is filtered and the resin 5 is washed repeatedly with water, methanol, DCM and diethyl ether and dried.

Preparation of a Library Ic

Ic

Resin 5 is suspended in DCM/DMF, 2:1, in IRORI MiniKans (in each case about 120 mg/Kan) and washed repeatedly with DCM and diethyl ether and dried.

a) Preparation of amides and Urethanes ($R^{10}\neq NR^{14}R^{15}$)

Preparation of the amide library Ic is depicted by way of example in diagram 3.

The compartmented aniline resin is suspended in DCM in separate reaction vessels, and DIEA (10 eq) and in each case one acid chloride (5 eq, "acid chloride A") are added at 0° C.—room temperature. This reaction mixture is shaken at room temperature overnight. The resin is washed repeatedly with methanol, DCM and diethyl ether and dried. The resin is mixed with a solution of potassium hydroxide (2 eq) in dioxane/methanol (2:1) and shaken at room temperature for 45 minutes, filtered and washed repeatedly with methanol, DCM and diethyl ether and dried. The resin is suspended in DMSO and reacts with caesium carbonate (3 eq), 18-crown-6 (1 eq) and 2-fluoro-1,3-dimethyl-5-nitrobenzene (5 eq) at 55° C. for 60 h. The resin is then washed repeatedly with water, DMF, methanol, DCM and diethyl ether and dried. The resin is suspended in DMF/water, 9:2, and, after addition of tin(II) chloride dihydrate (5 eq), reacted at 60° C. for 90 minutes and washed repeatedly with methanol, DCM and diethyl ether. The resin compartments are again distributed to separate reaction vessels, suspended in DCM and reacted with DIEA (10 eq) and various acid chlorides or chloroformic esters (5 eq, "acid chloride B") at room temperature for 6 h. The resin in one reaction vessel is reacted analogously with ethyl bromoacetate (5 eq) at 40° C. overnight. The resin is finally washed repeatedly with methanol, DMF, water, DMF, methanol, DCM and diethyl ether and dried. The products are then cleaved off the solid phase with TFA/dichloromethane (1:1), the resin is filtered off, and the reaction solutions are evaporated to obtain a set of amides Ic.

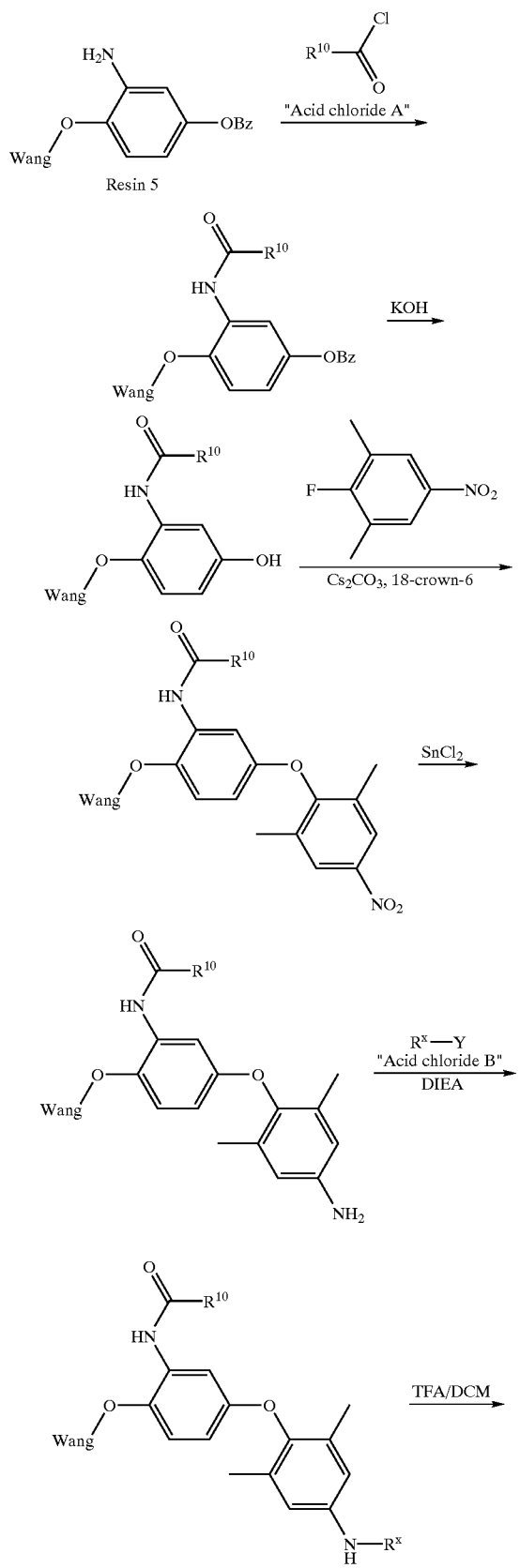

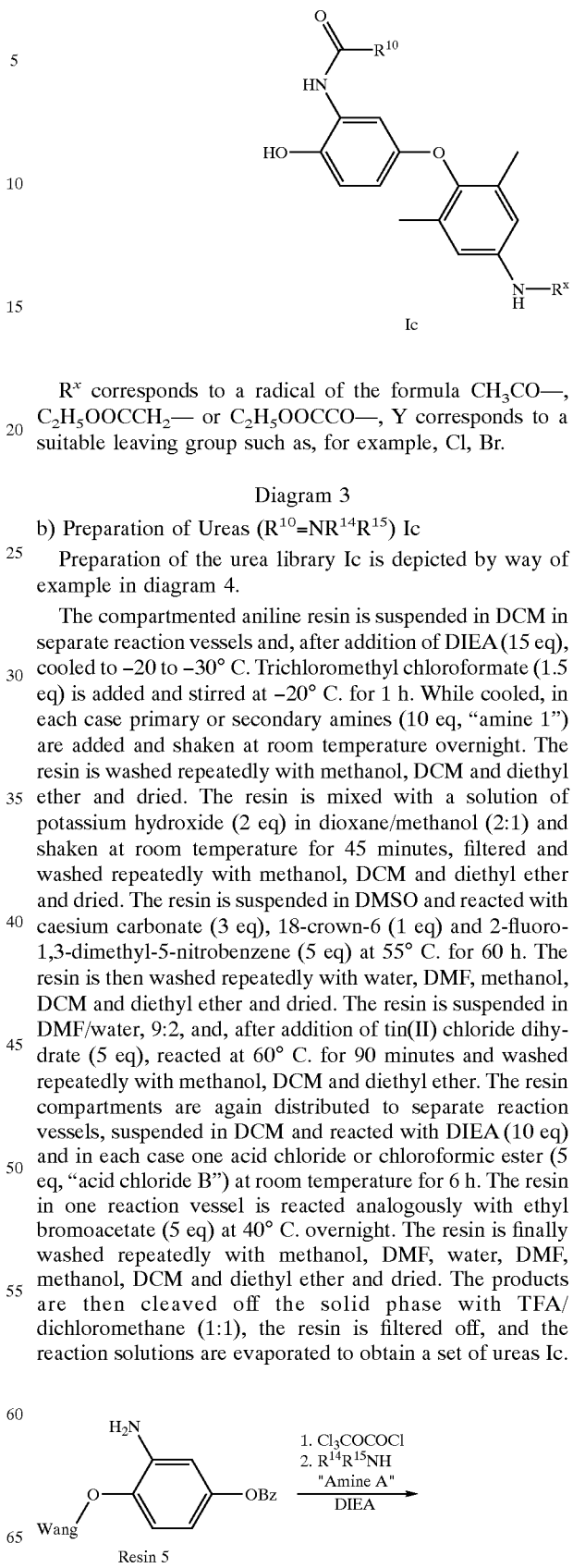

$R^x$ corresponds to a radical of the formula $CH_3CO$—, $C_2H_5OOCCH_2$— or $C_2H_5OOCCO$—, Y corresponds to a suitable leaving group such as, for example, Cl, Br.

Diagram 3 b) Preparation of Ureas ($R^{10}$=$NR^{14}R^{15}$) Ic

Preparation of the urea library Ic is depicted by way of example in diagram 4.

The compartmented aniline resin is suspended in DCM in separate reaction vessels and, after addition of DIEA (15 eq), cooled to −20 to −30° C. Trichloromethyl chloroformate (1.5 eq) is added and stirred at −20° C. for 1 h. While cooled, in each case primary or secondary amines (10 eq, "amine 1") are added and shaken at room temperature overnight. The resin is washed repeatedly with methanol, DCM and diethyl ether and dried. The resin is mixed with a solution of potassium hydroxide (2 eq) in dioxane/methanol (2:1) and shaken at room temperature for 45 minutes, filtered and washed repeatedly with methanol, DCM and diethyl ether and dried. The resin is suspended in DMSO and reacted with caesium carbonate (3 eq), 18-crown-6 (1 eq) and 2-fluoro-1,3-dimethyl-5-nitrobenzene (5 eq) at 55° C. for 60 h. The resin is then washed repeatedly with water, DMF, methanol, DCM and diethyl ether and dried. The resin is suspended in DMF/water, 9:2, and, after addition of tin(II) chloride dihydrate (5 eq), reacted at 60° C. for 90 minutes and washed repeatedly with methanol, DCM and diethyl ether. The resin compartments are again distributed to separate reaction vessels, suspended in DCM and reacted with DIEA (10 eq) and in each case one acid chloride or chloroformic ester (5 eq, "acid chloride B") at room temperature for 6 h. The resin in one reaction vessel is reacted analogously with ethyl bromoacetate (5 eq) at 40° C. overnight. The resin is finally washed repeatedly with methanol, DMF, water, DMF, methanol, DCM and diethyl ether and dried. The products are then cleaved off the solid phase with TFA/dichloromethane (1:1), the resin is filtered off, and the reaction solutions are evaporated to obtain a set of ureas Ic.

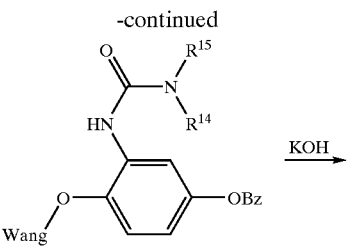

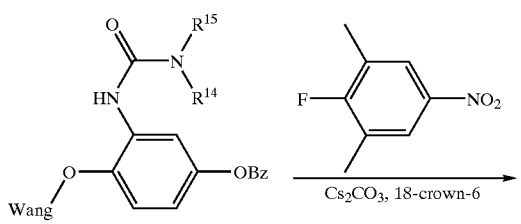

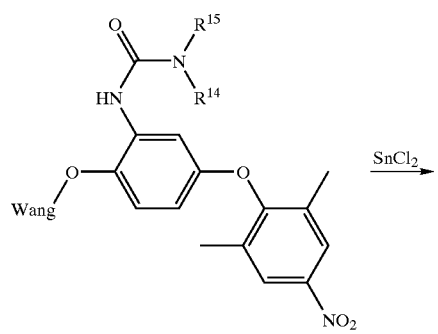

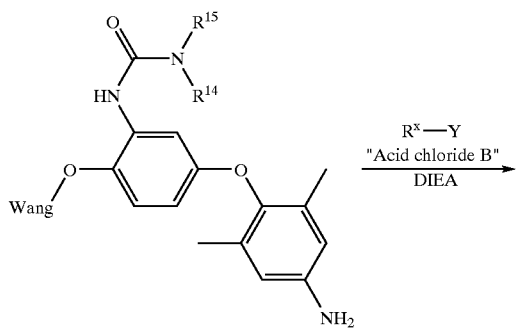

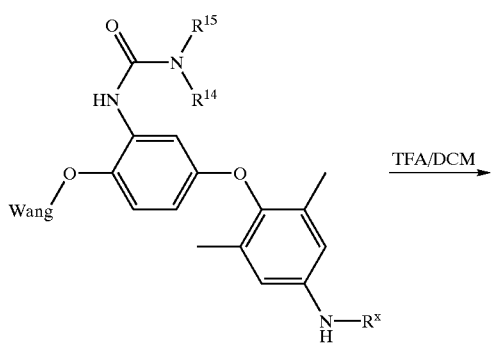

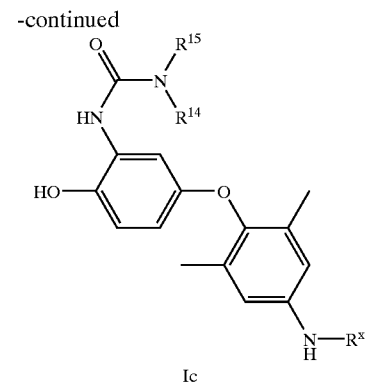

Ic $R^x$ corresponds to a radical of the formula $CH_3CO-$, $C_2H_5OOCCH_2-$ or $C_2H_5OOCCO-$, Y corresponds to a suitable leaving group such as, for example, Cl, Br.

Diagram 4
Ethyl 5-benzoyloxy-2-hydroxybenzoate 6

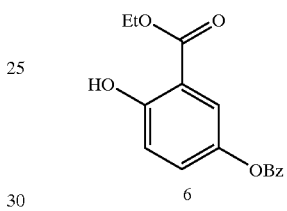

6

5-Benzoyloxy-2-hydroxybenzoic acid [M. Bergmann, P. Dangschat, Chem Ber. (1919), 52, 371–387] (2.00 g, 7.74 mmol) is suspended in DMF (10 ml), and diisopropylethylamine (1.20 g, 9.29 mmol), caesium iodide (0.201 g, 0.77 mmol) and iodoethane (2.42 g, 15.5 mmol) are added. The reaction mixture is stirred at room temperature overnight and taken up in diethyl ether. The organic phase is washed with water, saturated $NaHCO_3$ solution, 1 N HCl and saturated NaCl solution, dried with $MgSO_4$, decanted and evaporated. The crude product is purified by flash column chromatography on silica gel by petroleum ether/ethyl acetate, 1:0–9:1.

Yield: 1.96 g (89%) 6.

$^1$H-NMR (400 MHz, $CDCl_3$): 1.41, t, 3H; 4.41, q, 2H; 7.03, d, 1H; 7.31, dd, 1H; 7.48–7.55, m, 2H; 7.61–7.68, 1H; 7.70, d, 1H; 8.19, d, 2H; 10.78, s, 1H.

Attachment of Ethyl 5-benzoyloxy-2-hydroxybenzoate (6) to Wang Bromide Resin

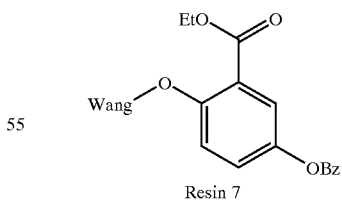

Resin 7

Wang bromide resin (50.0 g, 70.0 mmol, NovaBiochem) is suspended in acetonitrile/dioxane (1:1, 300 ml) and, after addition of diisopropylethylamine (90.4 g, 10.0 eq), caesium iodide (1.82 g, 0.10 eq), 18-crown-6 (18.5 g, 1 eq) and ethyl 5-benzoyloxy-2-hydroxybenzoate (6) (30.1 g, 1.5 eq), shaken at 80° C. overnight. The reaction mixture is filtered and the resin 7 is washed repeatedly with DMF, water, methanol, DCM and diethyl ether and dried. The loading is determined by elimination with TFA/DCM, 1:1, from a resin sample. A loading of 0.42 mmol/g ethyl 5-benzoyloxy-2-hydroxybenzoate (6) is found by quantitative HPLC.

Selective Solid-phase Ester Hydrolysis

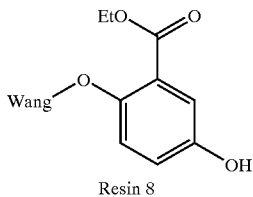

Resin 8

Resin 7 (50 g) is suspended in dioxane (260 ml) and, after addition of a solution of KOH (4.94 g) in methanol (130 ml), shaken at room temperature for 5 minutes. The resulting resin 8 is filtered and washed repeatedly with DMF, 10% glacial acetic acid in DCM, methanol, DCM, diethyl ether and dried.

Solid-phase Formation of the Phenyl Ether

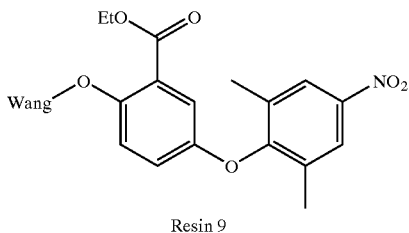

Resin 9

Resin 8 (33 g) is suspended in DMSO (300 ml) and reacted with $Cs_2CO_3$ (14.2 g), 18-crown-6 (3.84 g) and 2-fluoro-1,3-dimethyl-5-nitrobenzene (5 eq) at 90° C. for 20 h. The resulting resin 9 is then washed repeatedly with water/DMF (1:1), water, DMF, methanol, DCM and diethyl ether and dried.

Solid-phase Ester Hydrolysis

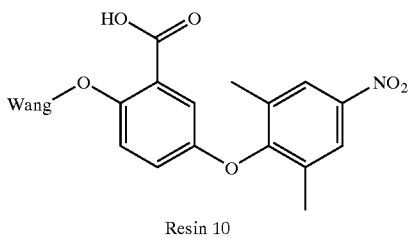

Resin 10

Resin 9 (32 g) is suspended in dioxane (260 ml) and, after addition of a solution of KOH (7.90 g) in methanol (130 ml), stirred at 50° C. for 1 h. The resulting resin 10 is filtered and washed three times with methanol, 10% glacial acetic acid in DCM, methanol, DCM and diethyl ether and dried.

Preparation of a Library Id

Preparation of the library Id is depicted by way of example in diagram 5.

Resin 10 is suspended in DCM/DMF, 2:1, in IRORI MiniKans (in each case about 120 mg/Kan) and washed repeatedly with DCM and diethyl ether and dried.

The resin compartmented in this way is suspended in DCM in separate reaction vessels and, after addition of DIEA (10 eq), in each case one amine (5 eq, "amine A") and TBTU (5 eq) at room temperature, shaken overnight. The resin is washed repeatedly with methanol, DCM and diethyl ether and dried. The resin is suspended in DMF/water, 9:2, and, after addition of tin(II) chloride dihydrate (5 eq), reacted at 40° C. for 4 hours and washed repeatedly with methanol, DCM and diethyl ether. The resin compartments are again distributed to separate reaction vessels, suspended in DCM and reacted with DIEA (10 eq) and in each case one acid chloride or chloroformic ester (5 eq, "acid chloride B") at room temperature for 18 h. The resin in one reaction vessel is reacted analogously with ethyl bromoacetate (5 eq) at 40° C. overnight. The resin is washed repeatedly with methanol, DMF, water, DMF, methanol, DCM and diethyl ether and dried. The products are cleaved off the solid phase with TFA/dichloromethane (1:1), the resin is filtered off, and the reaction solutions are evaporated in order to obtain a set of carboxamides Id.

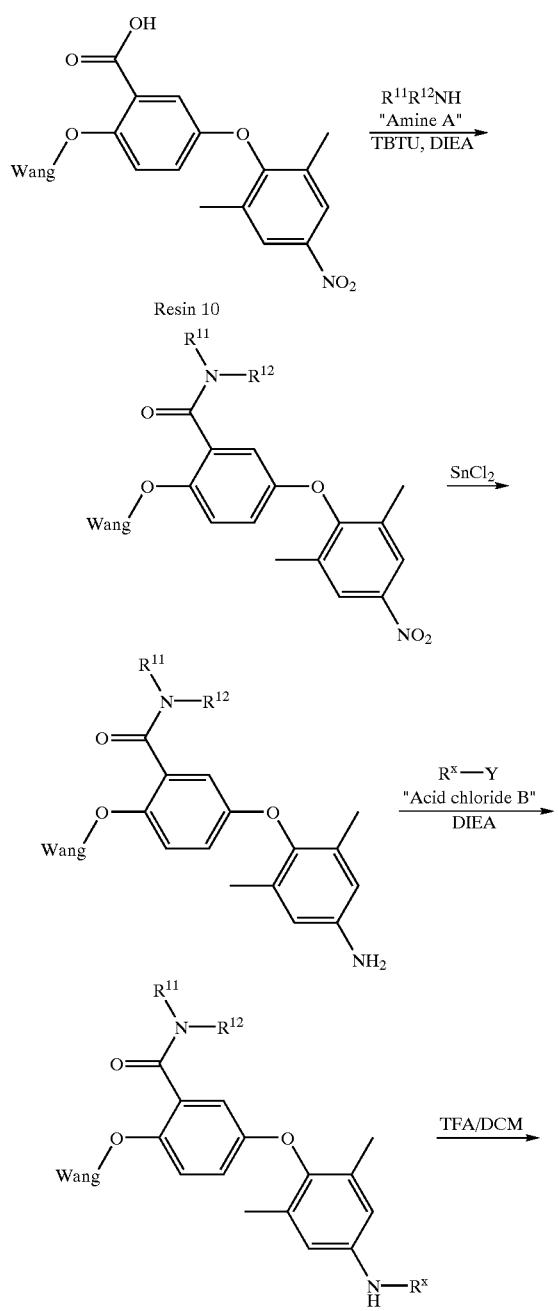

-continued

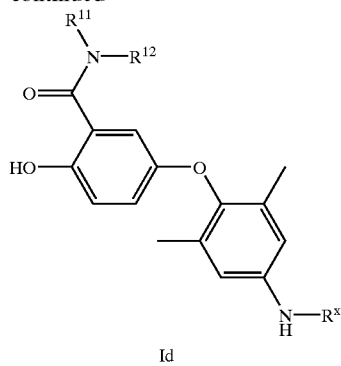

Id

R$^x$ corresponds to a radical of the formula CH$_3$CO—, C$_2$H$_5$OOCCH$_2$— or C$_2$H$_5$OOCCO—, Y corresponds to a suitable leaving group such as, for example, Cl, Br.

Diagram 5

PREPARATION EXAMPLES

Example 1

Ethyl {[4-(3-{[benzyl(isopropyl)amino]methyl}-4-hydroxyphenoxy)-3,5-dimethylphenyl]amino}(oxo)acetate

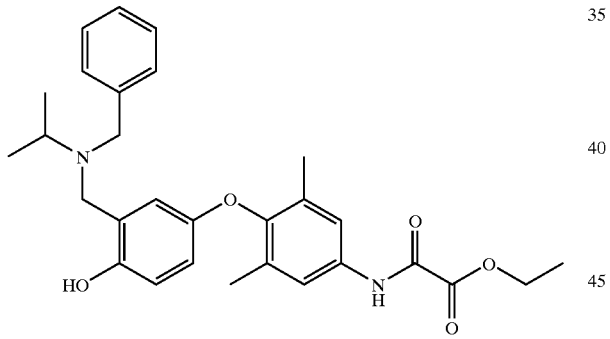

In accordance with the general procedure for preparing the library Ia, 1.00 g of resin 3 is reacted with isopropylamine as "amine A", benzyl chloride as "halide B" and ethoxalyl chloride as "acid chloride C". The resulting crude product is purified by preparative RP-HPLC with a water/acetonitrile/TFA eluent. This product is partitioned between saturated NaHCO$_3$ solution and DCM, and the organic phase is salted out with NaCl, decanted and evaporated.

Yield: 30 mg of ethyl {[4-(3-{[benzyl(isopropyl)amino]methyl}-4-hydroxyphenoxy)-3,5-dimethylphenyl]amino}(oxo)acetate $^1$H-NMR (200 MHz, CDCl$_3$): 1.13, d, 6H; 1.44, t, 3H; 2.11, s, 6H ; 3.09, sept, 1H; 3.60, s, 2H; 3.71, s, 2H; 4.42, q, 2H; 6.40, d, 1H; 6.52, dd, 1H; 6.69, d, 1H; 7.20–7.40, m, 7H; 8.77, s, 1H.

Example 2

Ethyl {[4-(3- {[benzyl(cyclohexyl)amino]methyl}-4-hydroxyphenoxy)-3,5-dimethylphenyl]amino }(oxo)acetate

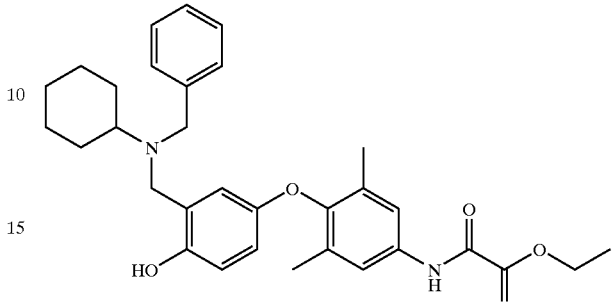

In accordance with the general procedure for preparing the library Ia, 1.00 g of resin 3 is reacted with cyclohexylamine as "amine A", benzyl chloride as "halide B" and ethoxalyl chloride as "acid chloride C". The resulting crude product is purified by preparative RP-HPLC with a water/acetonitrile/TFA eluent. This product is partitioned between saturated NaHCO$_3$ solution and DCM, and the organic phase is salted out with NaCl, decanted and evaporated.

Yield: 30mg of ethyl {[4-(3-{[benzyl(cyclohexyl)amino]methyl}-4-hydroxyphenoxy)-3,5-dimethylphenyl]amino}(oxo)acetate $^1$H-NMR (200 MHz, CDCl$_3$): 1.00–1.95, m, 10H ; 1.43, t, 3H; 2.12, s, 6H ; 2.61, nm, 1H; 3.64, s, 2H; 3.75, s, 2H; 4.42, q, 2H; 6.39, d, 1H; 6.52, dd, 1H; 6.67, d, 1H; 7.20–7.40, m, 7H; 8.77, s, 1H.

Example 3

Ethyl {[4-(3- {[cyclohexyl(4-fluorobenzyl)amino]methyl}-4-hydroxyphenoxy)-3,5-dimethylphenyl]amino}(oxo)acetate

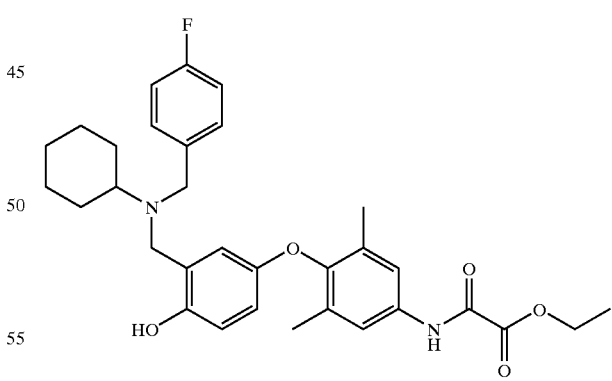

In accordance with the general procedure for preparing the library Ia, 1.00 g of resin 3 is reacted with cyclohexylamine as "amine A", 4-fluorobenzyl chloride as "halide B" and ethoxalyl chloride as "acid chloride C". The resulting crude product is purified by preparative RP-HPLC with a water/acetonitrile/TFA eluent. This product is partitioned between saturated NaHCO$_3$ solution and ethyl acetate, and the ethyl acetate phase is salted out with NaCl, decanted and evaporated.

Yield: 30 mg of ethyl {[4-(3-{[cyclohexyl(4-fluorobenzyl)amino]methyl}-4-hydroxyphenoxy)-3,5-dimethylphenyl]amino}(oxo)acetate ¹H-NMR (200 MHz, CDCl₃): 1.20, d, 6H; 1.44, t, 3H; 2.11, s, 6H ; 3.20, sept, 1H; 3.68, s, 2H; 3.76, s, 2H; 4.42, q, 2H; 6.40, d, 1H; 6.57, dd, 1H; 6.75, d, 1H; 6.95–7.10, m, 2H; 7.25–7.33, dd, 2H; 7.36, s, 2H; 8.79, s, 1H.

Example 4

{[4-(3-{[Benzyl(isopropyl)amino]methyl}-4-hydroxyphenoxy)-3,5-dimethylphenyl]amino}(oxo)acetic acid

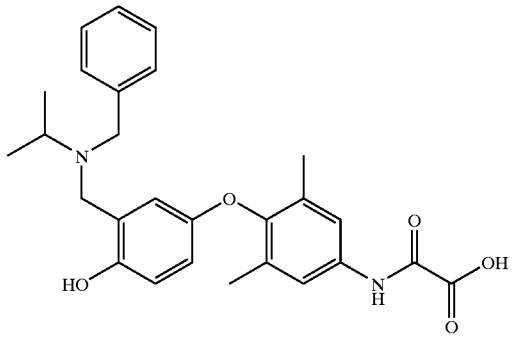

Ethyl {[4-(3-{[benzyl(isopropyl)amino]methyl}-4-hydroxyphenoxy)-3,5-dimethylphenyl]amino}(oxo)acetate (50 mg, 0,10 mmol) and NaOH (40 mg, 1.02 mmol) are dissolved in dioxane/water (0.5 1, 1:1 v/v) and stirred at room temperature for 1 h. The reaction mixture is partitioned between ethyl acetate and potassium dihydrogen phosphate/disodium hydrogen phosphate buffer solution (pH 7), and the organic phase is salted out with NaCl, filtered and evaporated. The resulting crude product is purified by preparative RP-HPLC with a water/acetonitrile/TFA eluent.

Yield: 23 mg of {[4-(3-{[benzyl(isopropyl)amino]methyl}-4-hydroxyphenoxy)-3,5-dimethylphenyl]amino}(oxo)acetic acid

MS: 463.2 [MH⁺]

Example 5

Ethyl (4-{4-hydroxy-3-[(2-phenoxybutanoyl)amino]phenoxy}-3,5-dimethylanilino)(oxo)acetate

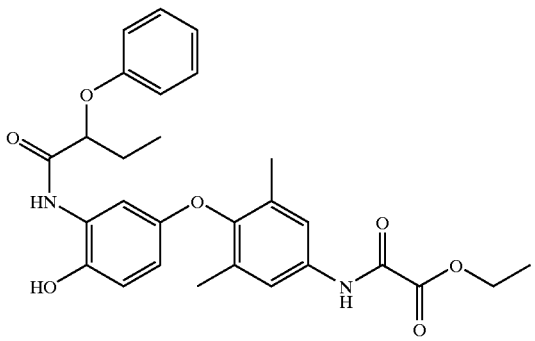

In accordance with the general procedure for preparing the library Ic, 1.5 g (0.13 mmol) of resin 5 are reacted with 2-phenoxybutyryl chloride as "acid chloride A" and ethoxalyl chloride as "acid chloride B". The resulting crude product is purified by preparative RP-HPLC with a water/acetonitrile/TFA eluent.

Yield: 0.305 g of ethyl (4-{4-hydroxy-3-[(2-phenoxybutanoyl)amino]phenoxy}-3,5-dimethylanilino)(oxo)acetate ¹H-NMR (400 MHz, CDCl₃): 1.09, t, 3H; 1.43, t, 3H; 1.95–2.12, m, 2H; 2.10, s, 6H ; 4.42, q, 2H; 4.71, dd, 1H; 6.43, d, 1H; 6.51, dd, 1H; 6.90, d, 1H; 6.97, d, 2H; 7.06, t, 1H; 7.31, d, 2H; 7.35, s, 2H; 8.33 s, 1H; 8.77, s, 1H.

MS: 507 [MH⁺].

Example 6

Ethyl (4-{3-[(biphenyl-4-ylcarbonyl)amino]-4-hydroxyphenoxy}-3,5-dimethylanilino)(oxo)acetate

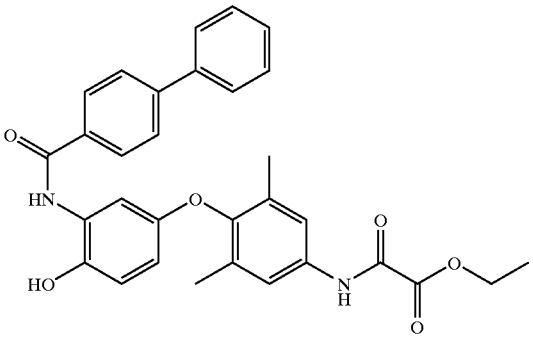

In accordance with the general procedure for preparing the library Ic, the resin 5 is reacted with biphenyl-4-ylcarbonyl chloride as "acid chloride A" and ethoxalyl chloride as "acid chloride B". The resulting crude product is purified by preparative RP-HPLC with a water/acetonitrile eluent.

Yield: 6.4 mg of ethyl (4-{3-[(biphenyl-4-ylcarbonyl)amino]-4-hydroxyphenoxy}-3,5-dimethylanilino)(oxo)acetate ¹H-NMR (200 MHz, CDCl₃): 1.41, t, 3H; 2.13, s, 6H ; 4.42, q, 2H; 6.53, d, 1H; 6.69, dd, 1H; 7.01, d, 1H; 7.34, s, 2H; 7.38–7.75, m, 7H; 7.96, d, 2H; 8.18, s, 1H; 8.80, s, 1H.

MS: 525 [MH⁺].

Example 7

Ethyl (4-{3-[(cyclopropylcarbonyl)amino]-4-hydroxyphenoxy}-3,5-dimethylanilino)(oxo)acetate

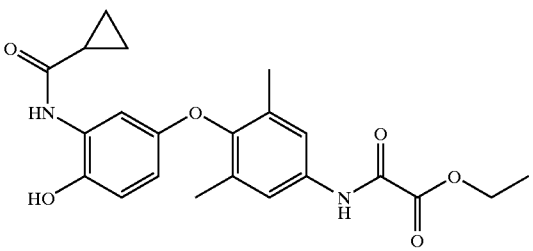

In accordance with the general procedure for preparing the library Ic, the resin 5 is reacted with cyclopropylcarbonyl chloride as "acid chloride A" and ethoxalyl chloride as "acid chlorid B". The resulting crude product is purified by preparative RP-HPLC with a water/acetonitrile eluent.

Yield: 9.0 mg of ethyl (4-{3-[(cyclopropylcarbonyl)amino]-4-hydroxyphenoxy}-3,5-dimethylanilino)(oxo)acetate $^1$H-NMR (200 MHz, CDCl$_3$): 0.83–0.97, m, 2H; 1.05–1.17, m, 2H; 1.41, t, 3H; 1.52–1.68, m, 1H; 2.10, s, 6H; 4.40, q, 2H; 6.27, d, 1H; 6.66, dd, 1H; 6.93, d, 1H; 7.31, s, 2H; 7.93, s, 1H; 8.35, s, 1H.

MS: 413 [MH$^+$].

Example 8

Ethyl (4-{4-hydroxy-3-[(3-phenylpropanoyl)amino]phenoxy}-3,5-dimethylanilino)(oxo)acetate

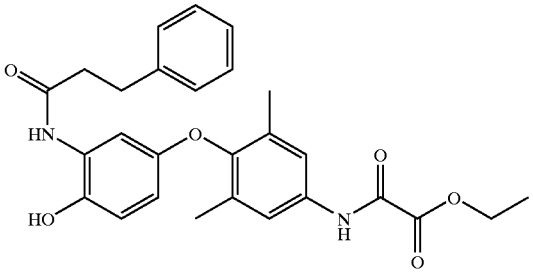

In accordance with the general procedure for preparing the library Ic, the resin 5 is reacted with 3-phenylpropionyl chloride as "acid chloride A" and ethoxalyl chloride as "acid chloride B". The resulting crude product is purified by preparative RP-HPLC with a water/acetonitrile eluent.

Yield: 12.0 mg of ethyl (4-{4-hydroxy-3-[(3-phenylpropanoyl)amino]phenoxy}-3,5-dimethylanilino)(oxo)acetate $^1$H-NMR (200 MHz, CDCl$_3$): 1.38, t, 3H; 2.09, s, 6H ; 2.70, t, 2H; 3.03, t, 2H; 4.39, q, 2H; 6.10, d, 1H; 6.65, dd, 1H; 6.92 d, 1H; 7.12–7.33, m, 5H; 7.32, s, 2H; 7.56, s, 1H; 8.83, s, 1H. MS: 477 [MH$^+$].

Example 9

Ethyl (4-{4-hydroxy-3-[(2-phenylbutanoyl)amino]phenoxy}-3,5-dimethylanilino)(oxo)acetate

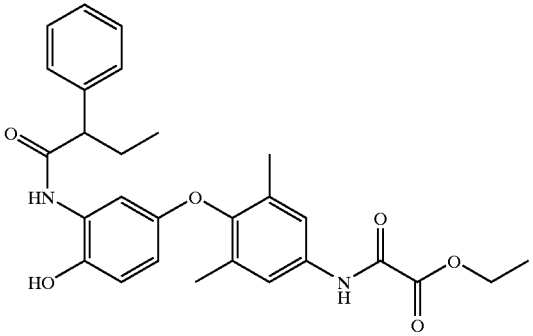

In accordance with the general procedure for preparing the library Ic, 1.5 g (0.13 mmol) of resin 5 are reacted with 2-phenylbutyryl chloride as "acid chloride A" and ethoxalyl chloride as "acid chloride B". The resulting crude product is purified by preparative RP-HPLC with a water/acetonitrile eluent. Yield: 4.2 mg of ethyl (4-{4-hydroxy-3-[(2-phenylbutanoyl)amino]phenoxy}-3,5-dimethylanilino)(oxo)acetate $^1$H-NMR (200 MHz, CDCl$_3$): 0.91, t, 3H; 1.36, t, 3H; 1.73–2.00, m, 1H; 2.08, s, 6 H; 2.12–2.33, m, 1H; 3.46, t, 1H; 4.35, q, 2H; 6.29, d, 1H; 6.55, dd, 1H; 6.89, d, 1H; 7.22–7.40, m, 5H; 7.35, s, 2H; 7.61, s, 1H; 8.23, br s, 1H; 8.80, s, 1H.

MS: 491 [MH$^+$].

Example 10

Ethyl {4-[3-(hexanoylamino)-4-hydroxyphenoxy]-3,5-dimethylanilino}(oxo)acetate

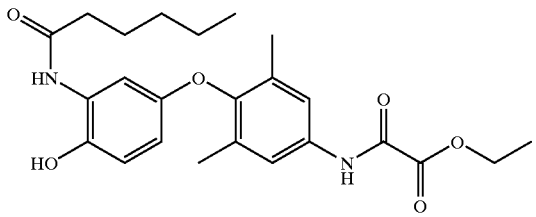

In accordance with the general procedure for preparing the library Ic, 1.5 g (0.13 mmol) of resin 5 are reacted with hexanoyl chloride as "acid chloride A" and ethoxalyl chloride as "acid chloride B". The resulting crude product is purified by preparative RP-HPLC with a water/acetonitrile eluent.

Yield: 8.6 mg of ethyl {4-[3-(hexanoylamino)-4-hydroxyphenoxy]-3,5-dimethylanilino}(oxo)acetate $^1$H-NMR (200 MHz, CDCl$_3$): 0,89, t, 3H; 1.22–1.42, m, 4H; 1.40, t, 3H; 1.60–1.80, m, 2H; 2.10, s, 6H ; 2.38, t, 2H; 4.40, q, 2H; 6.29, d, 1H; 6.66, dd, 1H; 6.93, d, 1H; 7.31, s, 2H; 7.72, s, 1H; 8.4, br s, 1H; 8.84, s, 1H.

MS: 443 [MH$^+$].

Example 11

Ethyl (4-{4-hydroxy-3-[(2-propylpentanoyl)amino]phenoxy}-3,5-dimethylanilino)(oxo)acetate

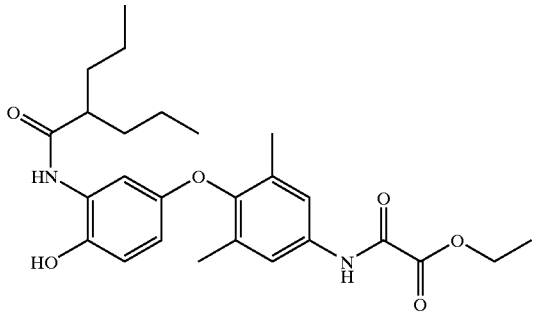

In accordance with the general procedure for preparing the library Ic, 1.5 g (0.13 mmol) of resin 5 are reacted with 2-propylpentanoyl chloride as "acid chloride A" and ethoxalyl chloride as "acid chloride B". The resulting crude product is purified by preparative RP-HPLC with a water/acetonitrile eluent.

Yield: 11.5 mg of ethyl (4-{4-hydroxy-3-[(2-propylpentanoyl)amino]phenoxy}-3,5-dimethylanilino)(oxo)acetate $^1$H-NMR (200 MHz, CDCl$_3$): 0,90, t, 6H ; 1.20–1.80, m, 8H; 1.37, t, 3H; 2.23–2.43, m, 1H; 4.38, q, 2H; 6.32, d, 1H; 6.63, dd, 1H; 6.93, d, 1H; 7.32, s, 2H; 7.85, s, 1H; 8.85, s, 1H.

MS: 471 [MH$^+$].

Example 12

Ethyl (4-{4-hydroxy-3-[(methoxyacetyl)amino]phenoxy}-3,5-dimethylanilino)(oxo)acetate

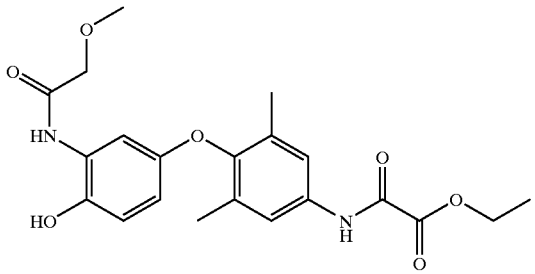

In accordance with the general procedure for preparing the library Ic, 1.5 g (0.13 mmol) of resin 5 are reacted with methoxyacetyl chloride as "acid chloride A" and ethoxalyl chloride as "acid chloride B". The resulting crude product is purified by preparative RP-HPLC with a water/acetonitrile eluent.

Yield: 13.7 mg of ethyl (4-{4-hydroxy-3-[(methoxyacetyl)amino]phenoxy}-3,5-dimethylanilino)(oxo)acetate $^1$H-NMR (200 MHz, CDCl$_3$): 1.44, t, 3H; 2.12, s, 6H ; 3.51, s, 3H; 4.16, s, 2H; 4.42, q, 2H; 6.39, d, 1H; 6.61, dd, 1H; 6.93, d, 1H; 7.38, s, 2H; 8.28, s, 1H; 8.38, s, 1H; 8.80, s, 1H.

MS:417[MH$^+$].

Example 13

N-{5-[4-(Acetylamino)-2,6-dimethylphenoxy]-2-hydroxyphenyl}-2-phenoxybutanamide

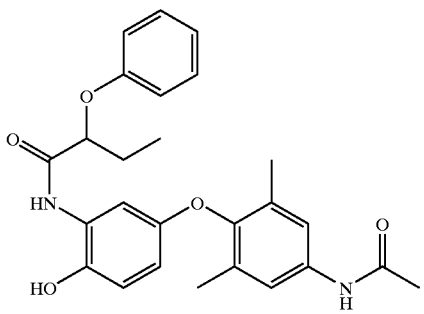

In accordance with the general procedure for preparing the library Ic, the resin 5 is reacted with 2-phenoxybutyryl chloride as "acid chloride A" and acetyl chloride as "acid chloride B". The resulting crude product is purified by preparative RP-HPLC with a water/acetonitrile eluent.

Yield: 11.3 mg of N-{5-[4-(acetylamino)-2,6-dimethylphenoxy]-2-hydroxyphenyl}-2-phenoxybutanamide $^1$H-NMR (200 MHz, CDCl$_3$): 1.08, t, 3H; 1.98–2.10, m, 2H; 2.05, s, 6H ; 2.13, s, 3 H; 4.70, dd, 1H; 6.47–6.57, m, 2H; 6.83–7.40, m, 8H; 7.97, s, 1H; 8.52, s, 1H.

MS: 449 [MH$^+$].

Example 14

Ethyl {4-[4-hydroxy-3-({[(1-phenylethyl)amino]carbonyl}amino)phenoxy]-3,5-dimethylanilino}(oxo)acetate

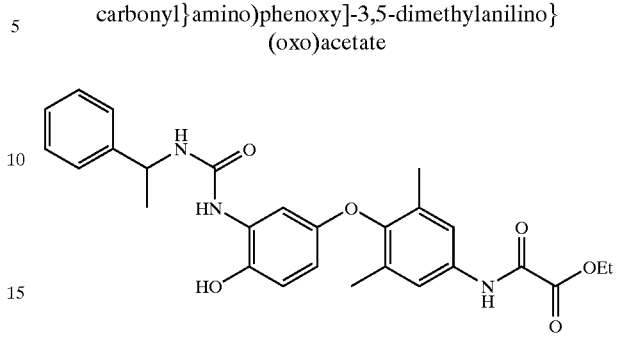

In accordance with the general procedure for preparing the library Ic, the resin resin 5 is reacted with 1-phenylethylamine as "amine A" and ethoxalyl chloride as "acid chloride B". The resulting crude product is purified by preparative RP-HPLC with a water/acetonitrile eluent.

Yield: 9.0mg of ethyl {4-[4-hydroxy-3-({[(l-phenylethyl)amino]carbonyl}amino)phenoxy]-3,5-dimethylanilino}(oxo)acetate $^1$H-NMR (200 MHz, CDCl$_3$): 1.41, t, 3H; 1.46, t, 3H; 2.03, s, 6H ; 4.41, q, 2H; 4.82, dq, 1H; 5.32, d, 1H; 5.95, d, 1H; 6.53, dd, 1H; 6.6, s, 1H; 6.85, d, 1H; 7.20–7.40, m, 7H; 8.88, s, 1H.

MS: 492 [MH$^+$].

Example 15

Ethyl [4-(3-{[(cyclohexylmethyl)amino]carbonyl}-4-hydroxyphenoxy)-3,5-dimethylanilino](oxo)acetate

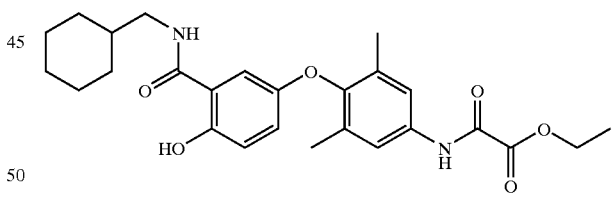

In analogy to the general procedure for preparing the library Id, 2.00 g of of resin 10 are reacted with (cyclohexylmethyl)amine as "amine A" and ethoxalyl chloride as "acid chloride B". The resulting crude product is purified by preparative RP-HPLC with a water/acetonitrile eluent.

Yield: 95 mg of ethyl [4-(3-{[(cyclohexylmethyl)amino]carbonyl}-4-hydroxyphenoxy)-3,5-dimethylanilino](oxo)acetate $^1$H-NMR (200 MHz, CDCl$_3$): 0.85–1.83, m, 11H; 1.44, t, 3H; 2.14, s, 6H ; 3.27, t, 2H; 4.42, q, 1H; 6.29, t, 1H; 6.70–6.92, m, 3H; 7.40, s, 2H; 8.80, s, 1H.

Example 16

Ethyl [4-(3-{[cyclohexyl(methyl)amino]carbonyl}-4-hydroxyphenoxy)-3,5-dimethylanilino](oxo)acetate

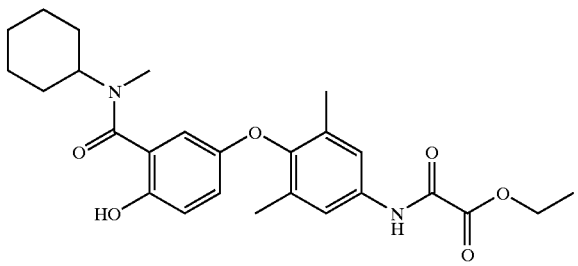

In analogy to the general procedure for preparing the library Id, 2.00 g of of resin 10 are reacted with cyclohexyl (methyl)amine as "amine A" and ethoxalyl chloride as "acid chloride B". The resulting crude product is purified by preparative RP-HPLC with a water/acetonitrile eluent.

Yield: 30 mg of ethyl [4-(3-{[cyclohexyl(methyl)amino] carbonyl}-4-hydroxyphenoxy)-3,5-dimethylanilino](oxo) acetate $^1$H-NMR (200 MHz, CDCl$_3$): 0.95–1.83, m, 10H ; 1.44, t, 3H; 2.12, s, 6H ; 2.89, s, 3H; 4.42, q, 1H; 6.50, d, 1H; 6.86, dd, 1H; 6.93, d, 1H; 7.39, s, 2H; 8.80, s, 1H.

The compounds listed below are prepared in accordance with the general procedures for libraries Ia–Id.

Analytical Parameters

All the products are characterized by LC-MS. The standard separation system used for this is as follows: HP 1100 with UV detector (208–400 nm), 40° C. oven temperature, Waters-Symmetry C18 column (50 mm×2.1 mm, 3,5 μm), mobile phase A: 99.9% acetonitrile/0.1% formic acid, mobile phase B: 99.9% water/0.1% formic acid; gradient:

| Time (min) | A: % | B: % | Flow rate (ml/min) |
|---|---|---|---|
| 0.00 | 10.0 | 90.0 | 0.50 |
| 4.00 | 90.0 | 10.0 | 0.50 |
| 6.00 | 90.0 | 10.0 | 0.50 |
| 6.10 | 10.0 | 90.0 | 1.00 |
| 7.50 | 10.0 | 90.0 | 0.50 |

The substances were detected using a Micromass Quattro LCZ MS, ionization: ESI positive/negative.

| Ex. No. | Structure | MW [g/mol] calculated | Retention time [min] | MW [g/mol] found |
|---|---|---|---|---|
| 17 | 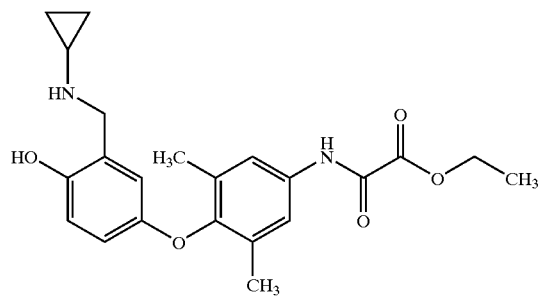 | 398.5 | 2.64 | 398.2 |
| 18 | 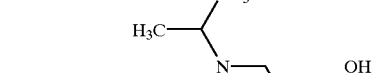 | 428.5 | 2.78 | 428.2 |

-continued

| Ex. No. | Structure | MW [g/mol] calculated | Retention time [min] | MW [g/mol] found |
|---|---|---|---|---|
| 19 | 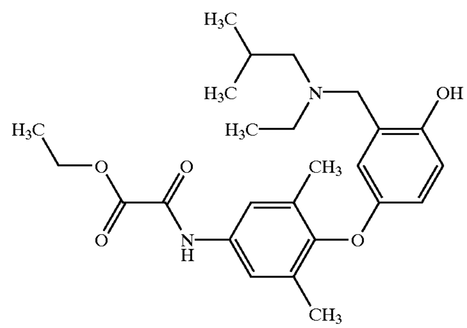 | 442.6 | 2.90 | 442.2 |
| 20 | 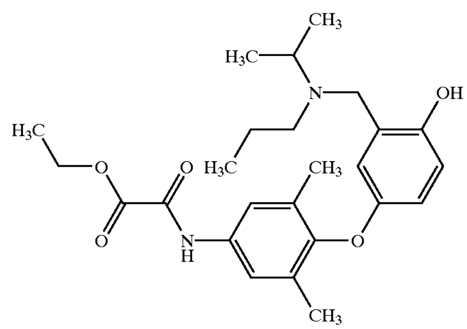 | 442.6 | 2.88 | 442.2 |
| 21 | 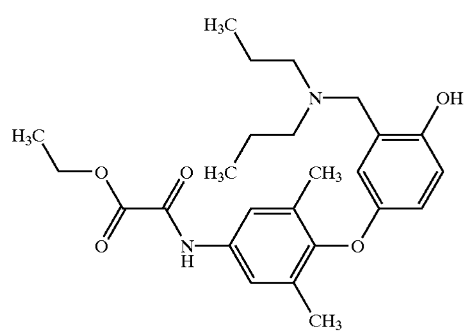 | 442.6 | 2.93 | 442.2 |
| 22 | 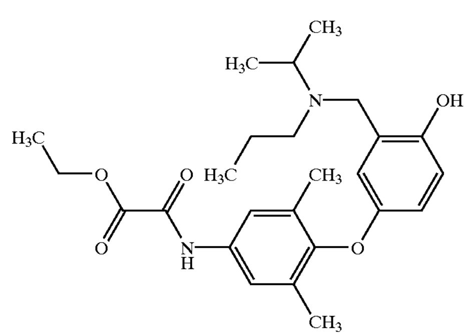 | 442.6 | 3.36 | 442.2 |

-continued

| Ex. No. | Structure | MW [g/mol] calculated | Retention time [min] | MW [g/mol] found |
|---|---|---|---|---|
| 23 | 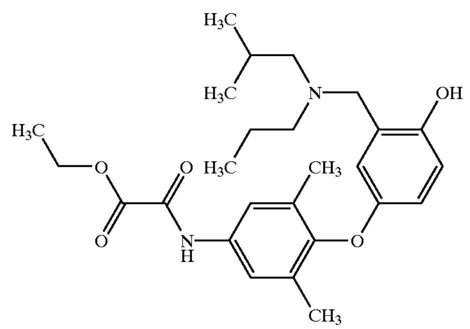 | 456.6 | 2.99 | 456.3 |
| 24 | 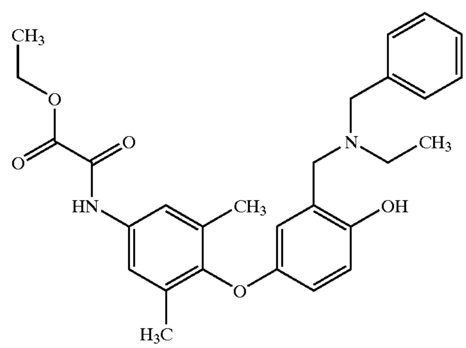 | 476.6 | 3.01 | 476.2 |
| 25 | 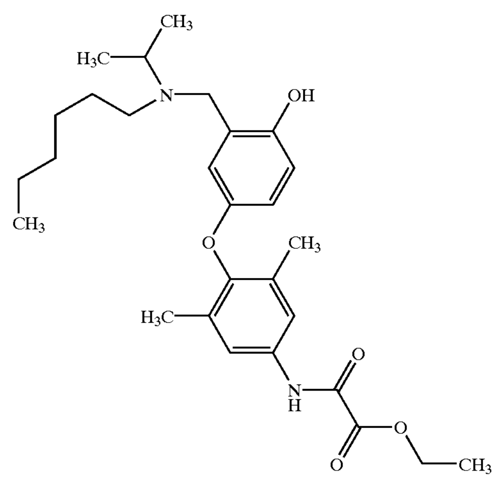 | 484.6 | 3.23 | 484.3 |
| 26 | 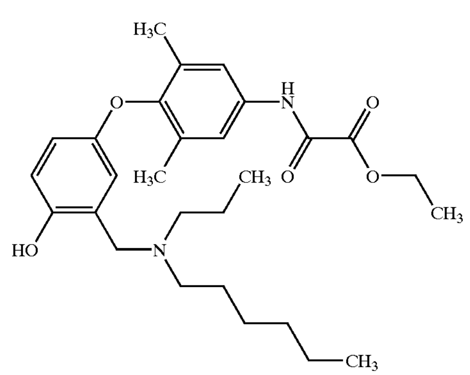 | 484.6 | 3.28 | 484.3 |

-continued

| Ex. No. | Structure | MW [g/mol] calculated | Retention time [min] | MW [g/mol] found |
|---------|-----------|----------------------|---------------------|------------------|
| 27 | 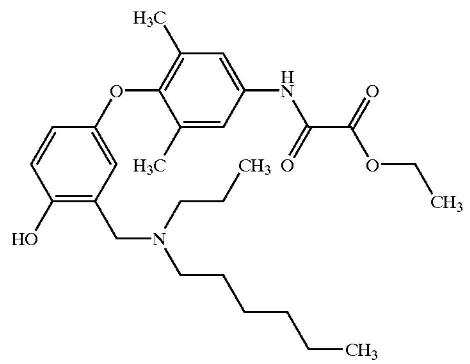 | 484.6 | 3.28 | 484.3 |
| 28 | 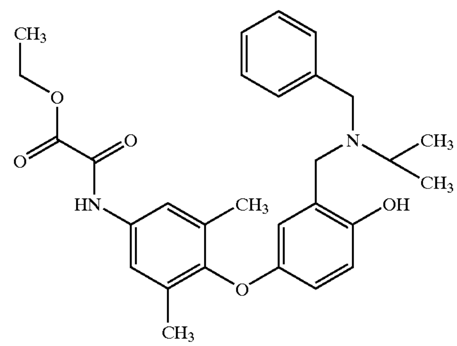 | 490.6 | 3.08 | 490.2 |
| 29 | 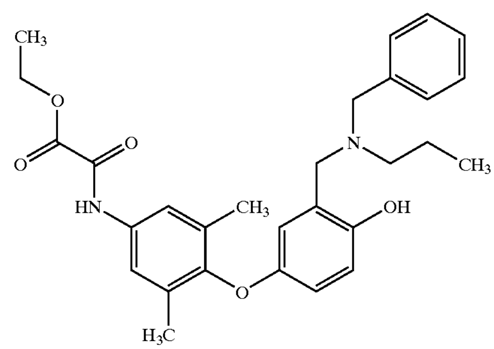 | 490.6 | 3.13 | 490.2 |
| 30 | 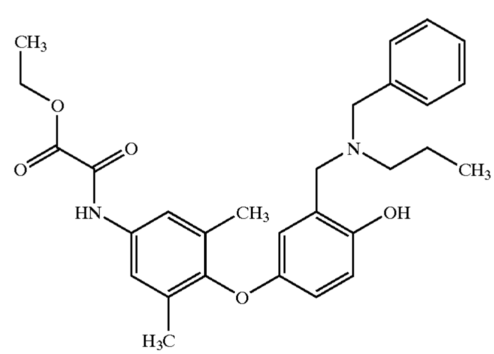 | 490.6 | 3.13 | 490.2 |

-continued

| Ex. No. | Structure | MW [g/mol] calculated | Retention time [min] | MW [g/mol] found |
|---------|-----------|----------------------|----------------------|------------------|
| 31 | 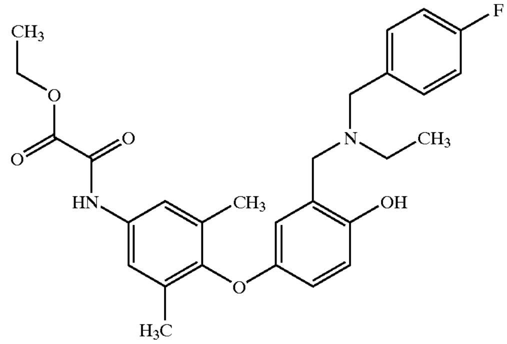 | 494.6 | 3.06 | 494.2 |
| 32 | 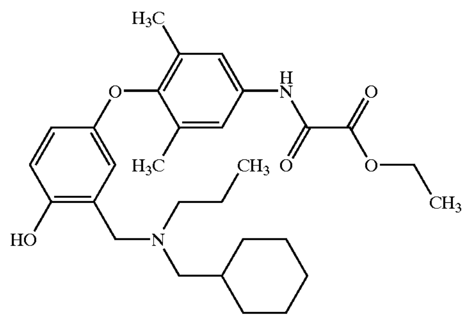 | 496.7 | 3.66 | 496.3 |
| 33 | 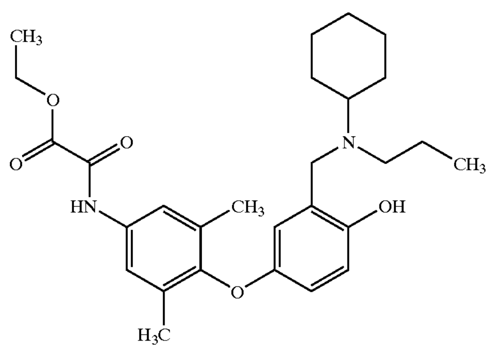 | 496.7 | | 496.3 |
| 34 | 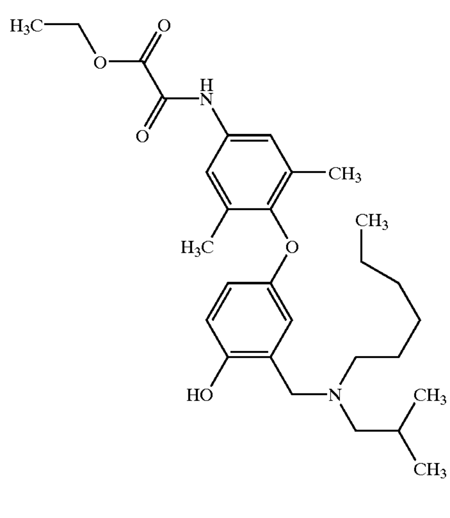 | 498.7 | 3.34 | 498.3 |

-continued

| Ex. No. | Structure | MW [g/mol] calculated | Retention time [min] | MW [g/mol] found |
|---|---|---|---|---|
| 35 | 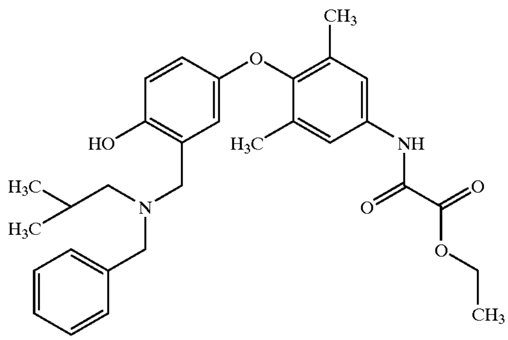 | 504.6 | 3.34 | 504.3 |
| 36 | 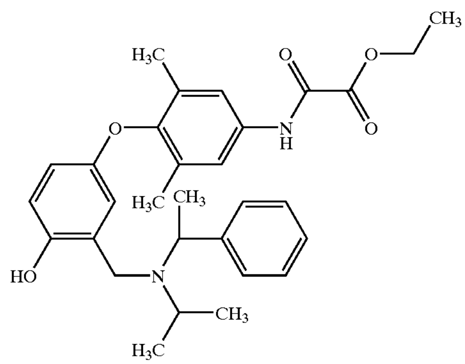 | 504.6 | 3.59 | 504.3 |
| 37 | 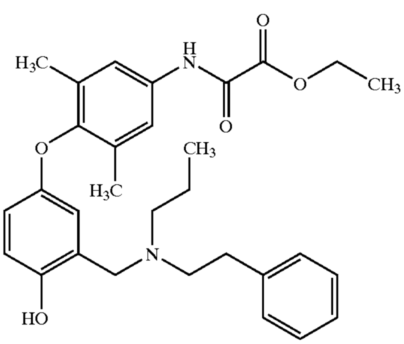 | 504.6 | 3.17 | 504.3 |
| 38 | 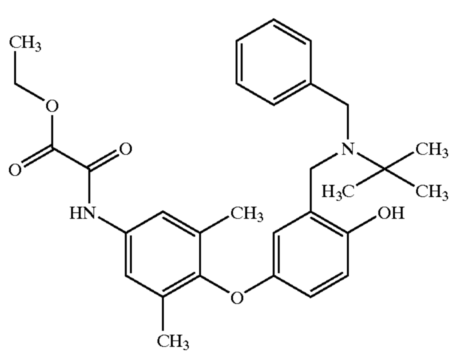 | 504.6 | 3.08 | 504.3 |

-continued

| Ex. No. | Structure | MW [g/mol] calculated | Retention time [min] | MW [g/mol] found |
|---|---|---|---|---|
| 39 | 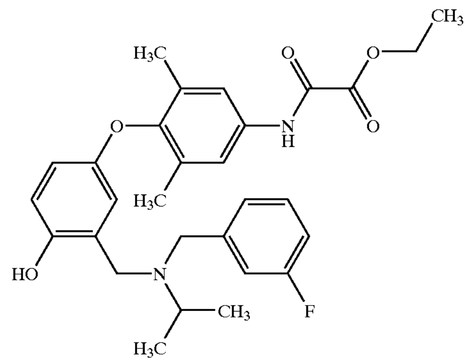 | 508.6 | 3.61 | 508.2 |
| 40 | 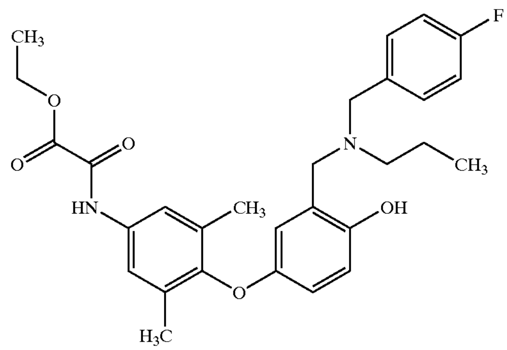 | 508.6 | 3.19 | 508.2 |
| 41 | 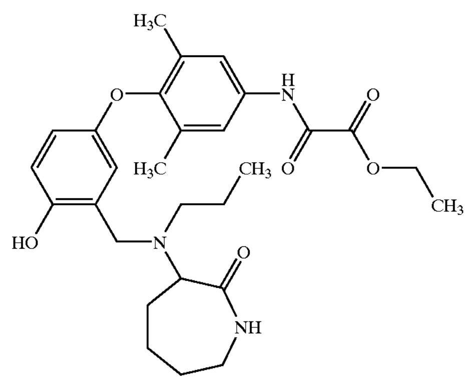 | 511.6 | 3.35 | 511.3 |
| 42 | 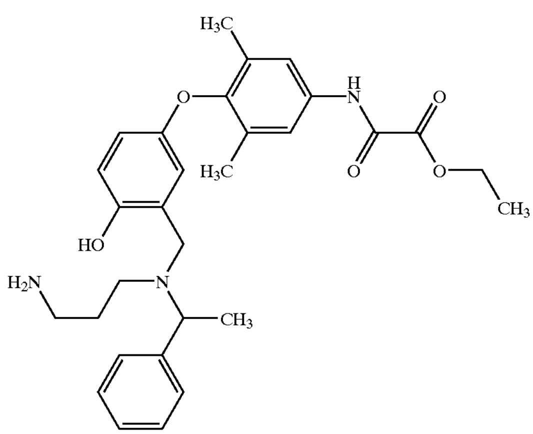 | 519.6 | 3.05 | 519.3 |

-continued

| Ex. No. | Structure | MW [g/mol] calculated | Retention time [min] | MW [g/mol] found |
|---|---|---|---|---|
| 43 | 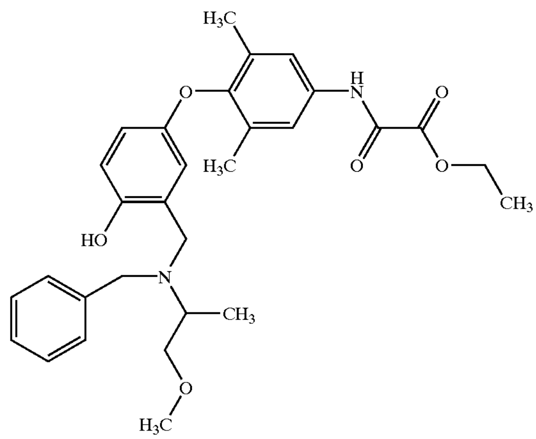 | 520.6 | 3.56 | 520.3 |
| 44 | 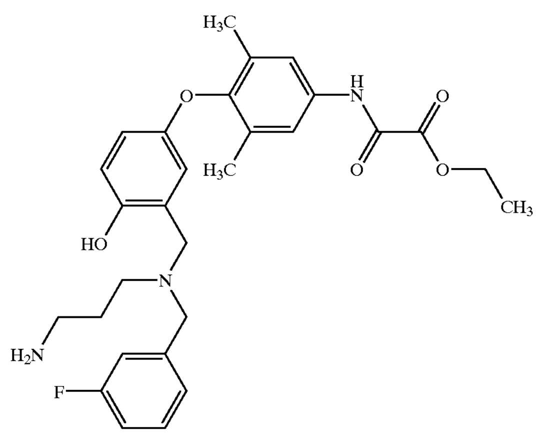 | 523.6 | 3.11 | 523.2 |
| 45 | 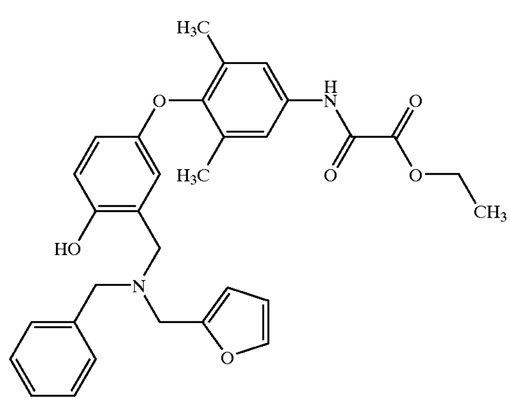 | 528.6 | 4.08 | 528.2 |

-continued

| Ex. No. | Structure | MW [g/mol] calculated | Retention time [min] | MW [g/mol] found |
|---|---|---|---|---|
| 46 | 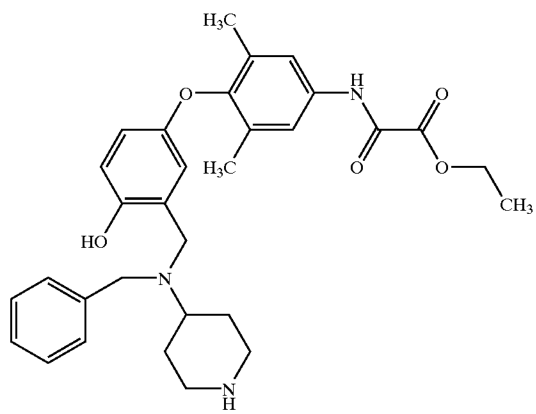 | 531.7 | 3.19 | 531.3 |
| 47 | 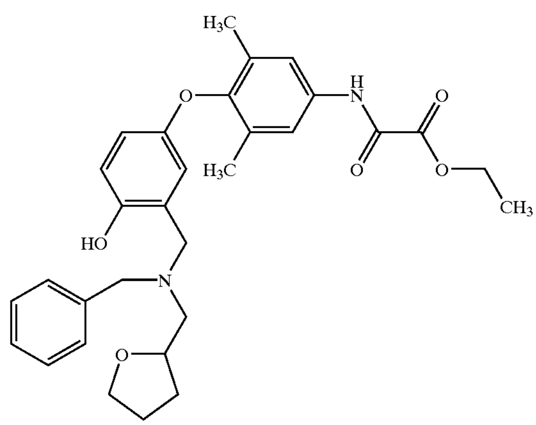 | 532.6 | 5.39 | 532.3 |
| 48 | 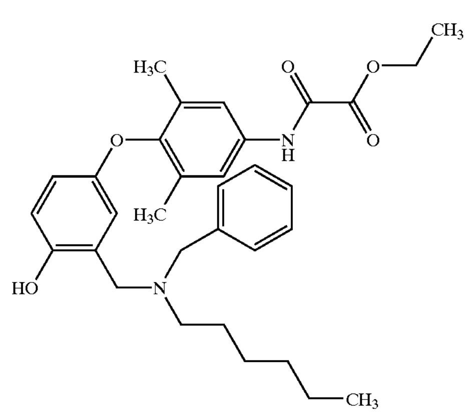 | 532.7 | 3.51 | 532.3 |

-continued

| Ex. No. | Structure | MW [g/mol] calculated | Retention time [min] | MW [g/mol] found |
|---|---|---|---|---|
| 49 | 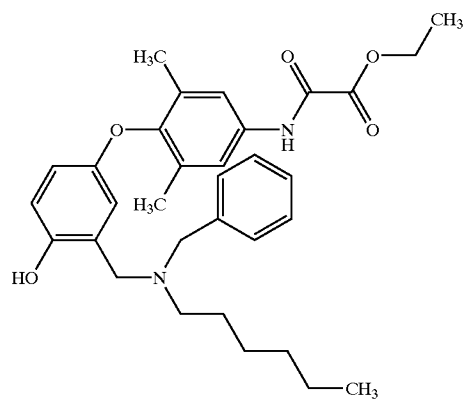 | 532.7 | 3.51 | 532.3 |
| 50 | 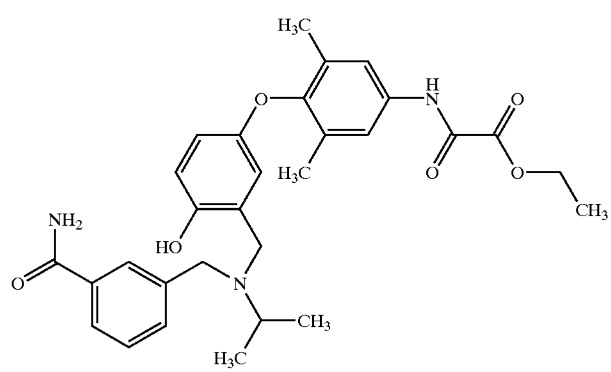 | 533.6 | 3.29 | 533.3 |
| 51 | 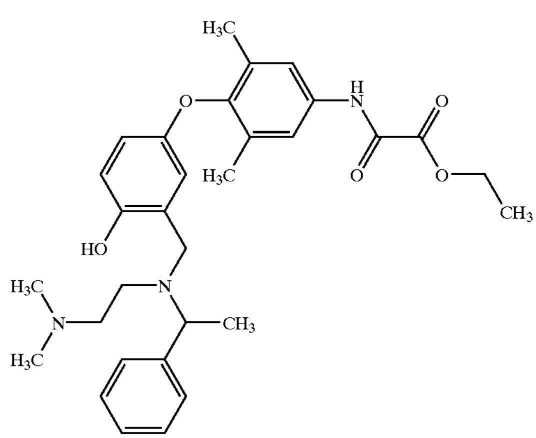 | 533.7 | 3.84 | 533.3 |

| Ex. No. | Structure | MW [g/mol] calculated | Retention time [min] | MW [g/mol] found |
|---|---|---|---|---|
| 52 | 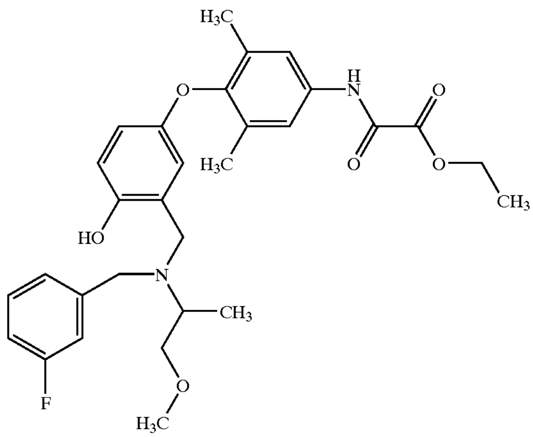 | 538.6 | 3.70 | 538.2 |
| 53 | 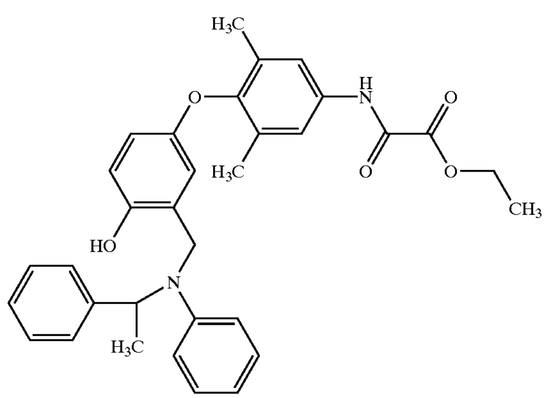 | 538.6 | 5.42 | 538.2 |
| 54 | 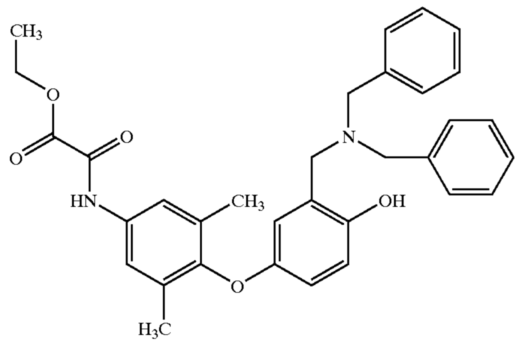 | 538.6 | 3.89 | 538.2 |

-continued
| Ex. No. | Structure | MW [g/mol] calculated | Retention time [min] | MW [g/mol] found |
|---|---|---|---|---|
| 55 | 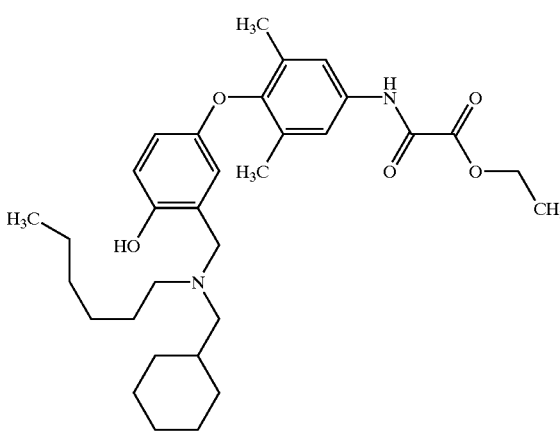 | 538.7 | 3.94 | 538.3 |
| 56 | 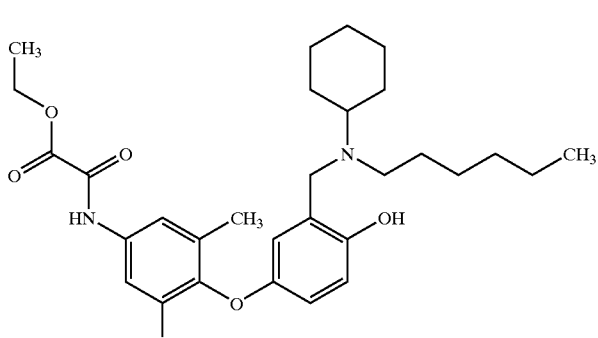 | 538.7 | | 538.3 |
| 57 | 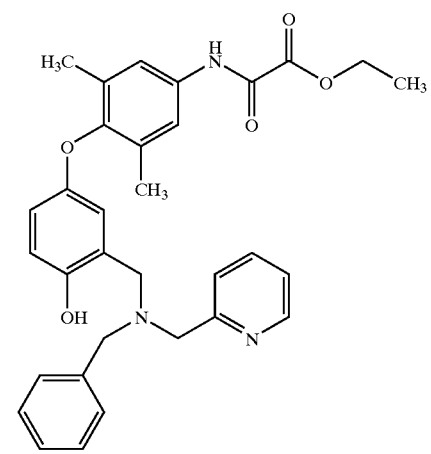 | 539.6 | 3.73 | 539.2 |

-continued

| Ex. No. | Structure | MW [g/mol] calculated | Retention time [min] | MW [g/mol] found |
|---|---|---|---|---|
| 58 | 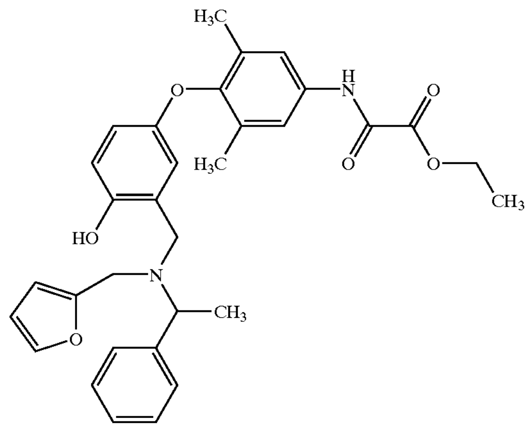 | 542.6 | 4.19 | 542.2 |
| 59 | 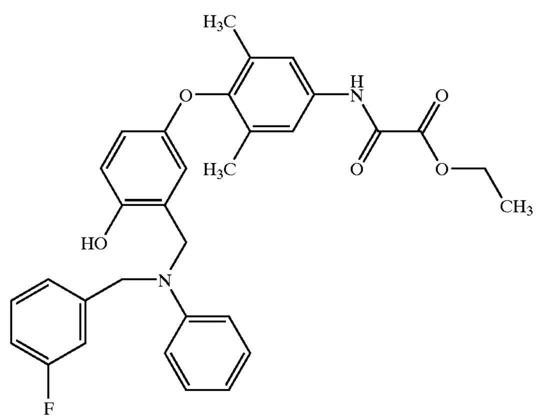 | 542.6 | 5.47 | 542.2 |
| 60 | 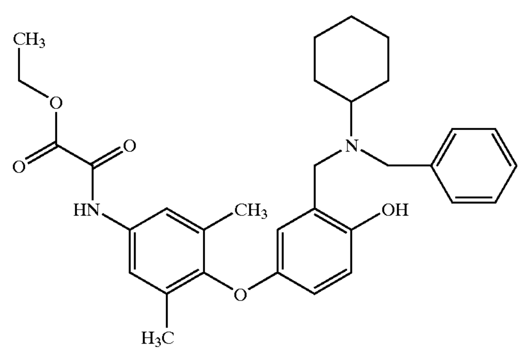 | 544.7 | | 544.3 |

-continued

| Ex. No. | Structure | MW [g/mol] calculated | Retention time [min] | MW [g/mol] found |
|---|---|---|---|---|
| 61 | 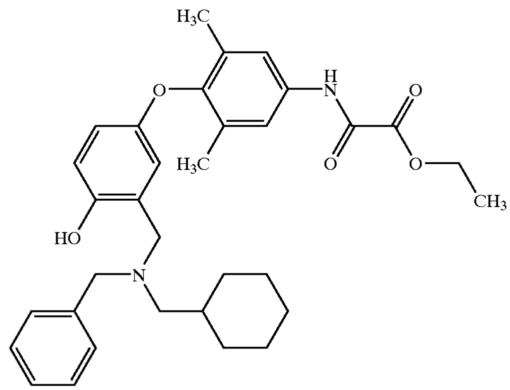 | 544.7 | 3.98 | 544.3 |
| 62 | 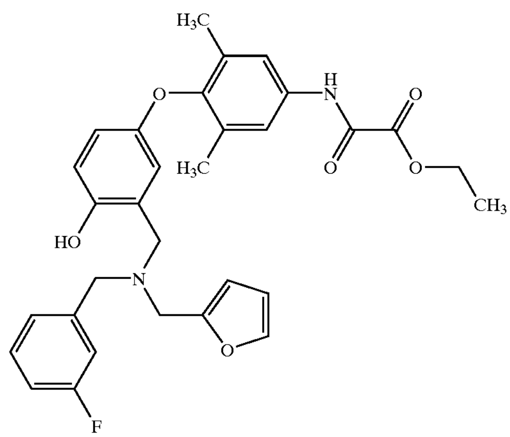 | 546.6 | 4.45 | 546.2 |
| 63 | 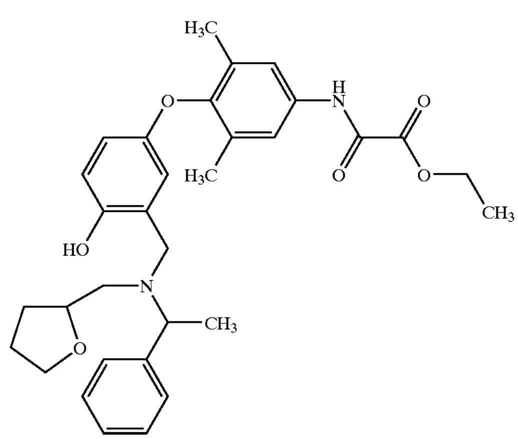 | 546.7 | 5.41 | 546.3 |

-continued

| Ex. No. | Structure | MW [g/mol] calculated | Retention time [min] | MW [g/mol] found |
|---|---|---|---|---|
| 64 | 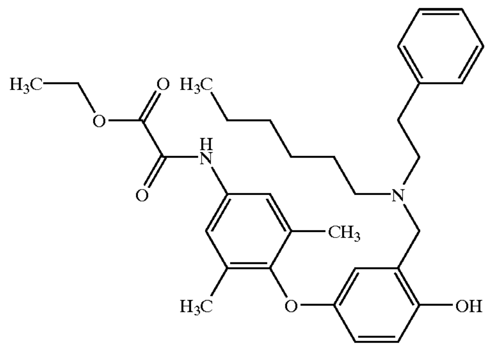 | 546.7 | 3.49 | 546.3 |
| 65 | 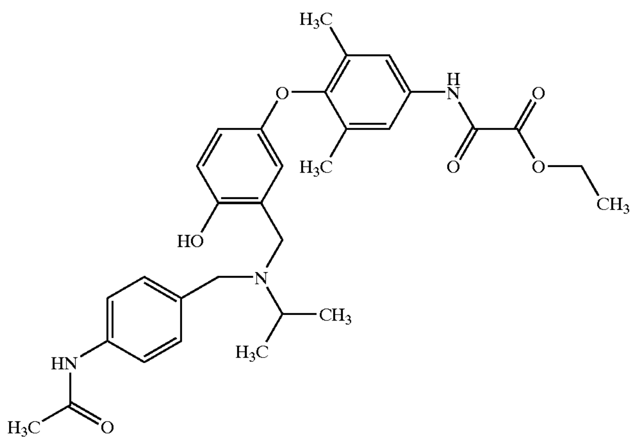 | 547.7 | 3.40 | 547.3 |
| 66 | 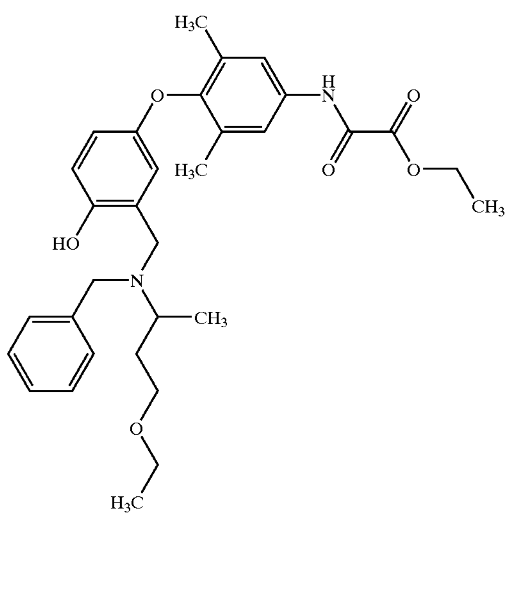 | 548.7 | 3.64 | 548.3 |

-continued

| Ex. No. | Structure | MW [g/mol] calculated | Retention time [min] | MW [g/mol] found |
|---|---|---|---|---|
| 67 | 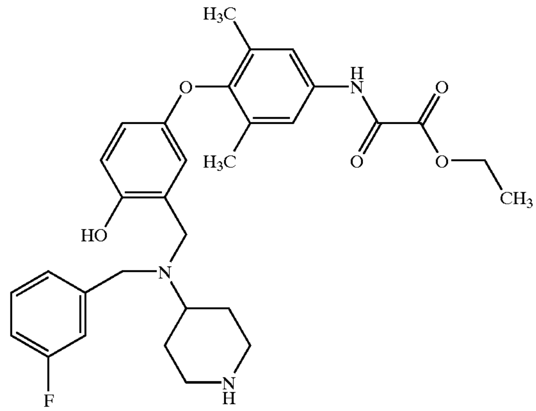 | 549.6 | 3.34 | 549.3 |
| 68 | 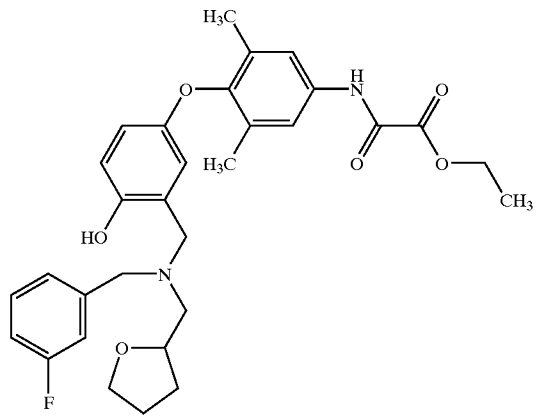 | 550.6 | 5.55 | 550.2 |
| 69 | 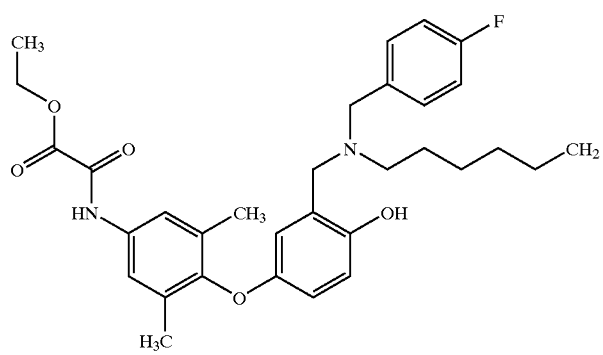 | 550.7 | 3.57 | 550.3 |
| 70 | 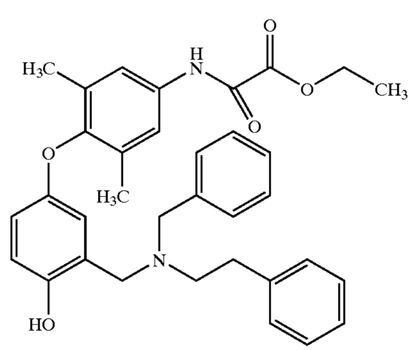 | 552.7 | 3.49 | 552.3 |

-continued

| Ex. No. | Structure | MW [g/mol] calculated | Retention time [min] | MW [g/mol] found |
|---|---|---|---|---|
| 71 | 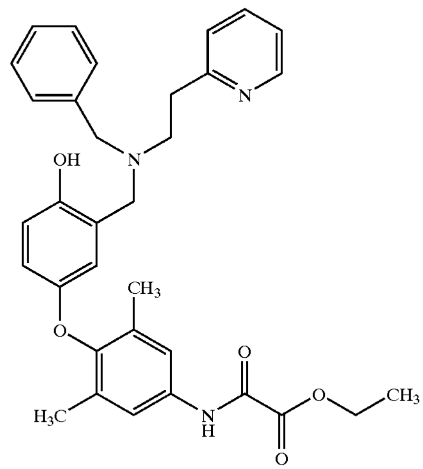 | 553.7 | 3.60 | 553.3 |
| 72 | 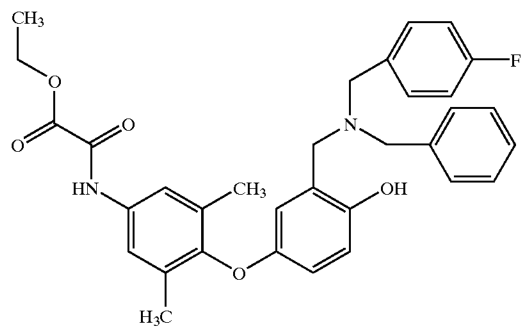 | 556.6 | 4.01 | 556.2 |
| 73 | 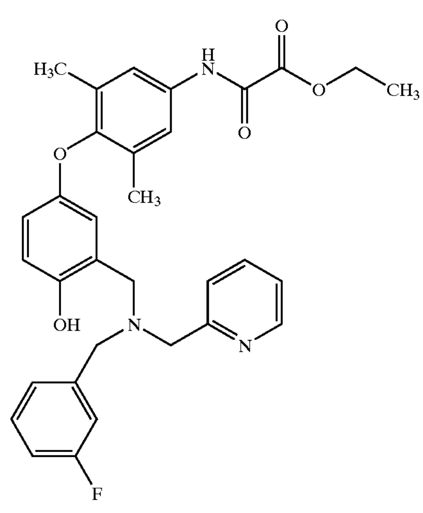 | 557.6 | 3.96 | 557.2 |

-continued

| Ex. No. | Structure | MW [g/mol] calculated | Retention time [min] | MW [g/mol] found |
|---|---|---|---|---|
| 74 | 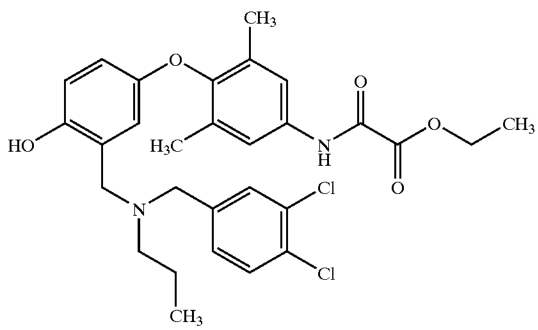 | 559.5 | 3.64 | 558.2 |
| 75 | 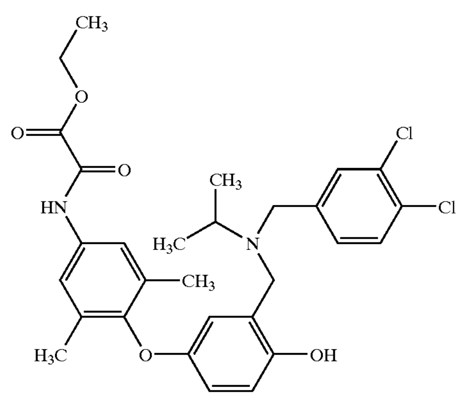 | 559.5 | 3.54 | 558.2 |
| 76 | 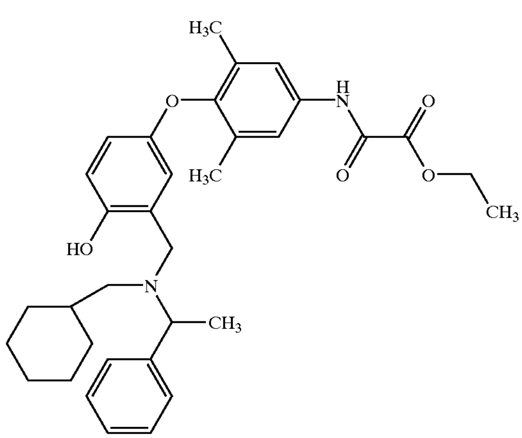 | 558.7 | 3.95 | 558.3 |

-continued

| Ex. No. | Structure | MW [g/mol] calculated | Retention time [min] | MW [g/mol] found |
|---------|-----------|----------------------|----------------------|------------------|
| 77 | 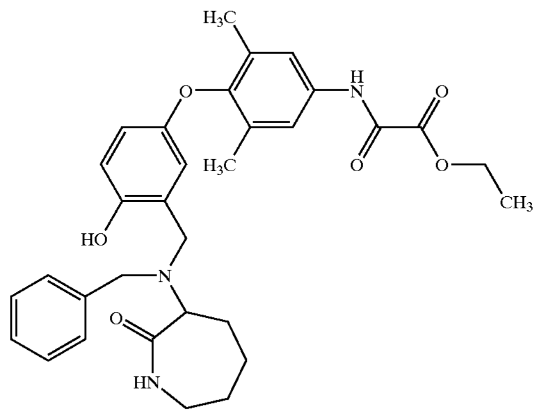 | 559.7 | 3.69 | 559.3 |
| 78 | 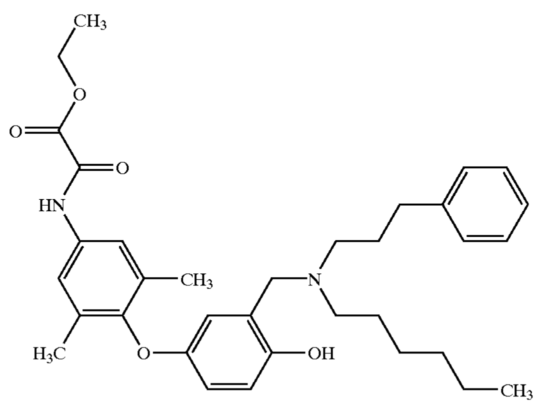 | 560.7 | 3.53 | 560.3 |
| 79 | 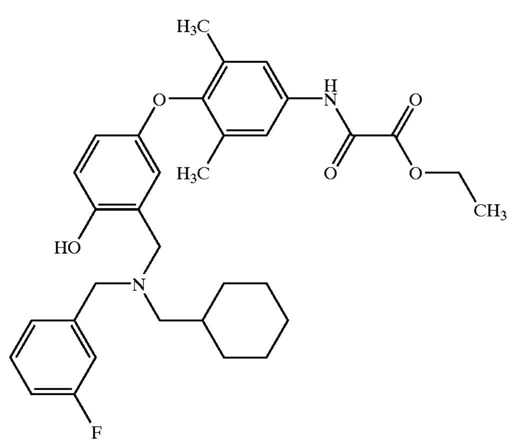 | 562.7 | 4.23 | 562.3 |

-continued
| Ex. No. | Structure | MW [g/mol] calculated | Retention time [min] | MW [g/mol] found |
|---|---|---|---|---|
| 80 | 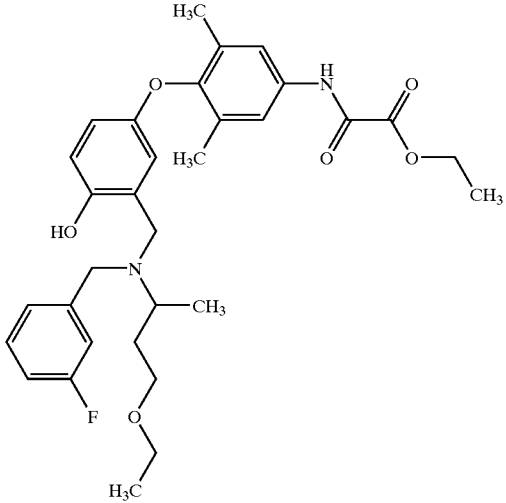 | 566.7 | 3.70 | 566.3 |
| 81 | 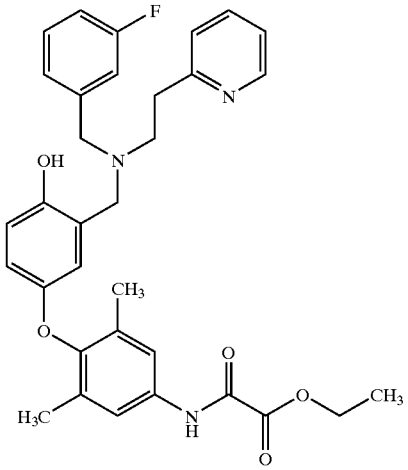 | 571.7 | 3.65 | 571.2 |
| 82 | 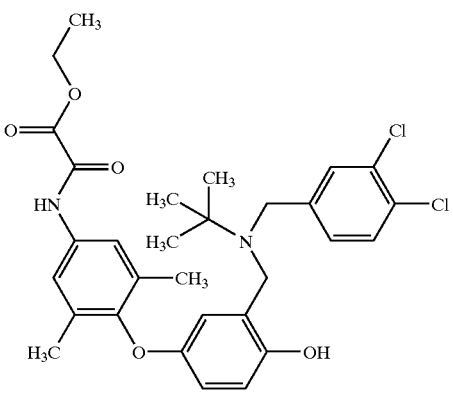 | 573.5 | 3.47 | 572.2 |

-continued

| Ex. No. | Structure | MW [g/mol] calculated | Retention time [min] | MW [g/mol] found |
|---|---|---|---|---|
| 83 | 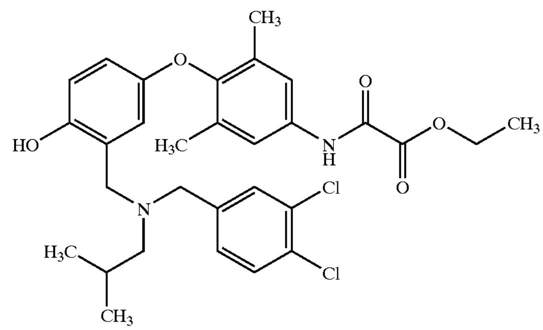 | 573.5 | 4.23 | 572.2 |
| 84 | 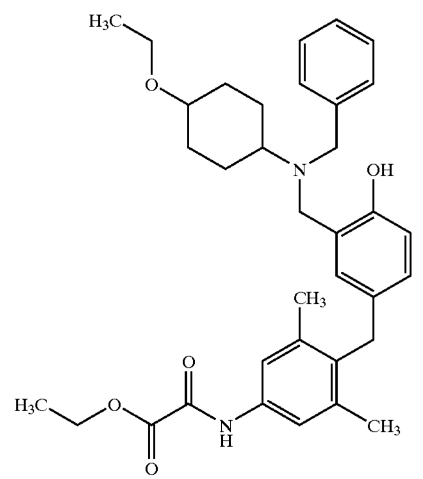 | 574.7 | 3.73 | 574.3 |
| 85 | 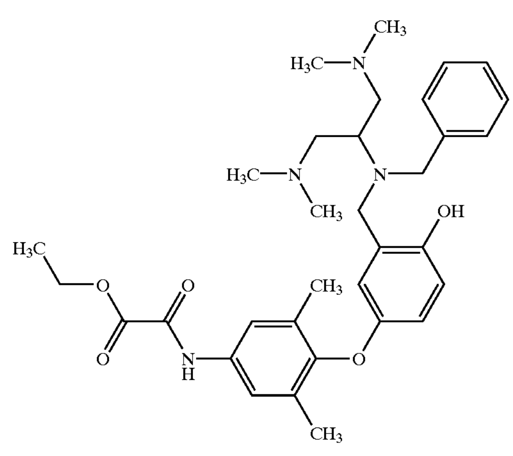 | 576.7 | 3.15 | 576.3 |

-continued

| Ex. No. | Structure | MW [g/mol] calculated | Retention time [min] | MW [g/mol] found |
|---|---|---|---|---|
| 86 | 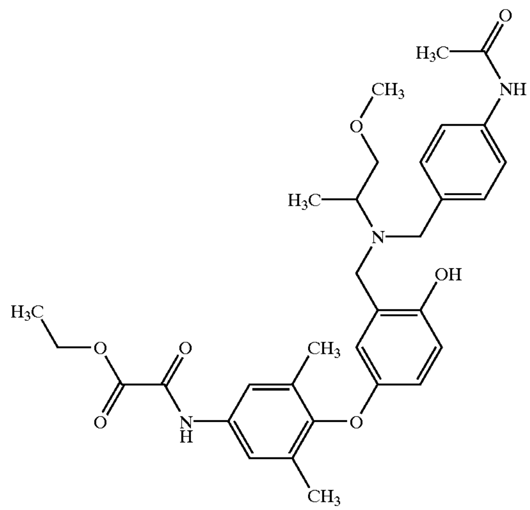 | 577.7 | 3.42 | 577.3 |
| 87 | 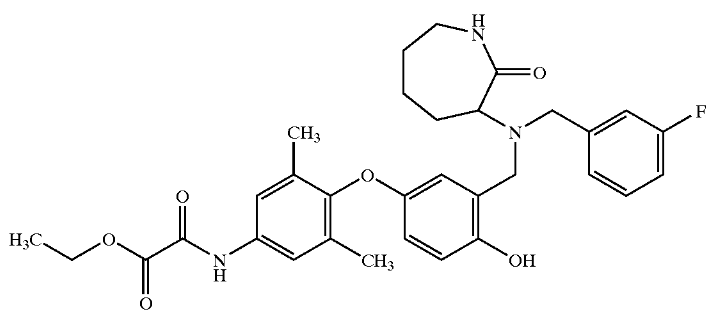 | 577.7 | 4.00 | 577.3 |
| 88 | 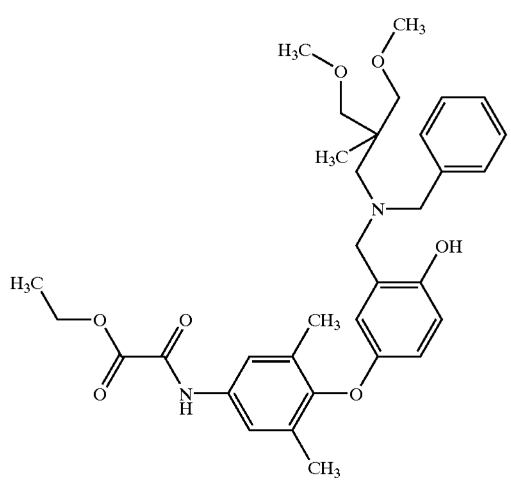 | 578.7 | 3.69 | 578.3 |

| Ex. No. | Structure | MW [g/mol] calculated | Retention time [min] | MW [g/mol] found |
|---|---|---|---|---|
| 89 | 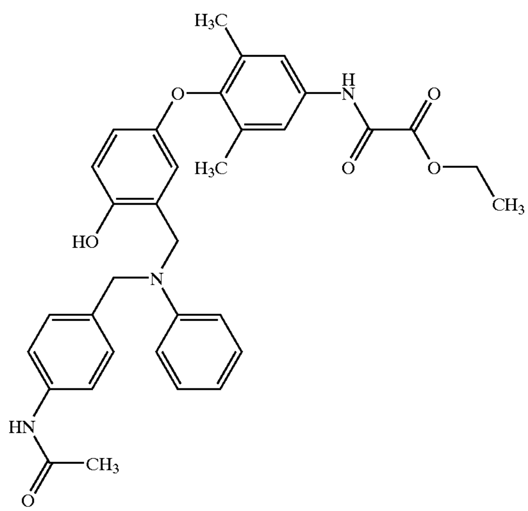 | 581.7 | 4.77 | 581.3 |
| 90 | 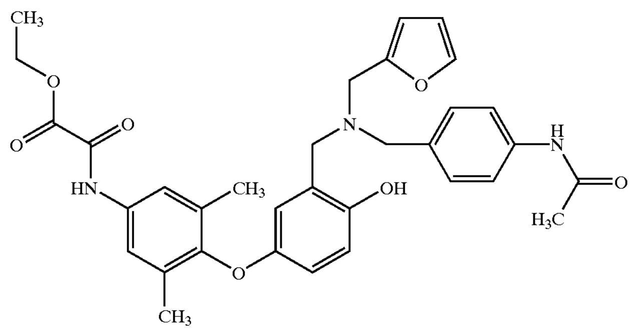 | 585.7 | 3.64 | 585.2 |
| 91 | 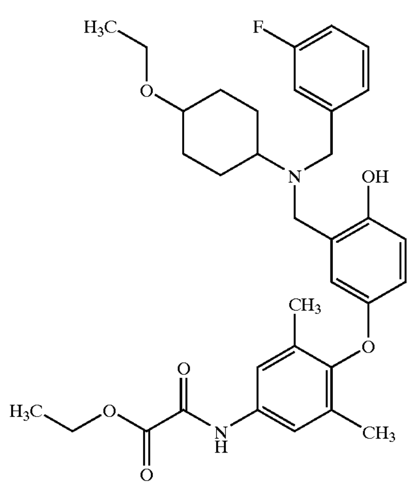 | 592.7 | 3.86 | 592.3 |

-continued

| Ex. No. | Structure | MW [g/mol] calculated | Retention time [min] | MW [g/mol] found |
|---|---|---|---|---|
| 92 | 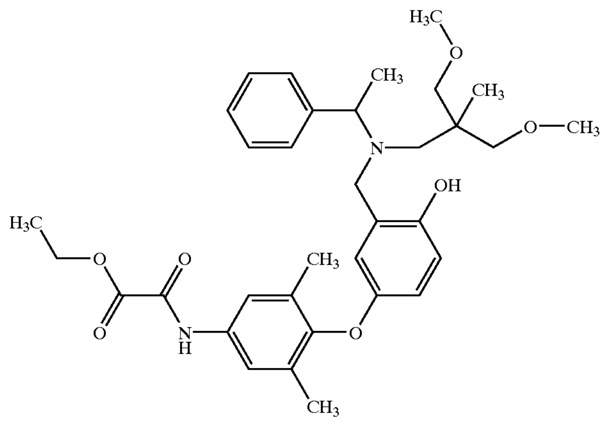 | 592.7 | 3.74 | 592.3 |
| 93 | 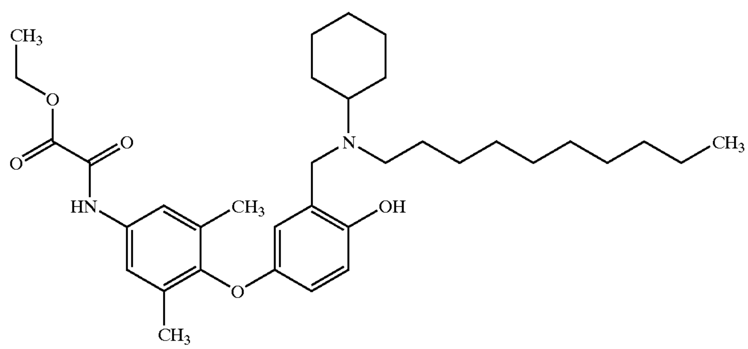 | 594.8 | | 594.4 |
| 94 | 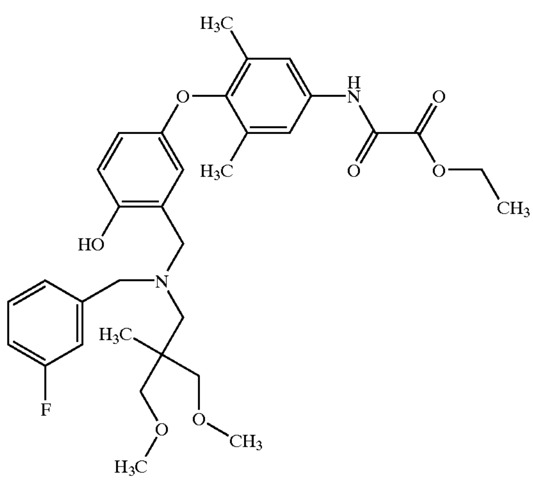 | 596.7 | 3.77 | 596.3 |

| Ex. No. | Structure | MW [g/mol] calculated | Retention time [min] | MW [g/mol] found |
|---|---|---|---|---|
| 95 | 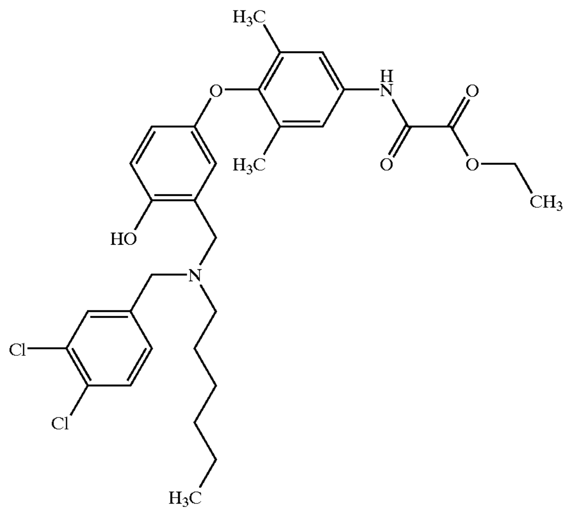 | 601.6 | 4.15 | 600.2 |
| 96 | 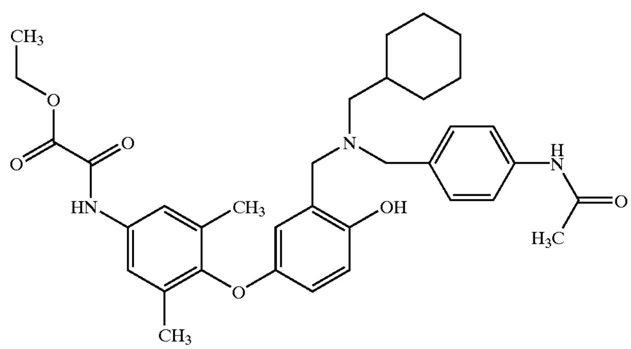 | 601.7 | 3.71 | 601.3 |
| 97 | 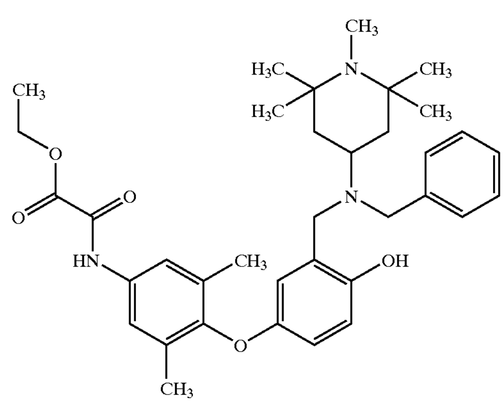 | 601.8 | | 601.4 |

| Ex. No. | Structure | MW [g/mol] calculated | Retention time [min] | MW [g/mol] found |
| --- | --- | --- | --- | --- |
| 98 | 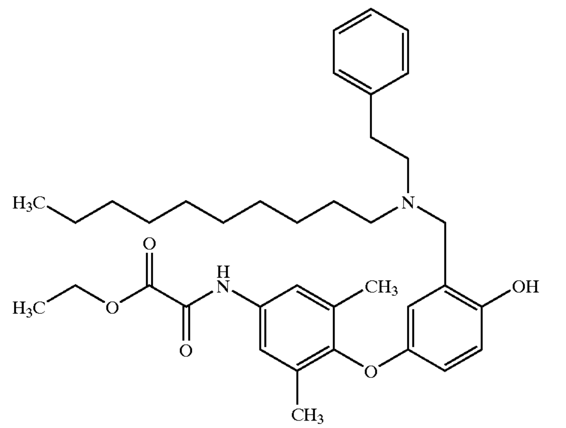 | 602.8 | 3.98 | 602.4 |
| 99 | 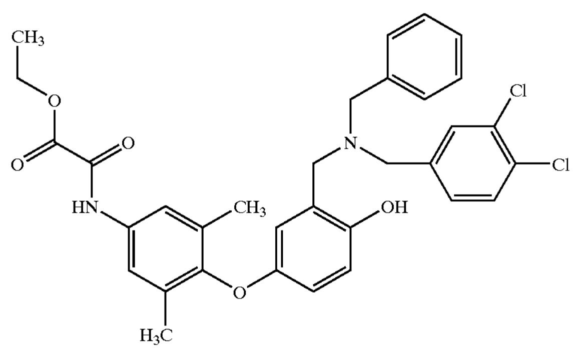 | 607.5 | 5.05 | 606.2 |
| 100 | 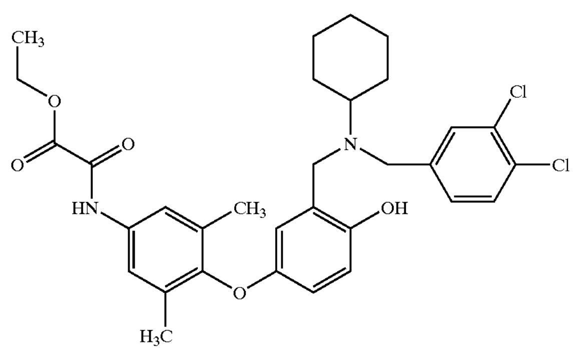 | 613.6 | | 612.2 |
| 101 | 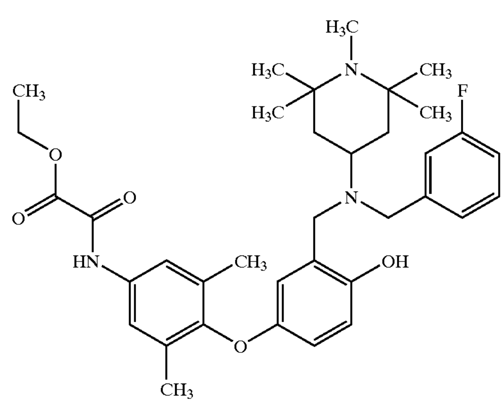 | 619.8 | 5.42 | 619.3 |

-continued

| Ex. No. | Structure | MW [g/mol] calculated | Retention time [min] | MW [g/mol] found |
|---------|-----------|----------------------|----------------------|------------------|
| 102 | 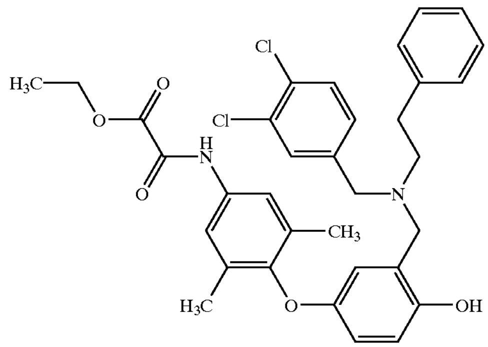 | 621.6 | 4.30 | 620.2 |
| 103 | 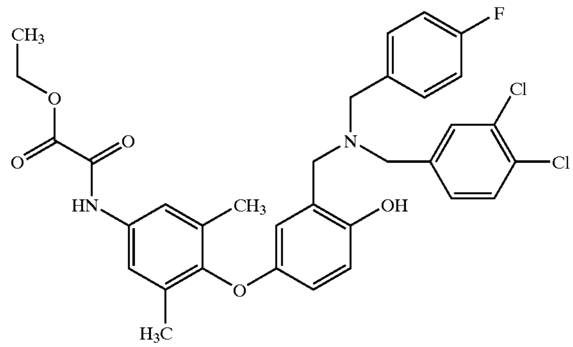 | 625.5 | 5.14 | 624.2 |
| 104 | 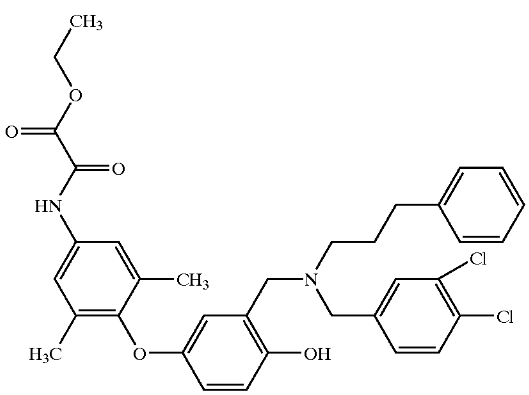 | 635.6 | 4.11 | 634.2 |
| 105 | 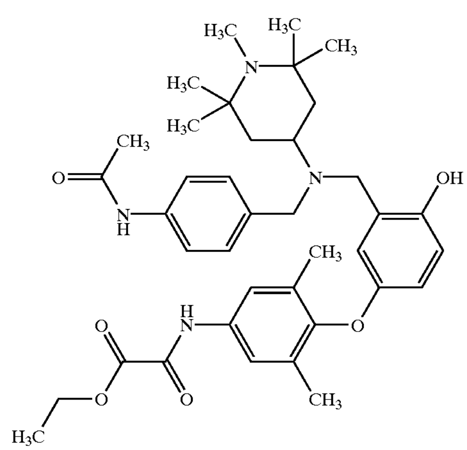 | 658.8 | 5.01 | 658.4 |

-continued

| Ex. No. | Structure | MW [g/mol] calculated | Retention time [min] | MW [g/mol] found |
|---|---|---|---|---|
| 106 | 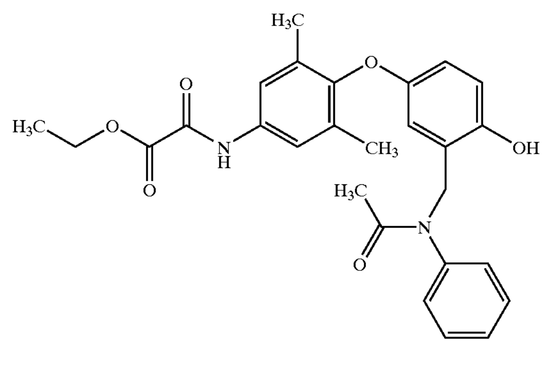 | 476.5 | 4.30 | 476.2 |
| 107 | 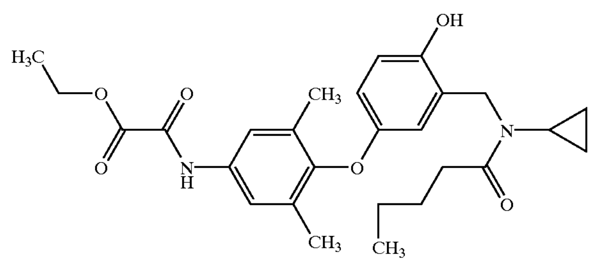 | 482.6 | 4.53 | 482.2 |
| 108 | 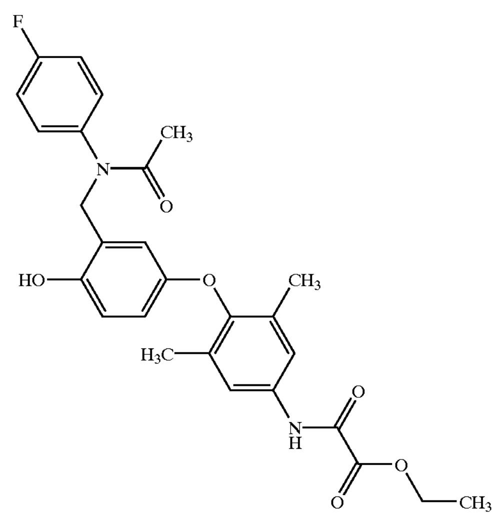 | 494.5 | 4.26 | 494.2 |

| Ex. No. | Structure | MW [g/mol] calculated | Retention time [min] | MW [g/mol] found |
|---|---|---|---|---|
| 109 | 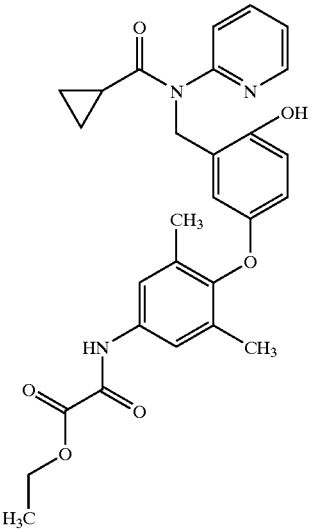 | 503.6 | 4.24 | 530.2 |
| 110 | 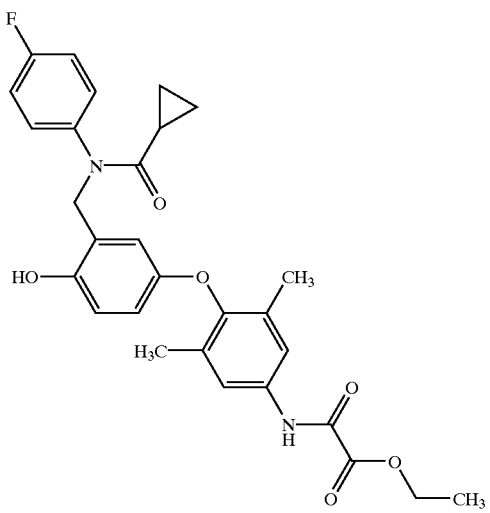 | 520.6 | 4.59 | 520.2 |
| 111 | 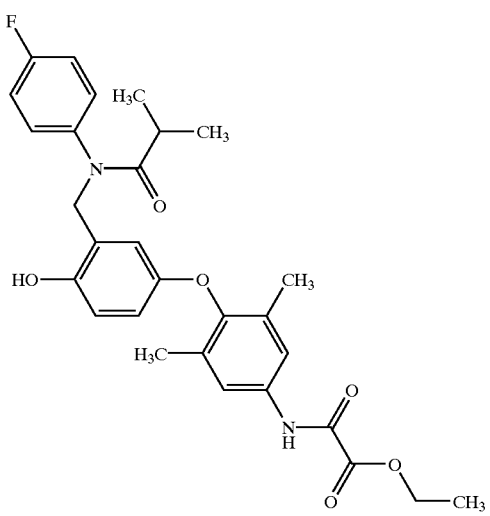 | 522.6 | 4.63 | 522.2 |

-continued

| Ex. No. | Structure | MW [g/mol] calculated | Retention time [min] | MW [g/mol] found |
|---|---|---|---|---|
| 112 | 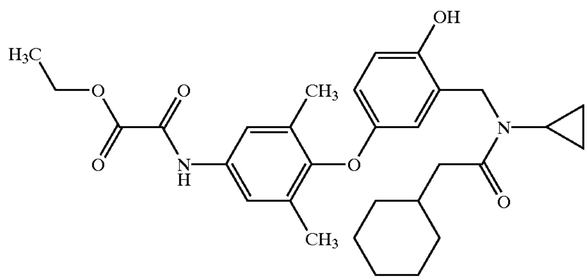 | 522.6 | 4.96 | 522.3 |
| 113 | 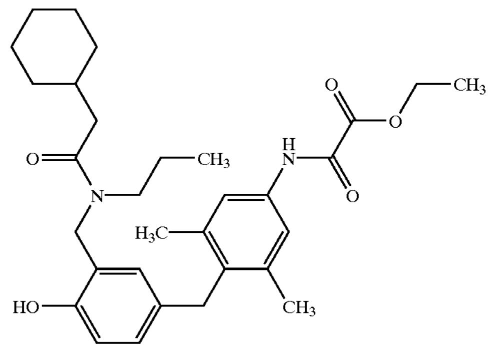 | 524.7 | 5.08 | 524.3 |
| 114 | 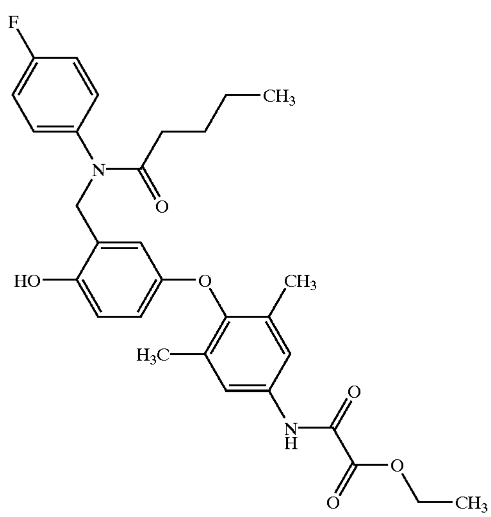 | 536.6 | 4.83 | 536.2 |
| 115 | 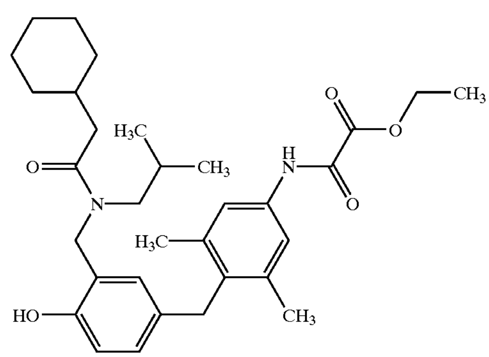 | 538.7 | 5.16 | 538.3 |

-continued

| Ex. No. | Structure | MW [g/mol] calculated | Retention time [min] | MW [g/mol] found |
|---------|-----------|----------------------|---------------------|------------------|
| 116 | 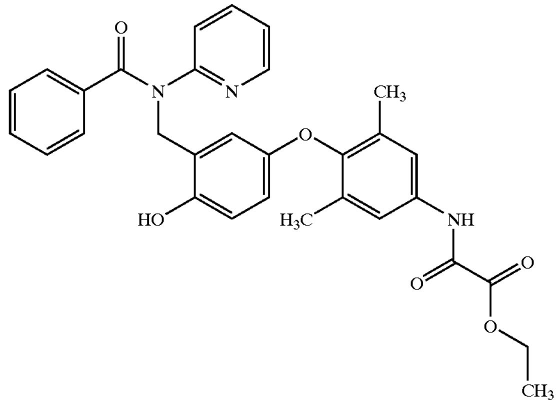 | 539.6 | 4.38 | 539.2 |
| 117 | 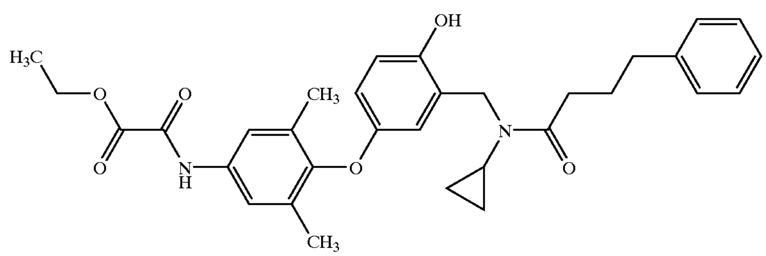 | 544.7 | 4.78 | 544.3 |
| 118 | 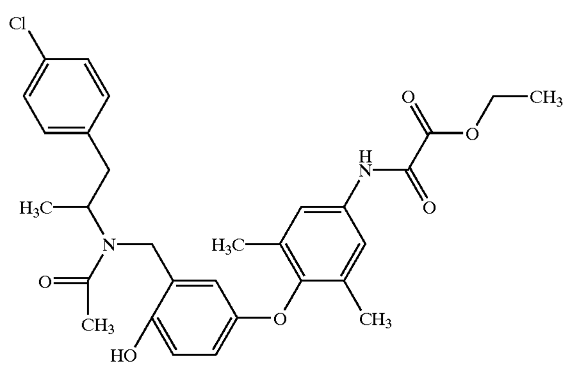 | 553.1 | 4.52 | 552.2 |
| 119 | 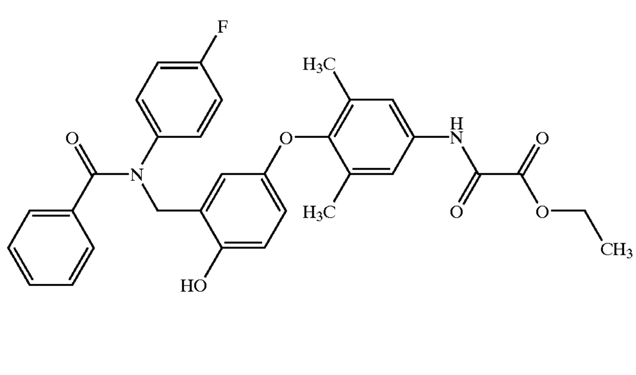 | 556.6 | 4.55 | 556.2 |

| Ex. No. | Structure | MW [g/mol] calculated | Retention time [min] | MW [g/mol] found |
|---|---|---|---|---|
| 120 | 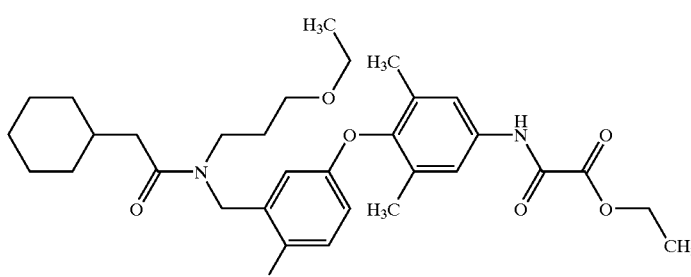 | 568.7 | 5.07 | 568.3 |
| 121 | 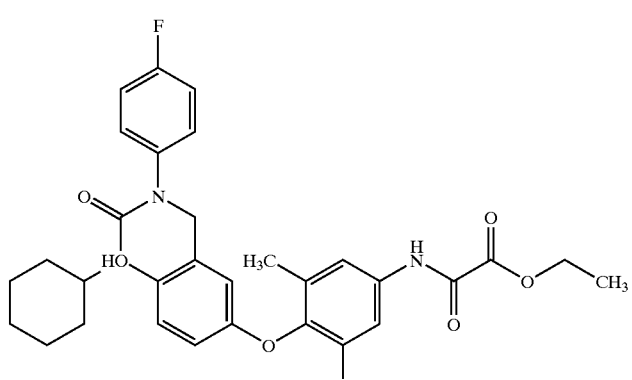 | 576.7 | 5.22 | 576.3 |
| 122 | 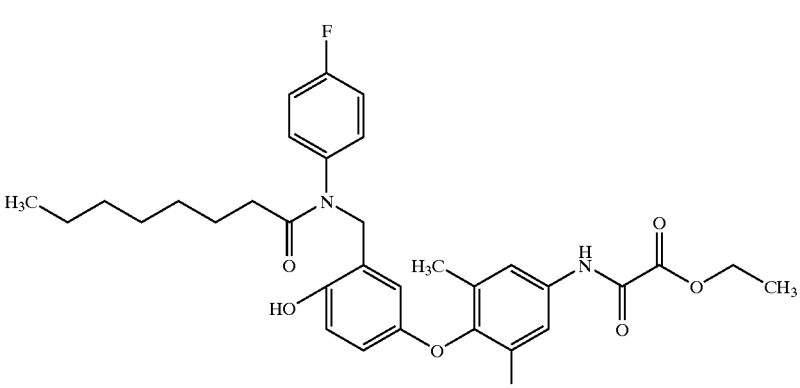 | 578.7 | 5.40 | 578.3 |
| 123 | 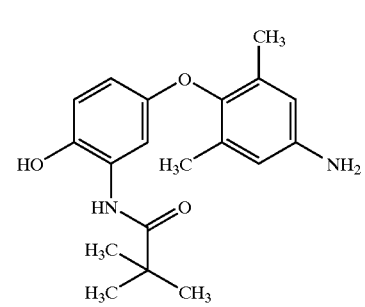 | 328.4 | 2.83 | 328.2 |

-continued

| Ex. No. | Structure | MW [g/mol] calculated | Retention time [min] | MW [g/mol] found |
|---|---|---|---|---|
| 124 | 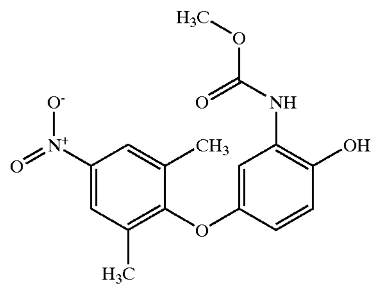 | 332.3 | 4.19 | 332.1 |
| 125 | 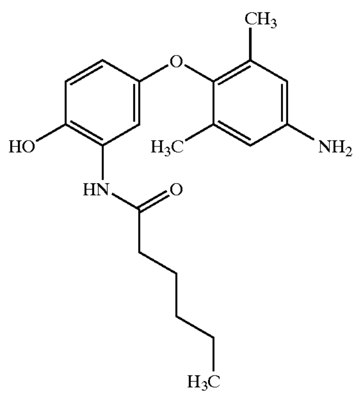 | 342.4 | 3.18 | 342.2 |
| 126 | 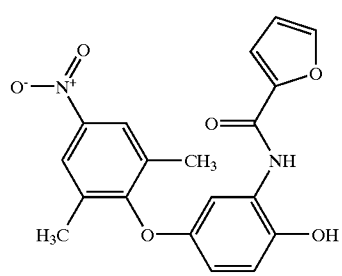 | 368.3 | 4.40 | 368.1 |
| 127 | 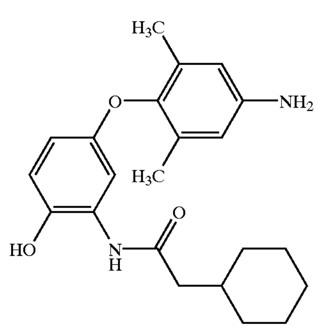 | 368.5 | 3.42 | 368.2 |

| Ex. No. | Structure | MW [g/mol] calculated | Retention time [min] | MW [g/mol] found |
|---|---|---|---|---|
| 128 | 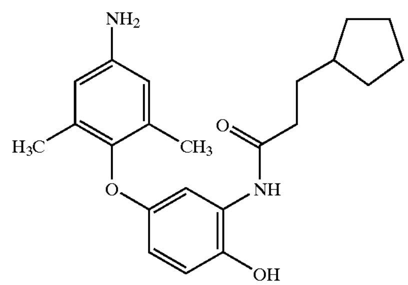 | 368.5 | 3.47 | 368.2 |
| 129 | 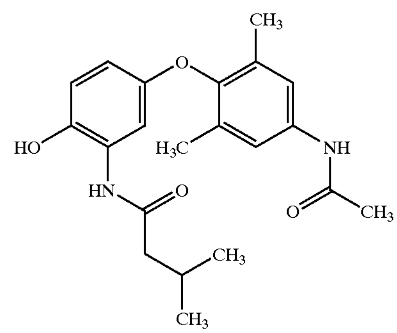 | 370.4 | 3.81 | 370.2 |
| 130 | 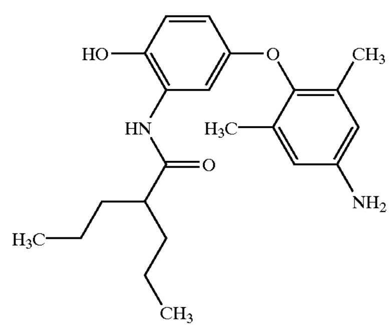 | 370.5 | 3.62 | 370.2 |
| 131 | 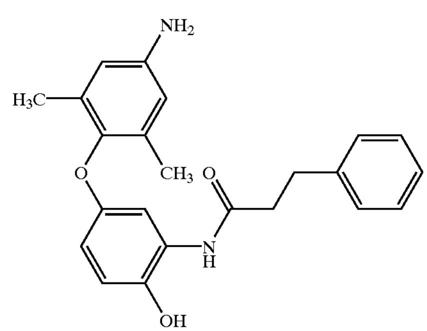 | 376.5 | 3.13 | 376.2 |
| 132 | 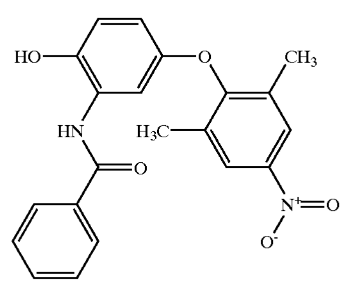 | 378.4 | 4.58 | 378.1 |

| Ex. No. | Structure | MW [g/mol] calculated | Retention time [min] | MW [g/mol] found |
|---|---|---|---|---|
| 133 | 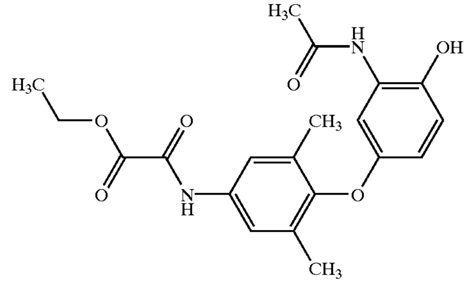 | 386.4 | 3.56 | 386.1 |
| 134 | 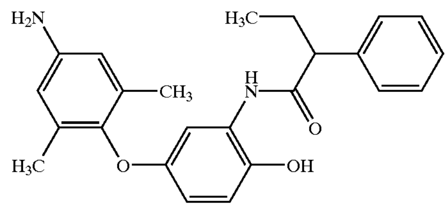 | 390.5 | 3.42 | 390.2 |
| 135 | 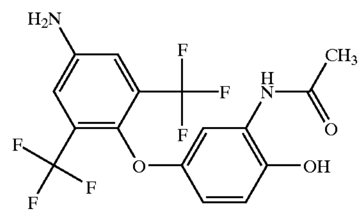 | 394.3 | 3.71 | 394.1 |
| 136 | 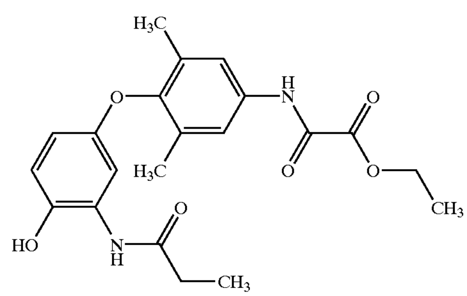 | 400.4 | 3.85 | 400.2 |
| 137 | 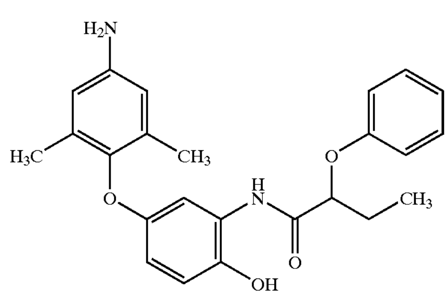 | 406.5 | 3.41 | 406.2 |

-continued

| Ex. No. | Structure | MW [g/mol] calculated | Retention time [min] | MW [g/mol] found |
|---|---|---|---|---|
| 138 | 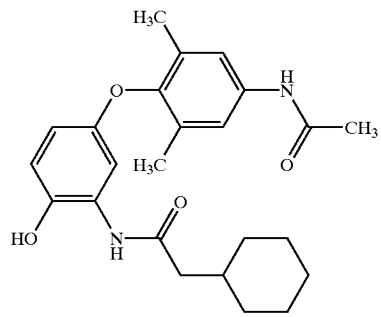 | 410.5 | 4.26 | 410.2 |
| 139 | 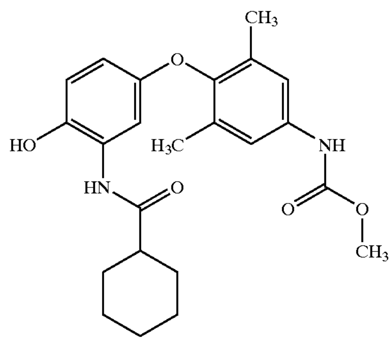 | 412.5 | 4.41 | 412.2 |
| 140 | 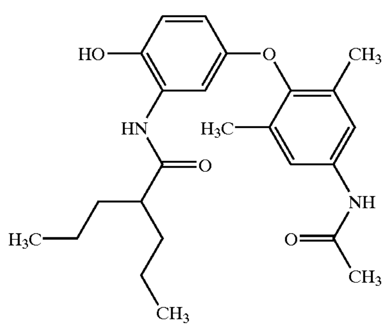 | 412.5 | 4.42 | 412.2 |
| 141 | 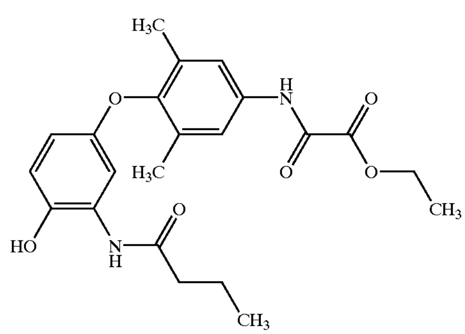 | 414.5 | 4.05 | 414.2 |

-continued

| Ex. No. | Structure | MW [g/mol] calculated | Retention time [min] | MW [g/mol] found |
|---|---|---|---|---|
| 142 | 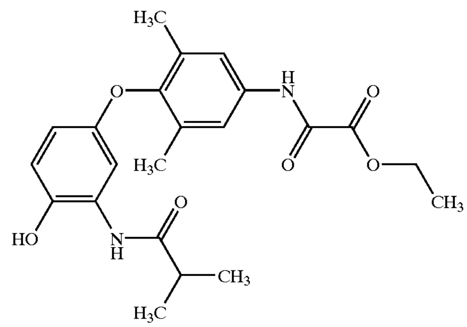 | 414.5 | 4.05 | 414.2 |
| 143 | 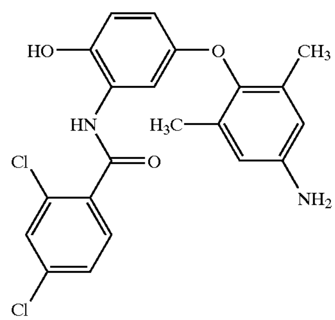 | 417.3 | 3.29 | 416.1 |
| 144 | 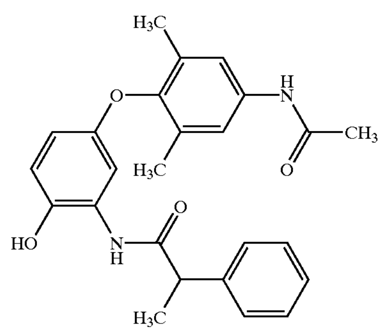 | 418.5 | 4.02 | 418.3 |
| 145 | 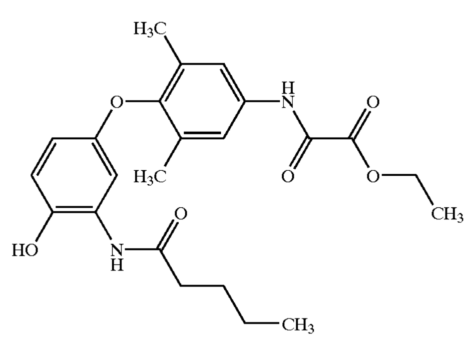 | 428.5 | 4.27 | 428.2 |

-continued
| Ex. No. | Structure | MW [g/mol] calculated | Retention time [min] | MW [g/mol] found |
|---|---|---|---|---|
| 146 | 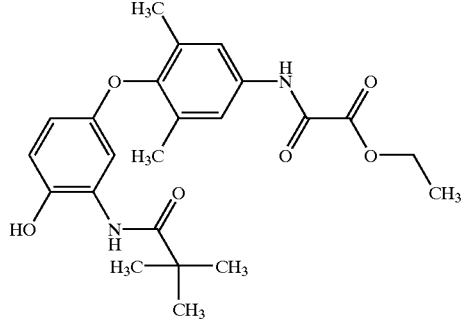 | 428.5 | 4.23 | 428.2 |
| 147 | 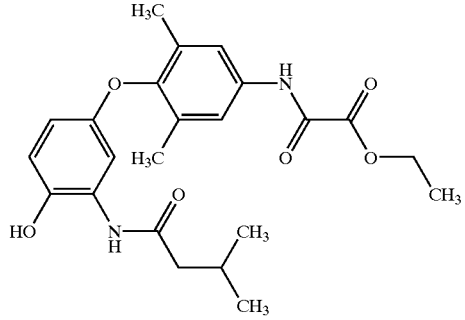 | 428.5 | 4.24 | 428.2 |
| 148 | 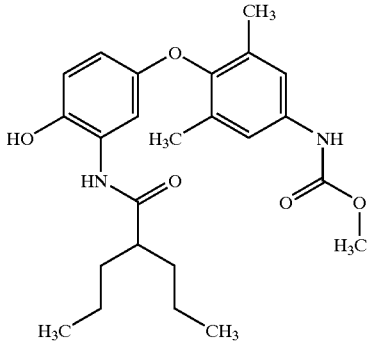 | 428.5 | 4.75 | 428.2 |
| 149 | 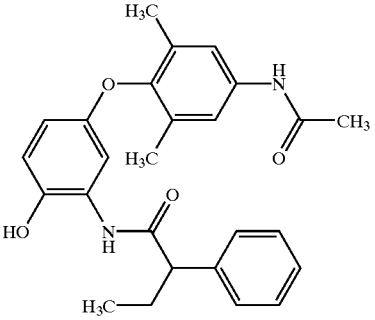 | 432.5 | 4.22 | 432.2 |

| Ex. No. | Structure | MW [g/mol] calculated | Retention time [min] | MW [g/mol] found |
|---|---|---|---|---|
| 150 | 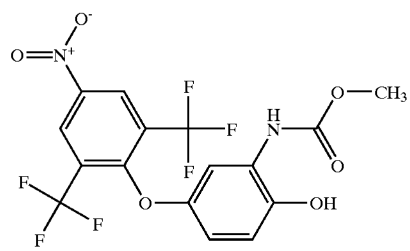 | 440.3 | 4.30 | 440.0 |
| 151 | 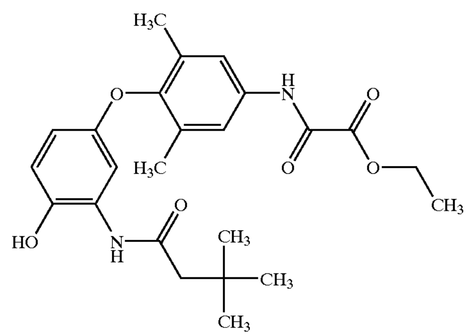 | 442.5 | 4.44 | 442.2 |
| 152 | 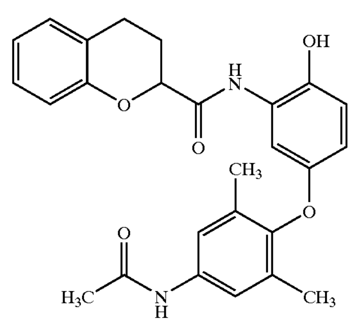 | 446.5 | 4.09 | 446.2 |
| 153 | 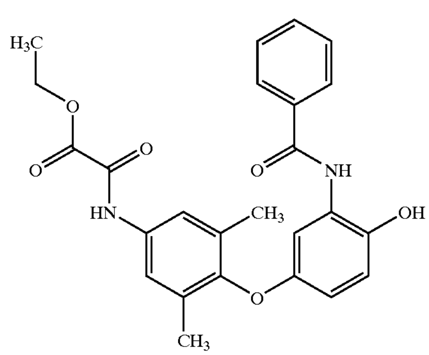 | 448.5 | 4.19 | 448.2 |

| Ex. No. | Structure | MW [g/mol] calculated | Retention time [min] | MW [g/mol] found |
|---|---|---|---|---|
| 154 | 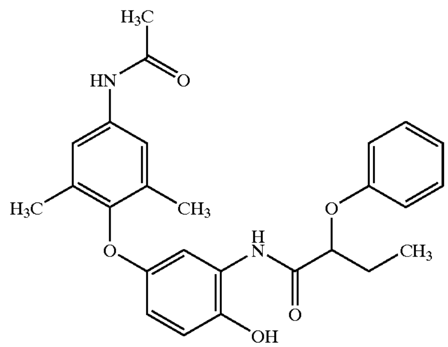 | 448.5 | 4.19 | 448.2 |
| 155 | 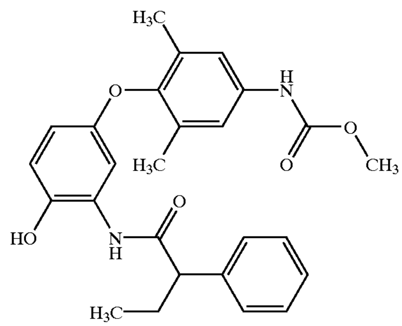 | 448.5 | 4.53 | 448.2 |
| 156 | 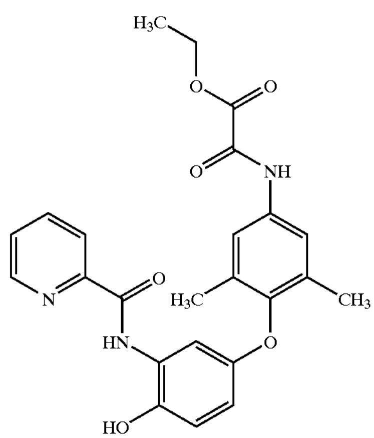 | 449.5 | 4.14 | 449.2 |
| 157 | 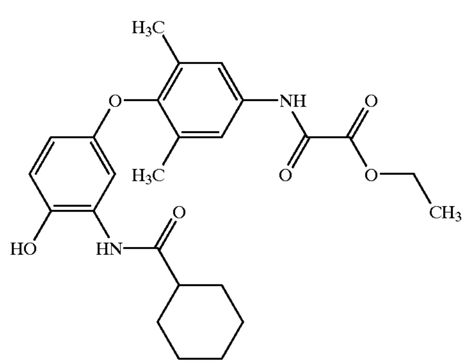 | 454.5 | 4.47 | 454.2 |

| Ex. No. | Structure | MW [g/mol] calculated | Retention time [min] | MW [g/mol] found |
|---|---|---|---|---|
| 158 | 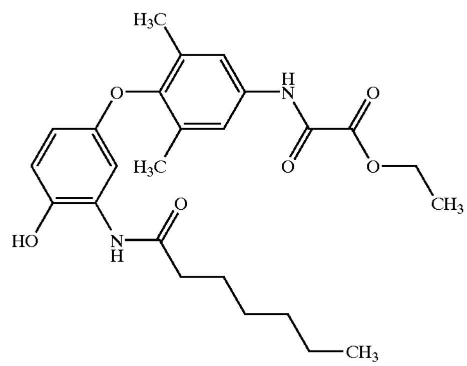 | 456.5 | 4.68 | 456.2 |
| 159 | 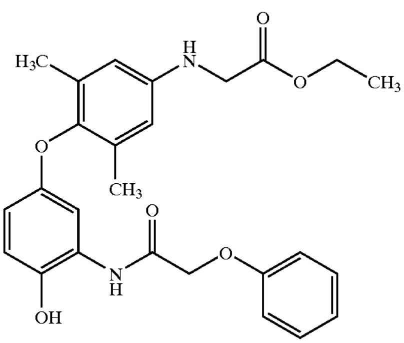 | 464.5 | 4.45 | 464.2 |
| 160 | 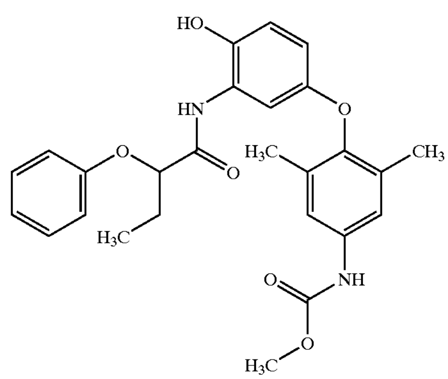 | 464.5 | 4.50 | 464.2 |
| 161 | 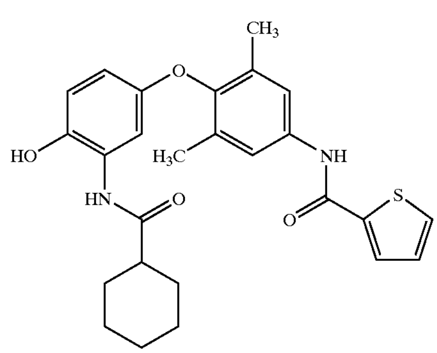 | 464.4 | 4.64 | 464.2 |

-continued

| Ex. No. | Structure | MW [g/mol] calculated | Retention time [min] | MW [g/mol] found |
|---|---|---|---|---|
| 162 | 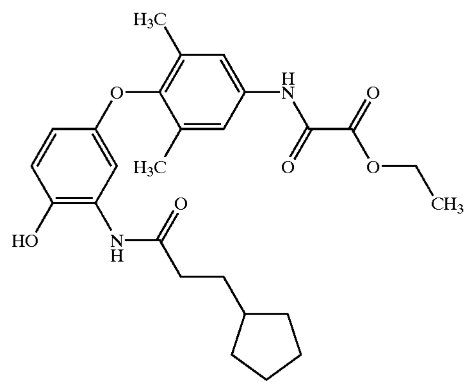 | 468.5 | 4.68 | 468.2 |
| 163 | 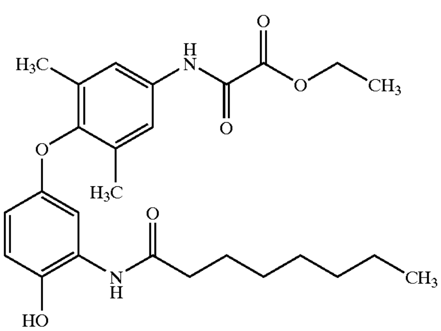 | 470.6 | 4.89 | 470.2 |
| 164 | 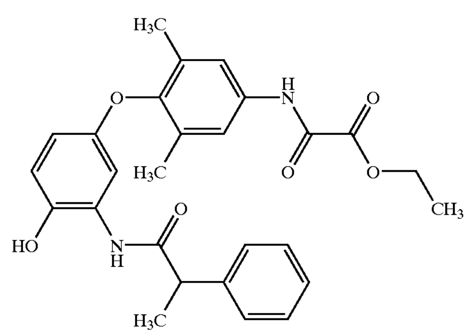 | 476.5 | 4.41 | 476.2 |
| 165 | 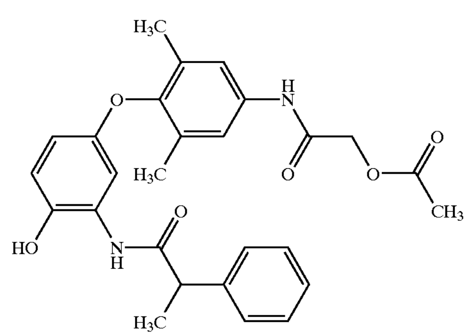 | 476.5 | 4.17 | 476.3 |

-continued

| Ex. No. | Structure | MW [g/mol] calculated | Retention time [min] | MW [g/mol] found |
|---|---|---|---|---|
| 166 | 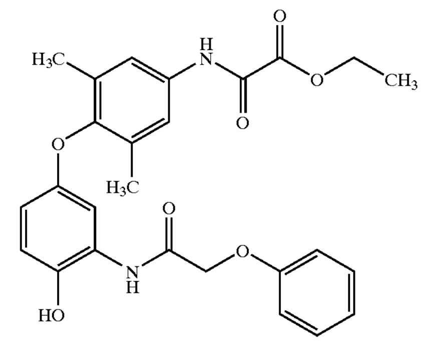 | 478.5 | 4.29 | 478.2 |
| 167 | 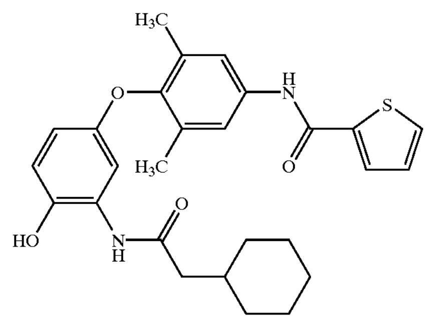 | 478.6 | 4.81 | 478.2 |
| 168 | 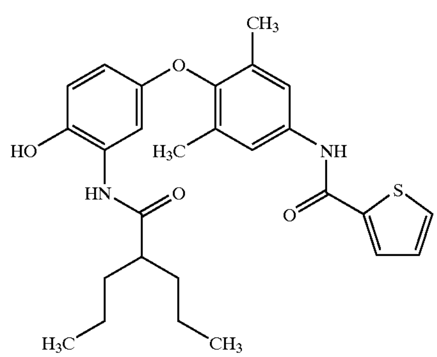 | 480.6 | 4.97 | 480.2 |
| 169 | 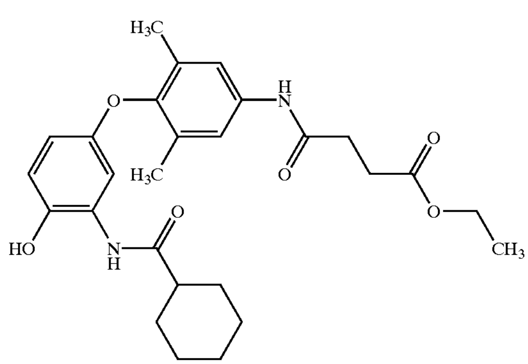 | 482.6 | 4.43 | 482.2 |

-continued

| Ex. No. | Structure | MW [g/mol] calculated | Retention time [min] | MW [g/mol] found |
|---|---|---|---|---|
| 170 | 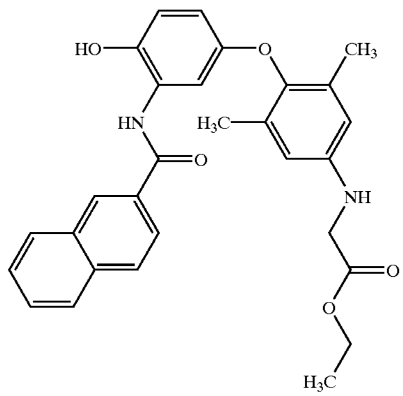 | 484.5 | 4.77 | 484.2 |
| 171 | 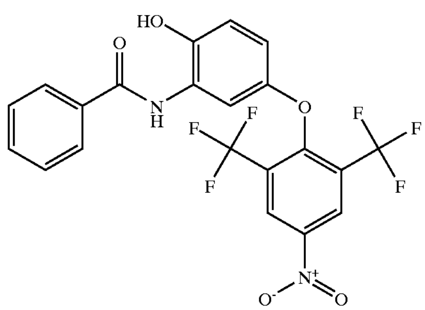 | 486.3 | 4.62 | 486.1 |
| 172 | 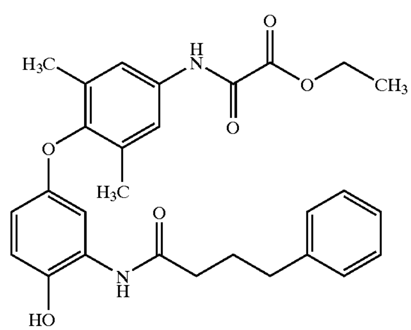 | 490.6 | 4.55 | 490.2 |
| 173 | 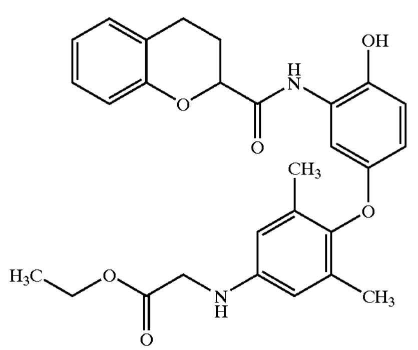 | 490.6 | 4.65 | 490.2 |

-continued

| Ex. No. | Structure | MW [g/mol] calculated | Retention time [min] | MW [g/mol] found |
|---|---|---|---|---|
| 174 | 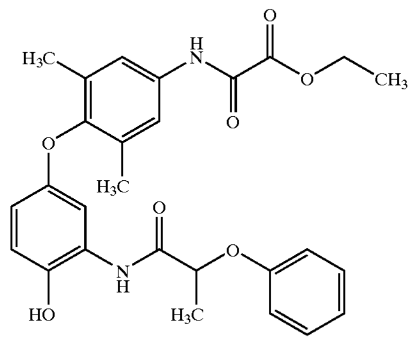 | 492.5 | 4.41 | 492.2 |
| 175 | 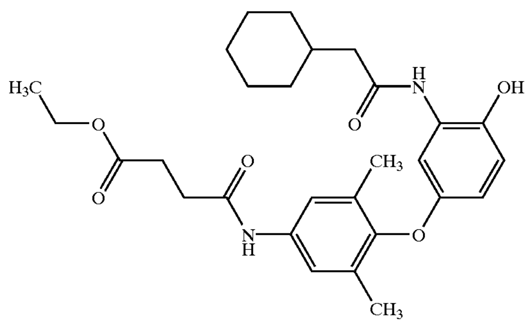 | 496.6 | 4.61 | 496.3 |
| 176 | 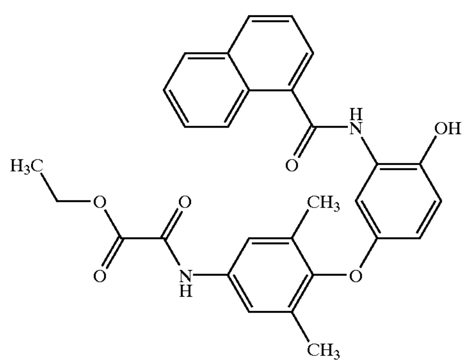 | 498.5 | 4.48 | 498.2 |
| 177 | 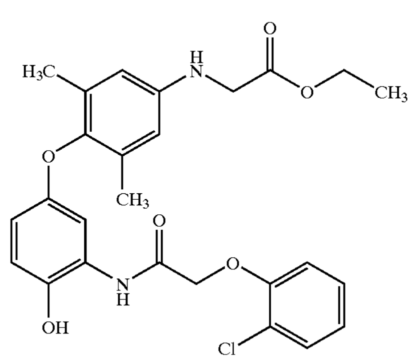 | 499.0 | 4.56 | 498.2 |

-continued

| Ex. No. | Structure | MW [g/mol] calculated | Retention time [min] | MW [g/mol] found |
|---------|-----------|----------------------|---------------------|------------------|
| 178 | 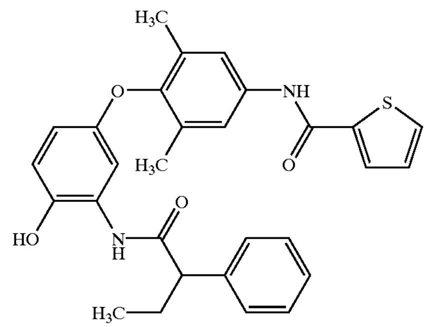 | 500.6 | 4.74 | 500.2 |
| 179 | 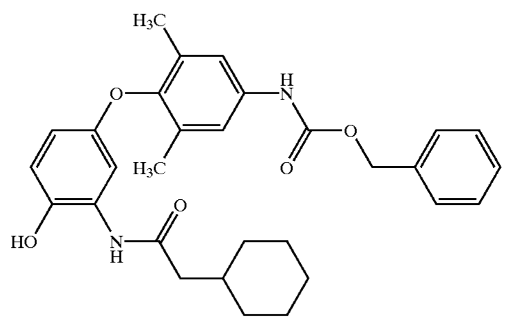 | 502.6 | 5.12 | 502.2 |
| 180 | 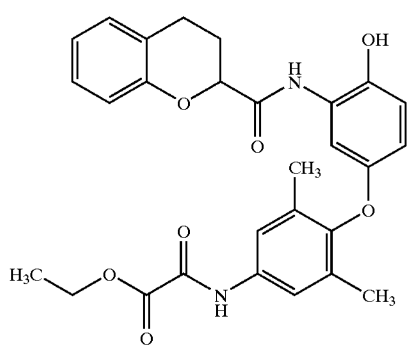 | 504.5 | 4.49 | 504.2 |
| 181 | 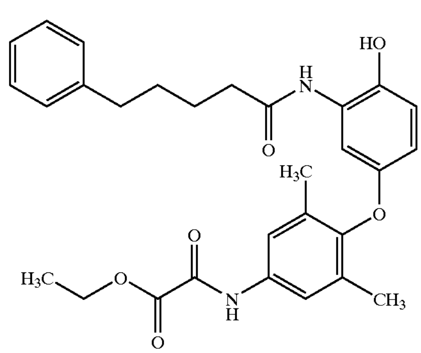 | 504.6 | 4.68 | 504.2 |

| Ex. No. | Structure | MW [g/mol] calculated | Retention time [min] | MW [g/mol] found |
|---|---|---|---|---|
| 182 | 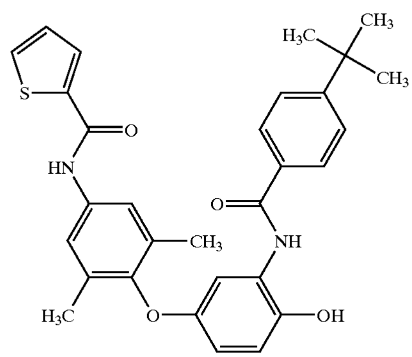 | 514.6 | 4.99 | 514.2 |
| 183 | 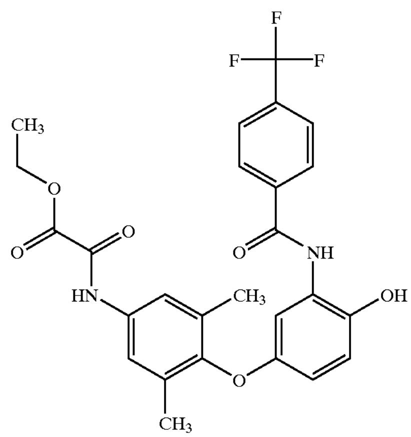 | 516.5 | 4.58 | 516.2 |
| 184 | 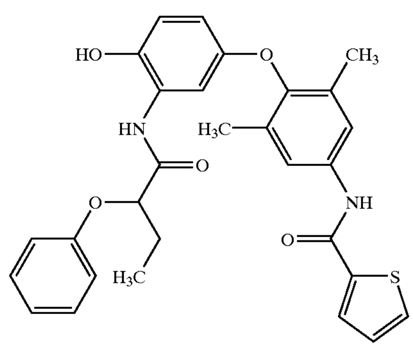 | 516.6 | 4.70 | 516.2 |
| 185 | 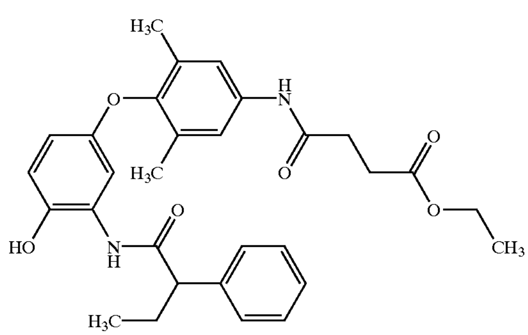 | 518.6 | 4.54 | 518.2 |

| Ex. No. | Structure | MW [g/mol] calculated | Retention time [min] | MW [g/mol] found |
|---|---|---|---|---|
| 186 | 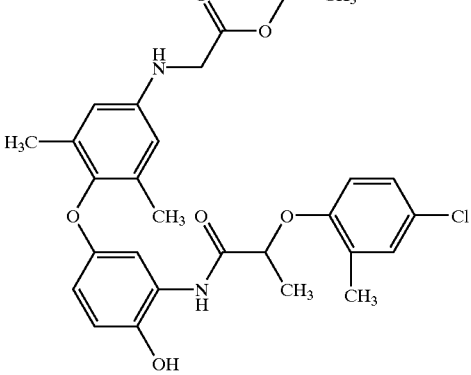 | 527.0 | 4.96 | 526.2 |
| 187 | 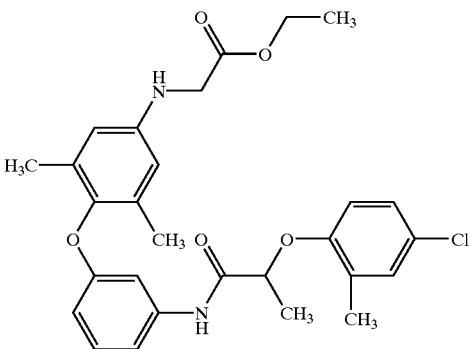 | 527.0 | 4.96 | 526.2 |
| 188 | 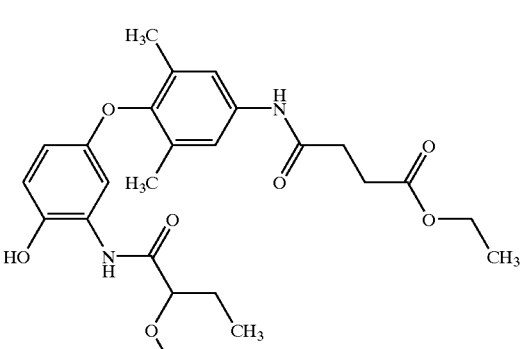 | 534.6 | 4.51 | 534.2 |

-continued

| Ex. No. | Structure | MW [g/mol] calculated | Retention time [min] | MW [g/mol] found |
|---|---|---|---|---|
| 189 | 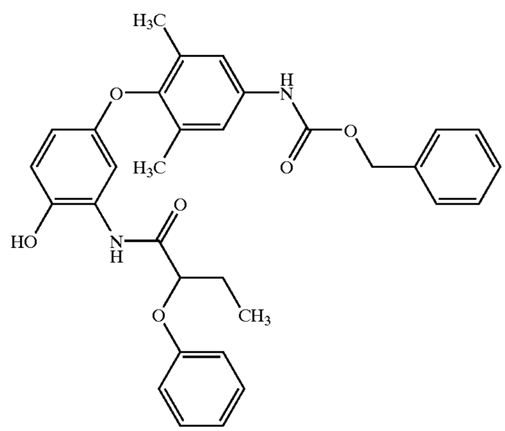 | 540.6 | 5.00 | 540.2 |
| 190 | 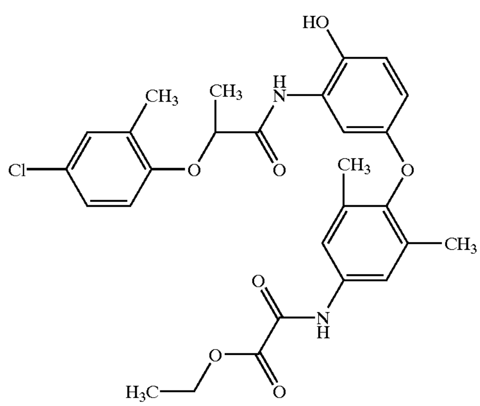 | 541.0 | 4.80 | 540.2 |
| 191 | 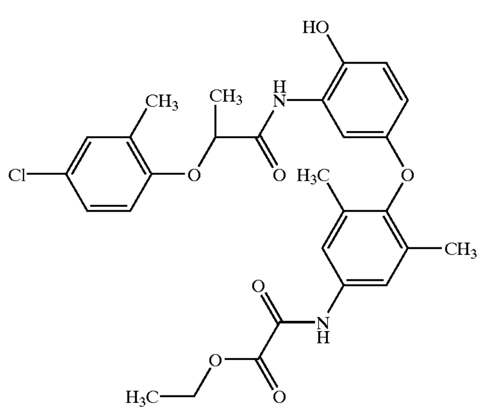 | 541.0 | 4.80 | 540.2 |

-continued

| Ex. No. | Structure | MW [g/mol] calculated | Retention time [min] | MW [g/mol] found |
|---|---|---|---|---|
| 192 | 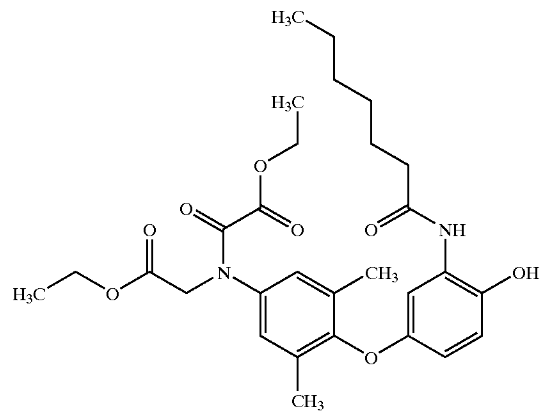 | 542.6 | 4.94 | 542.3 |
| 193 | 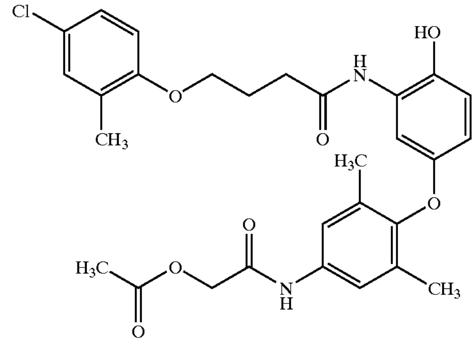 | 555.0 | 4.65 | 554.2 |
| 194 | 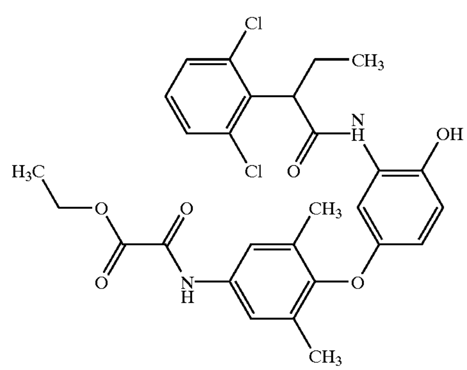 | 559.4 | 4.85 | 558.1 |
| 195 | 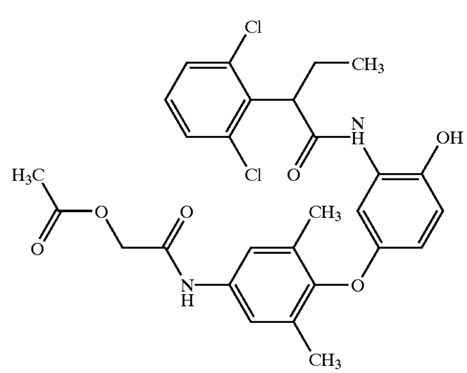 | 559.4 | 4.61 | 558.1 |

-continued

| Ex. No. | Structure | MW [g/mol] calculated | Retention time [min] | MW [g/mol] found |
|---|---|---|---|---|
| 196 | 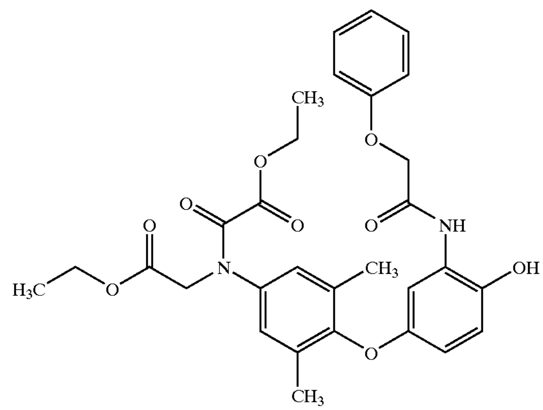 | 564.6 | 4.57 | 564.2 |
| 197 | 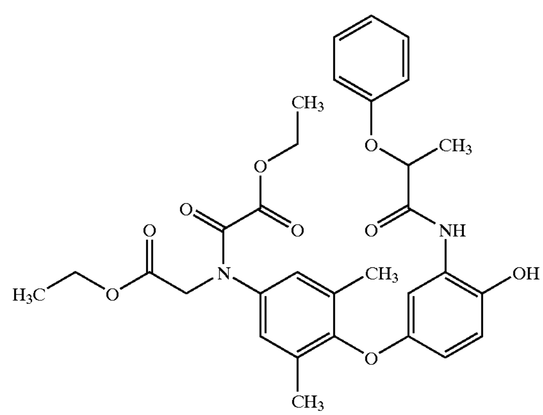 | 578.6 | 4.69 | 576.2 |
| 198 | 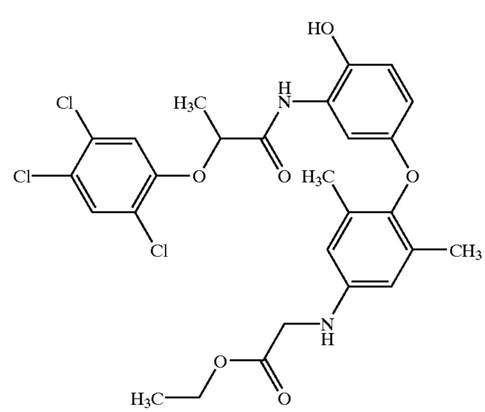 | 581.9 | 5.11 | 580.1 |

| Ex. No. | Structure | MW [g/mol] calculated | Retention time [min] | MW [g/mol] found |
|---|---|---|---|---|
| 199 | 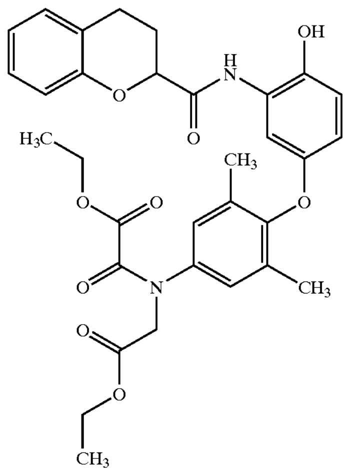 | 590.6 | 4.76 | 590.2 |
| 200 | 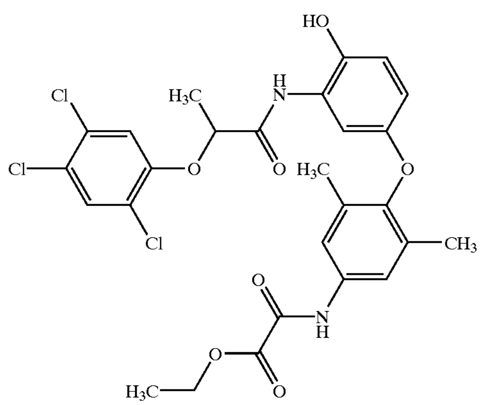 | 595.9 | 4.96 | 594.1 |
| 201 | 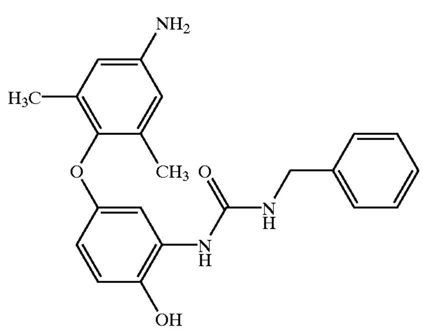 | 377.4 | 2.84 | 377.2 |
| 202 | 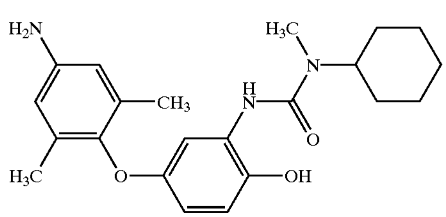 | 383.5 | 3.21 | 383.2 |

-continued

| Ex. No. | Structure | MW [g/mol] calculated | Retention time [min] | MW [g/mol] found |
|---|---|---|---|---|
| 203 | 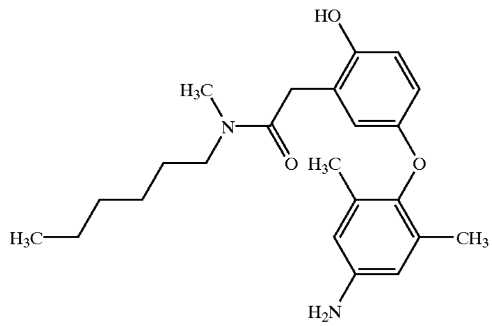 | 385.5 | 3.51 | 385.2 |
| 204 | 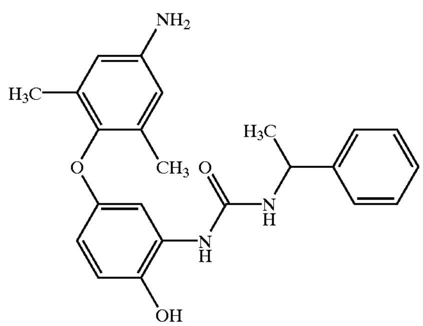 | 391.5 | 2.97 | 391.2 |
| 205 | 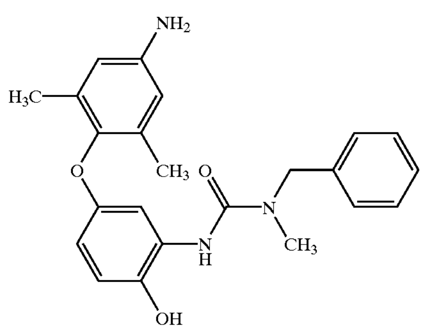 | 391.5 | 3.05 | 391.2 |
| 206 | 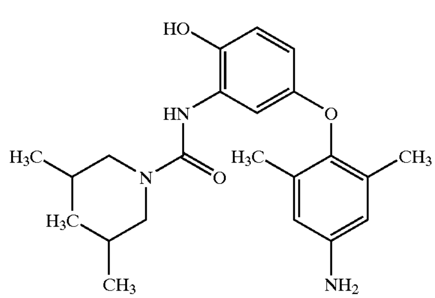 | 399.5 | 3.68 | 399.3 |

-continued

| Ex. No. | Structure | MW [g/mol] calculated | Retention time [min] | MW [g/mol] found |
|---|---|---|---|---|
| 207 | 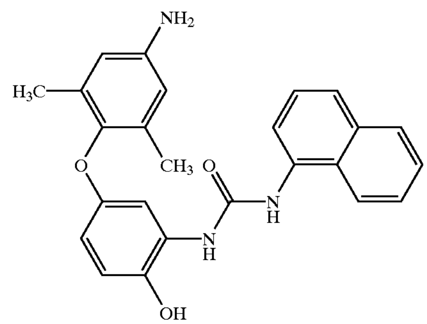 | 413.5 | 3.20 | 413.2 |
| 208 | 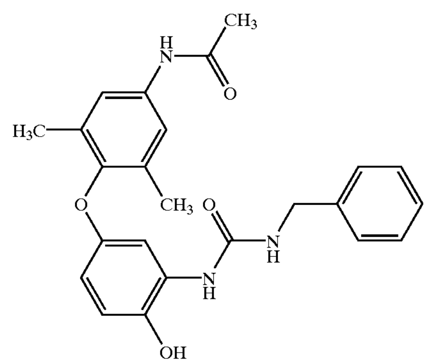 | 419.5 | 3.74 | 419.2 |
| 209 | 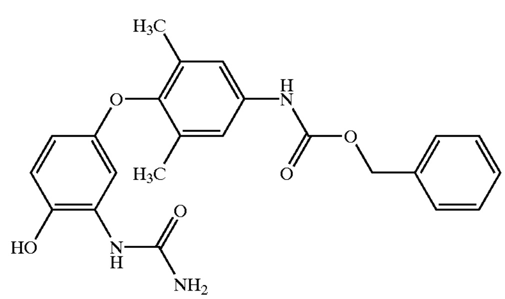 | 421.5 | 3.97 | 421.0 |
| 210 | 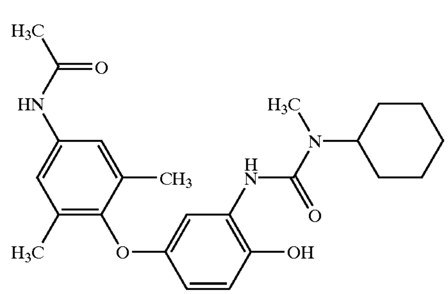 | 425.5 | 4.13 | 425.2 |

-continued

| Ex. No. | Structure | MW [g/mol] calculated | Retention time [min] | MW [g/mol] found |
|---|---|---|---|---|
| 211 | 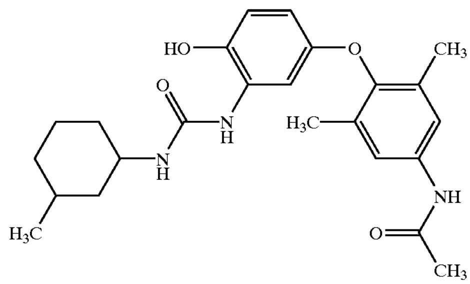 | 425.5 | 4.13 | 425.2 |
| 212 | 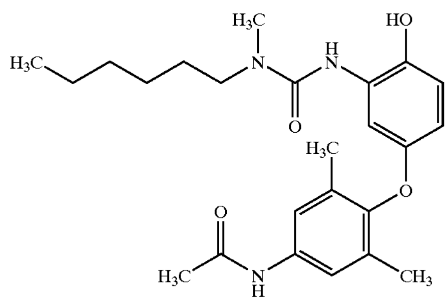 | 427.5 | 4.37 | 427.2 |
| 213 | 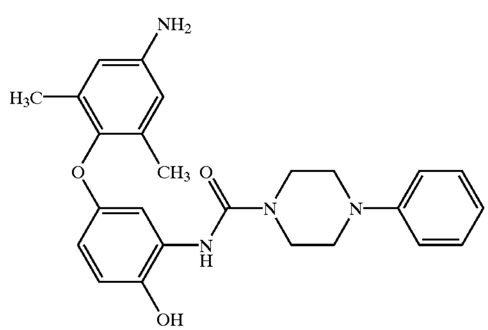 | 432.5 | 3.04 | 432.2 |
| 214 | 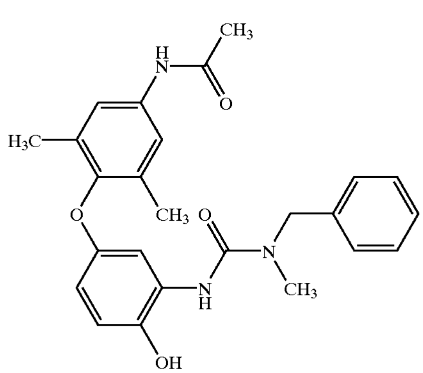 | 433.5 | 3.94 | 433.2 |

| Ex. No. | Structure | MW [g/mol] calculated | Retention time [min] | MW [g/mol] found |
|---|---|---|---|---|
| 215 | 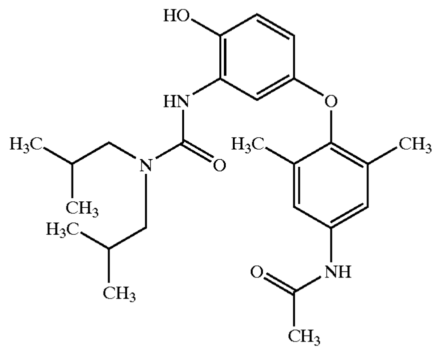 | 441.6 | 4.52 | 441.3 |
| 216 | 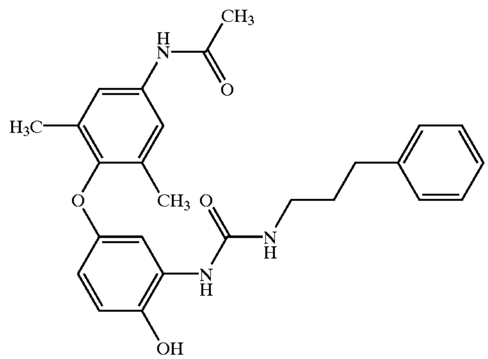 | 447.5 | 4.03 | 447.2 |
| 217 | 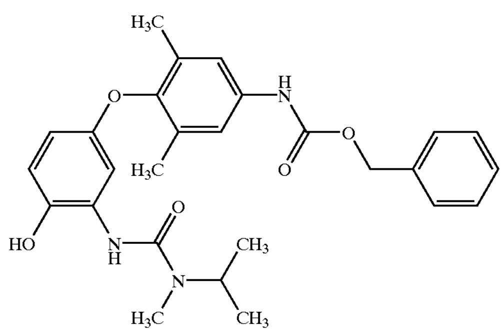 | 477.6 | 4.66 | 477.2 |
| 218 | 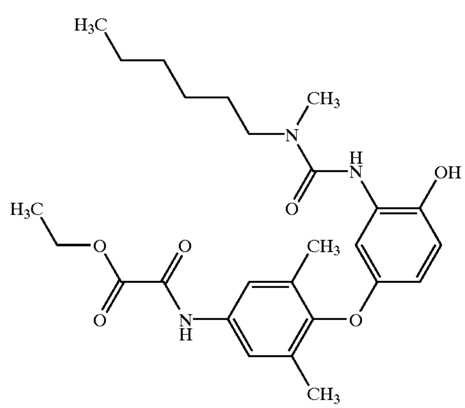 | 485.6 | 4.75 | 485.3 |

| Ex. No. | Structure | MW [g/mol] calculated | Retention time [min] | MW [g/mol] found |
|---|---|---|---|---|
| 219 | 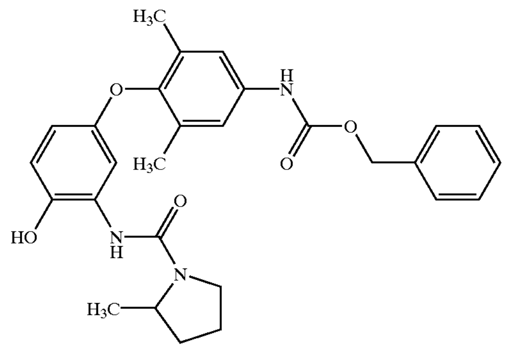 | 489.6 | 4.67 | 489.2 |
| 220 | 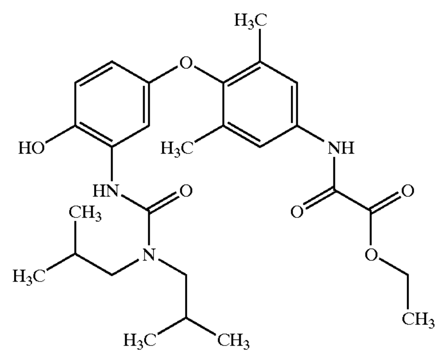 | 499.6 | 4.89 | 499.3 |
| 221 | 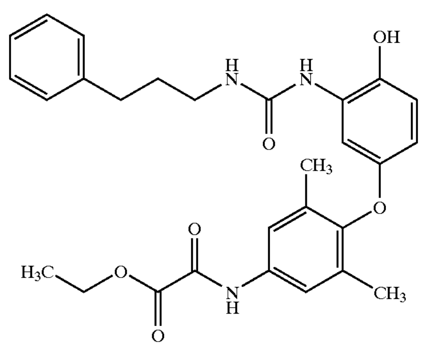 | 505.6 | 4.43 | 505.2 |
| 222 | 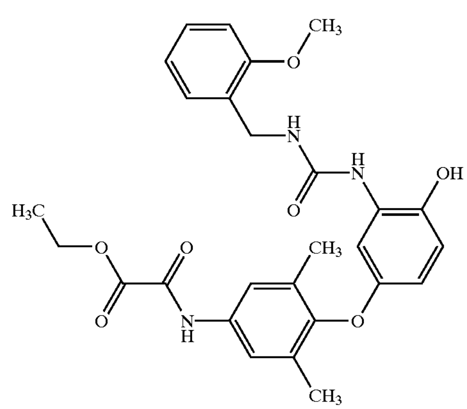 | 507.5 | 4.27 | 507.2 |

-continued

| Ex. No. | Structure | MW [g/mol] calculated | Retention time [min] | MW [g/mol] found |
|---|---|---|---|---|
| 223 | 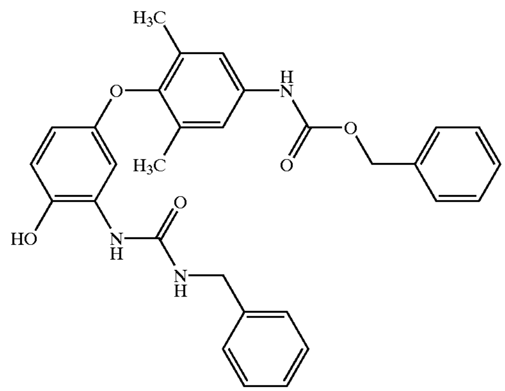 | 511.6 | 4.63 | 511.2 |
| 224 | 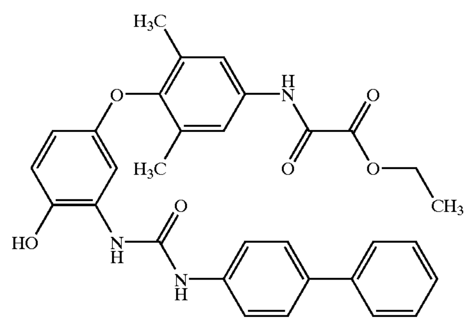 | 539.6 | 4.68 | 539.2 |
| 225 | 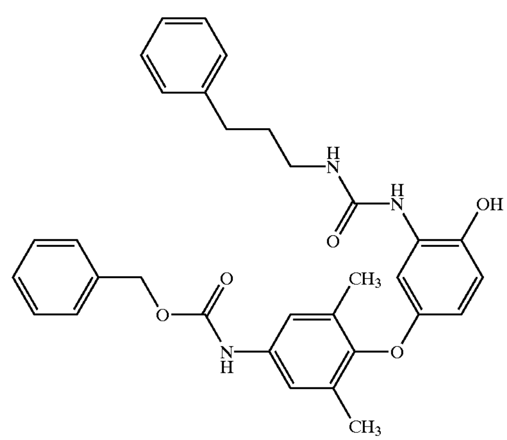 | 539.6 | 4.84 | 539.2 |
| 226 | 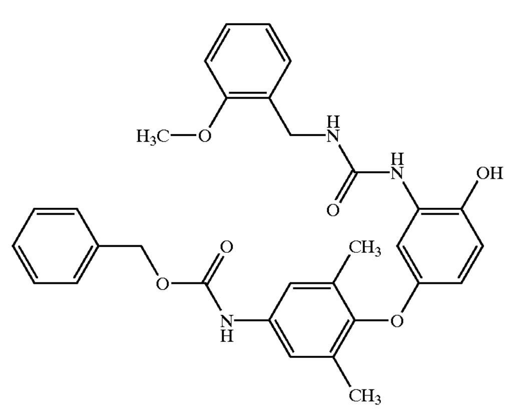 | 541.6 | 4.69 | 541.2 |

-continued

| Ex. No. | Structure | MW [g/mol] calculated | Retention time [min] | MW [g/mol] found |
|---|---|---|---|---|
| 227 | 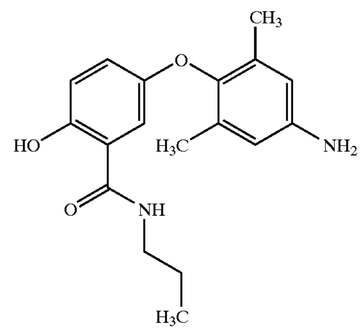 | 314.4 | 3.02 | 314.2 |
| 228 | 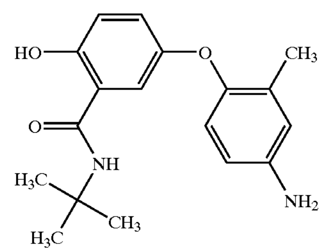 | 328.4 | 3.27 | 328.2 |
| 229 | 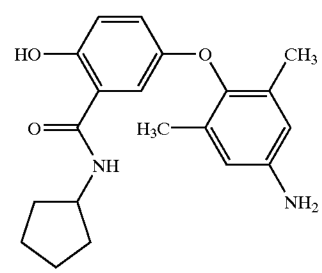 | 340.4 | 3.32 | 340.2 |
| 230 | 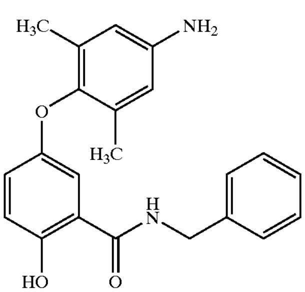 | 362.4 | 3.41 | 362.2 |
| 231 | 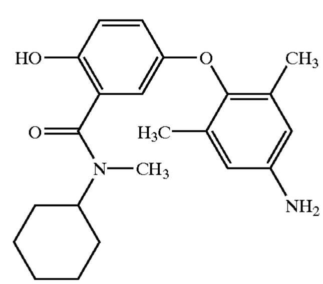 | 368.5 | 3.87 | 368.2 |

-continued

| Ex. No. | Structure | MW [g/mol] calculated | Retention time [min] | MW [g/mol] found |
|---------|-----------|----------------------|----------------------|------------------|
| 232 | 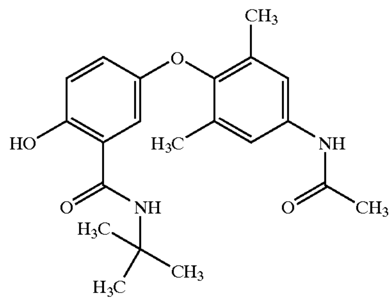 | 370.5 | 4.15 | 370.2 |
| 233 | 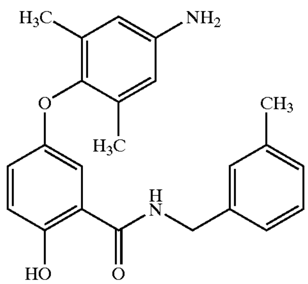 | 376.5 | 3.65 | 376.2 |
| 234 | 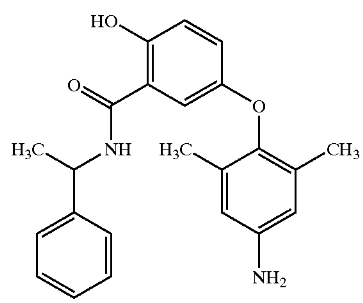 | 376.5 | 3.52 | 376.2 |
| 235 | 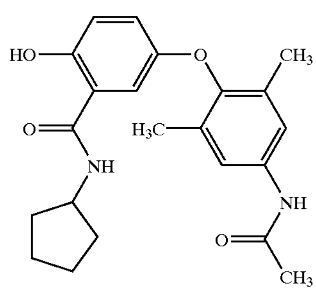 | 382.5 | 4.16 | 382.2 |
| 236 | 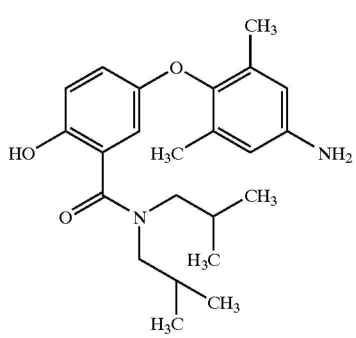 | 384.5 | 3.45 | 384.2 |

-continued
| Ex. No. | Structure | MW [g/mol] calculated | Retention time [min] | MW [g/mol] found |
|---|---|---|---|---|
| 237 | 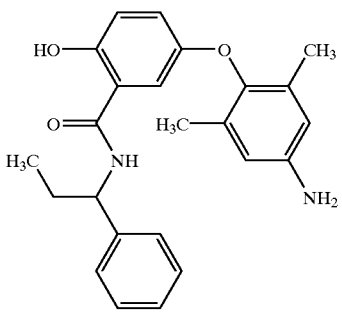 | 390.5 | 3.70 | 390.2 |
| 238 | 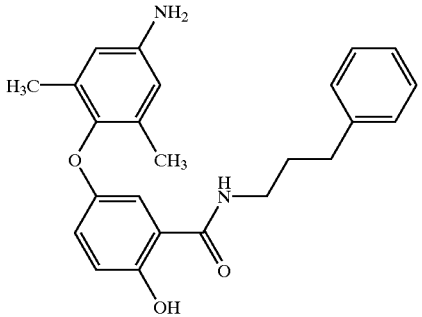 | 390.5 | 3.79 | 390.2 |
| 239 | 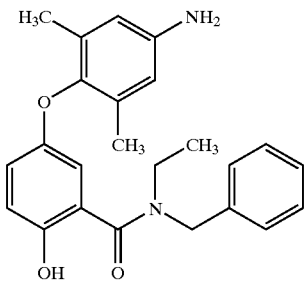 | 390.5 | 3.06 | 390.2 |
| 240 | 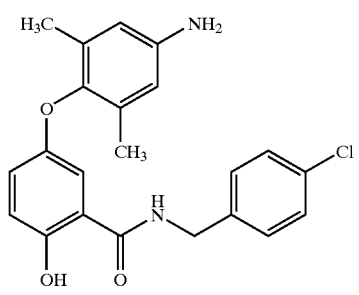 | 396.9 | 3.74 | 396.1 |
| 241 | 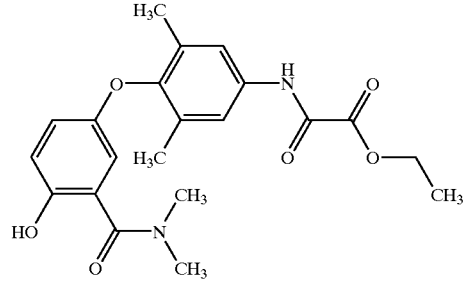 | 400.4 | 3.50 | 400.2 |

-continued

| Ex. No. | Structure | MW [g/mol] calculated | Retention time [min] | MW [g/mol] found |
|---|---|---|---|---|
| 242 | 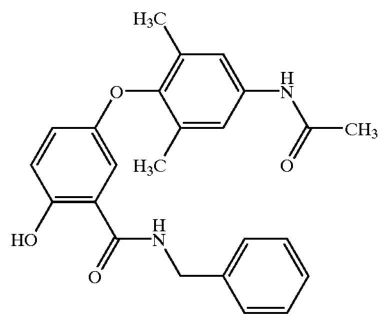 | 404.5 | 4.19 | 404.2 |
| 243 | 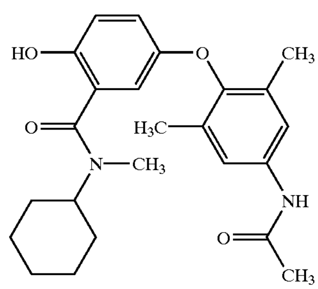 | 410.5 | 4.60 | 410.2 |
| 244 | 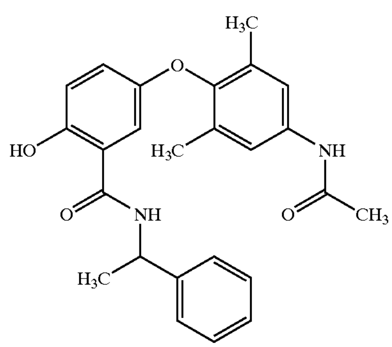 | 418.5 | 4.26 | 418.2 |
| 245 | 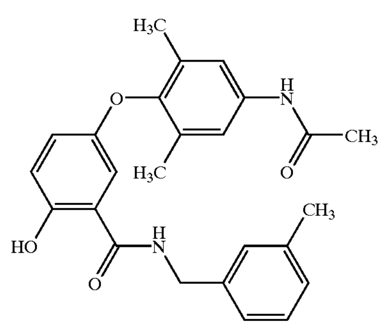 | 418.5 | 4.35 | 418.2 |

-continued

| Ex. No. | Structure | MW [g/mol] calculated | Retention time [min] | MW [g/mol] found |
|---|---|---|---|---|
| 246 | 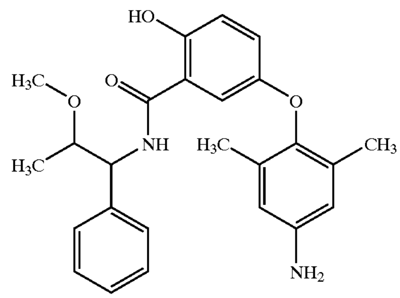 | 420.5 | 3.52 | 420.2 |
| 247 | 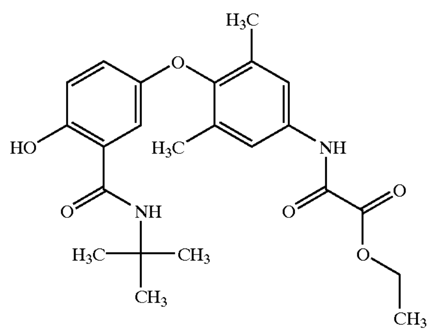 | 428.5 | 4.59 | 428.2 |
| 248 | 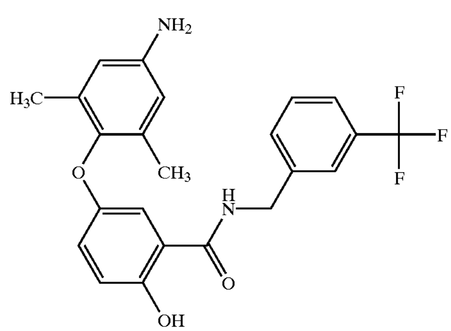 | 430.4 | 3.87 | 430.2 |
| 249 | 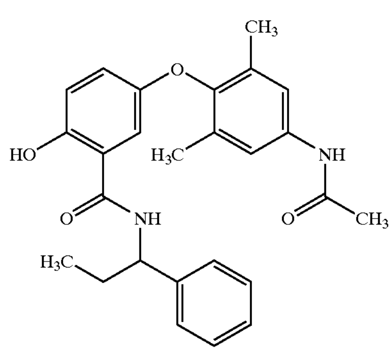 | 432.5 | 4.40 | 432.2 |

| Ex. No. | Structure | MW [g/mol] calculated | Retention time [min] | MW [g/mol] found |
|---|---|---|---|---|
| 250 | 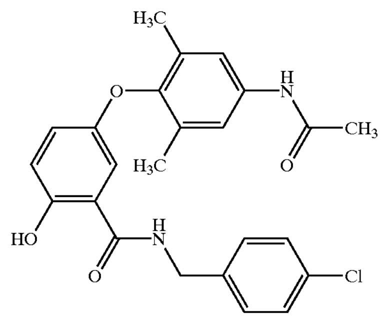 | 438.9 | 4.43 | 438.1 |
| 251 | 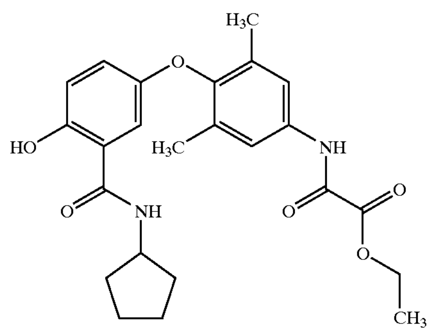 | 440.5 | 4.60 | 440.2 |
| 252 | 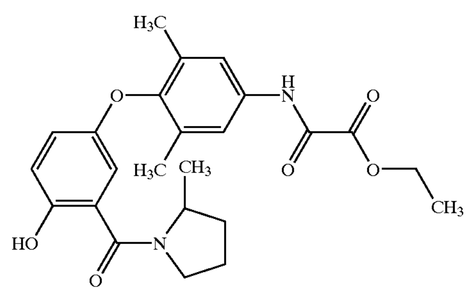 | 440.5 | 3.96 | 440.2 |
| 253 | 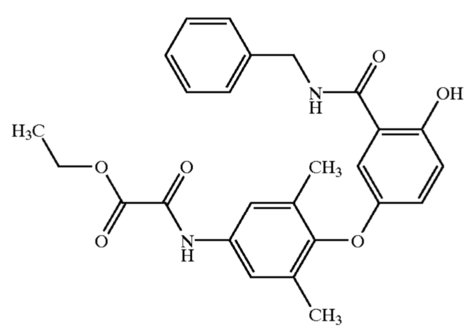 | 462.5 | 4.59 | 462.2 |

-continued

| Ex. No. | Structure | MW [g/mol] calculated | Retention time [min] | MW [g/mol] found |
|---|---|---|---|---|
| 254 | 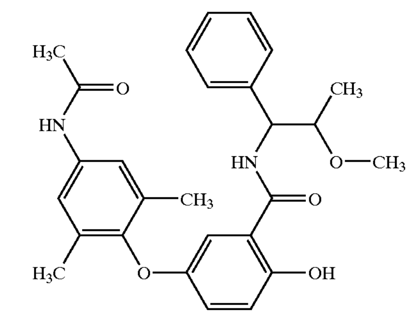 | 462.6 | 4.24 | 462.2 |
| 255 | 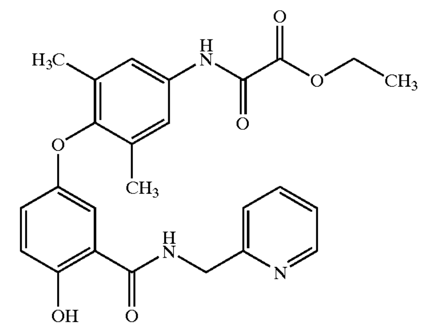 | 463.5 | 3.39 | 463.2 |
| 256 | 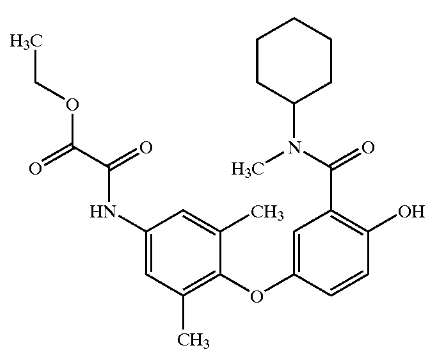 | 468.6 | 4.99 | 468.2 |
| 257 | 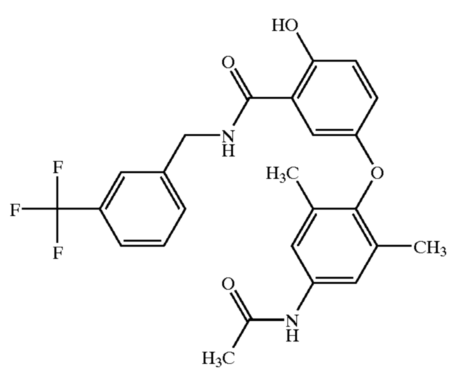 | 472.5 | 4.50 | 472.2 |

-continued

| Ex. No. | Structure | MW [g/mol] calculated | Retention time [min] | MW [g/mol] found |
|---|---|---|---|---|
| 258 | 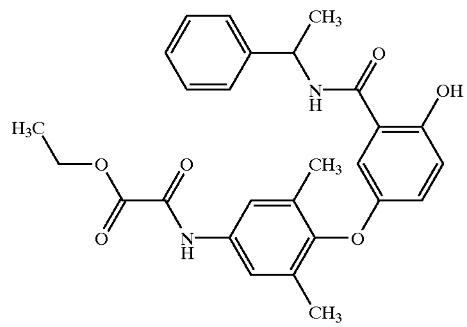 | 476.5 | 4.65 | 476.2 |
| 259 | 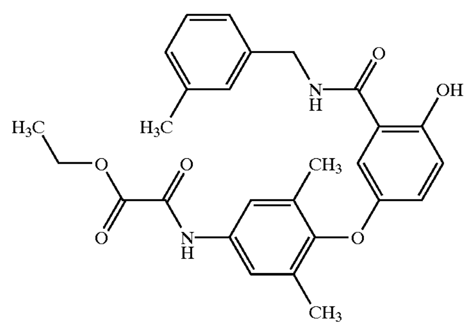 | 476.5 | 4.74 | 476.2 |
| 260 | 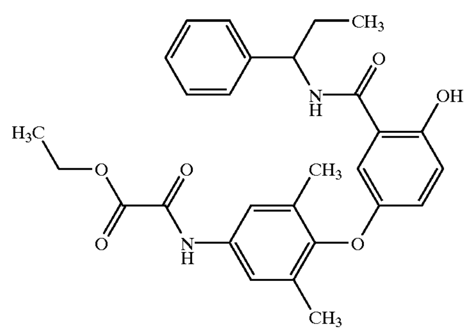 | 490.6 | 4.78 | 490.2 |
| 261 | 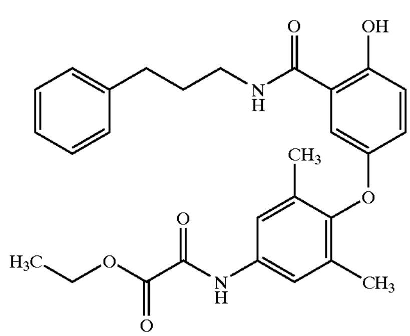 | 490.6 | 4.84 | 490.2 |

| Ex. No. | Structure | MW [g/mol] calculated | Retention time [min] | MW [g/mol] found |
|---|---|---|---|---|
| 262 | 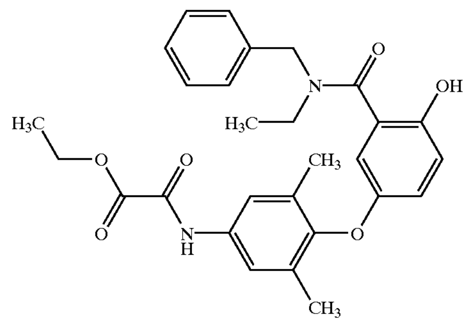 | 490.6 | 4.23 | 490.2 |
| 263 | 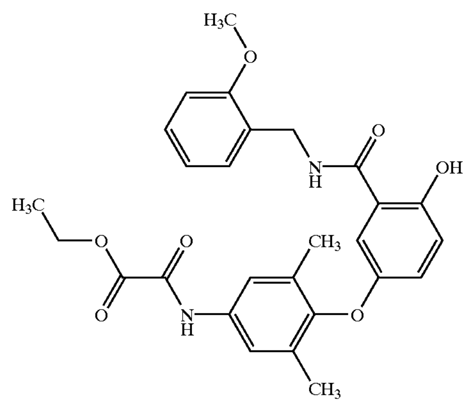 | 492.5 | 4.59 | 492.2 |
| 264 | 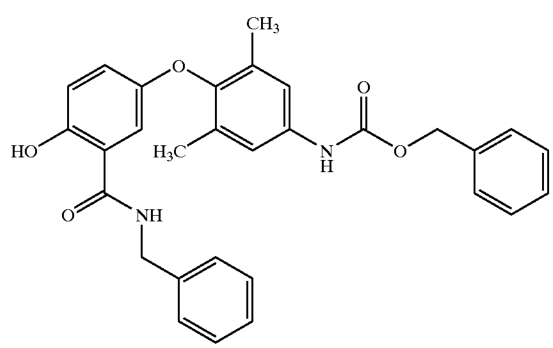 | 496.6 | 5.04 | 496.2 |
| 265 | 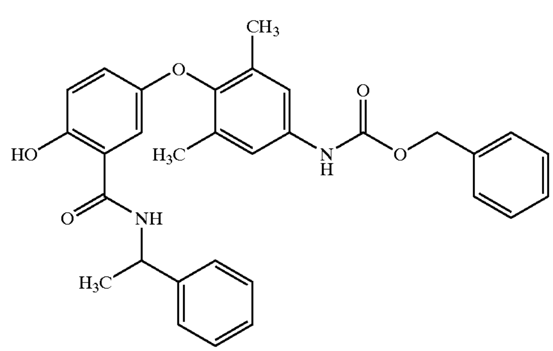 | 510.6 | 5.09 | 510.2 |

-continued

| Ex. No. | Structure | MW [g/mol] calculated | Retention time [min] | MW [g/mol] found |
|---|---|---|---|---|
| 266 | 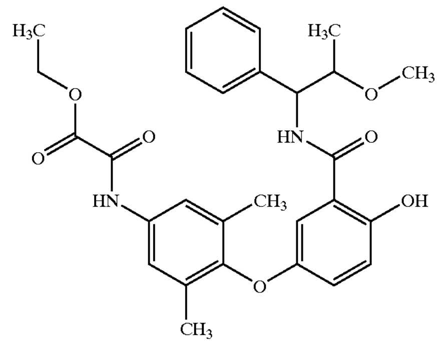 | 520.6 | 4.63 | 520.2 |
| 267 | 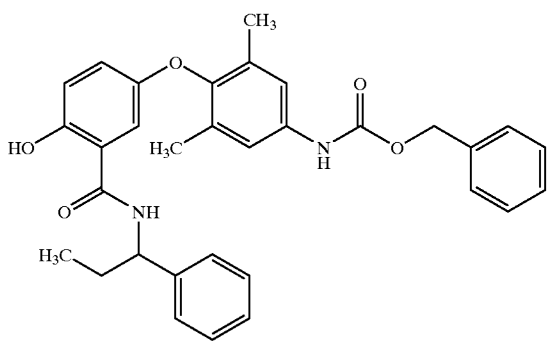 | 524.6 | 5.20 | 524.2 |
| 268 | 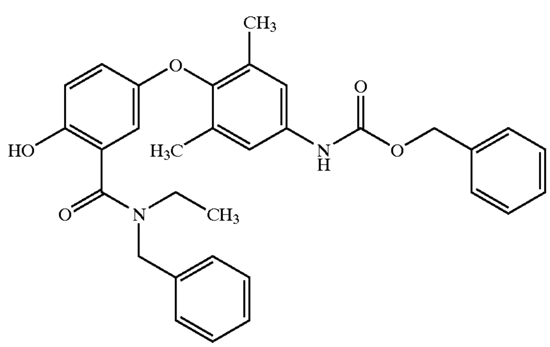 | 524.6 | 4.75 | 524.2 |
| 269 | 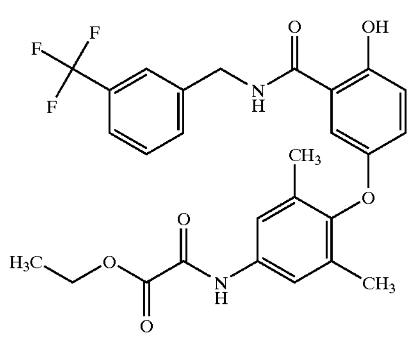 | 530.5 | 4.85 | 530.2 |

-continued

| Ex. No. | Structure | MW [g/mol] calculated | Retention time [min] | MW [g/mol] found |
|---|---|---|---|---|
| 270 | 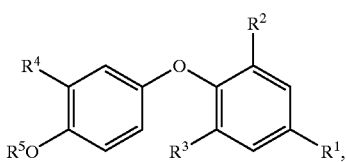 | 564.6 | 5.24 | 564.2 |

What is claimed is:

1. Compounds of the general formula (I)

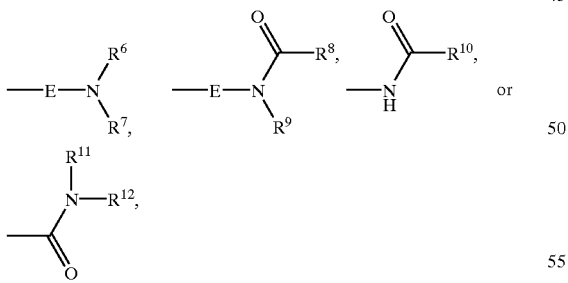

in which

R$^1$ represents nitro, amino, acetamido or represents a group of the formula —NH—CO—CO—A or —NH—CH$_2$—CO—A, in which A represents hydroxyl or (C$_1$–C$_4$)-alkoxy, R$^2$ and R$^3$ are identical or different and denote halogen, C$_1$–C$_4$-alkyl or trifluoromethyl, R$^4$ represents a group of the formula —E—N(R$^6$)(R$^7$),  —E—N(R$^9$)—C(O)—R$^8$,  —NH—C(O)—R$^{10}$, or

N(R$^{11}$)(R$^{12}$)—C(O)— in which

E represents straight-chain or branched (C$_1$–C$_4$)-alkyl,

R$^6$ and R$^7$ are identical or different and, independently of one another, represent straight-chain or branched (C$_1$–C$_{10}$)-alkyl which can be substituted one or more times, identically or differently, by (C$_3$–C$_8$)-cycloalkyl, (C$_1$–C$_6$)-alkoxy, amino, mono- or di-(C$_1$–C$_6$)-alkylamino, (C$_1$–C$_4$-alkoxycarbonylamino, aminocarbonyl, (C$_1$–C$_6$)-alkoxycarbonyl, or by (C$_6$–C$_{10}$)-aryl, where aryl is optionally substituted one or more times, identically or differently, by (C$_1$–C$_4$)-alkyl, aminocarbonyl, (C$_1$–C$_4$)-alkanoylamino or halogen, or represent (C$_6$–C$_{10}$)-aryl or (C$_3$–C$_8$)-cycloalkyl, each of which can be substituted by (C$_1$–C$_4$)-alkoxy, R$^8$ represents straight-chain or branched (C$_1$–C$_{10}$)-alkyl which can be substituted by (C$_3$–C$_8$)-cycloalkyl, phenyl or phenoxy, or represents (C$_3$–C$_8$)-cycloalkyl, (C$_6$–C$_{10}$)-aryl, biphenylyl or (C$_1$–C$_6$)-alkoxy, R$^9$ represents straight-chain or branched (C$_1$–C$_8$)-alkyl whose carbon chain can be interrupted by —O— and which can be substituted by (C$_3$–C$_8$)-cycloalkyl or phenyl, or represents (C$_3$–C$_8$)-cycloalkyl, (C$_2$–C$_6$)-alkenyl, or phenyl, where the aromatic ring systems mentioned both in R$^8$ and in can, in each case independently of one another, in turn be substituted by trifluoromethyl, halogen, (C$_1$–C$_4$)-alkoxy, (C$_1$–C$_4$)-alkyl or amino, R$^{10}$ represents straight-chain or branched (C$_1$–C$_{15}$)-alkyl which can be substituted by (C$_3$-C$_g$)-cycloalkyl, (C$_1$–C$_4$)-alkoxy, phenyl, phenoxy or benzyloxy, where the said aromatic radicals can in turn each be substituted up to three times, identically or differently, by halogen, (C$_1$–C$_6$)-alkyl or (C$_1$–C$_4$)-alkoxy, represents (C$_3$–C$_8$)-cycloalkyl which can be substituted by (C$_1$–C$_4$)-alkoxy or phenyl, represents (C$_6$–C$_{10}$)-aryl which can be substituted up to three times, identically or differently, by (C$_1$–C$_6$)-alkyl, (C$_1$–C$_6$)-alkoxy, halogen, cyano, amino, trifluoromethyl or phenyl, or denotes a group of the formula —OR$^{13}$ or NR$^{14}$R$^{15}$, in which R$^{13}$ represents straight-chain or branched (C$_1$–C$_6$)-alkyl, and R$^{14}$ and R$^{15}$ are identical or different and, independently of one another, represent hydrogen, straight-chain or branched (C$_1$–C$_{12}$)-alkyl, which can be substituted by aminocarbonyl, a group of the formula —NR$^{16}$R$^{17}$, or can be substituted by phenyl, where phenyl is optionally substituted up to twice, identically or differently, by halogen, $(C_1-C_4)$-alkyl, trifluoromethyl or $(C_1-C_4)$-alkoxy,
represent $(C_3-C_8)$-cycloalkyl which can be substituted by $(C_1-C_4)$-alkyl, or
represent $(C_6-C_{10})$-aryl which can be substituted up to three times, identically or differently, by halogen, $(C_1-C_4)$-alkyl, trifluoromethyl, $(C_1-C_4)$-alkoxy, amino, phenyl or phenoxy, where
$R^{16}$ and $R^{17}$ are identical or different and, independently of one another, represent hydrogen, $(C_1-C_6)$-alkyl, phenyl or arylsulphonyl,
$R^{11}$ and $R^{12}$ are identical or different and, independently of one another,
represent hydrogen, straight-chain or branched $(C_1-C_6)$-alkyl, which can be substituted one or more times, identically or differently, by mono-$(C_1-)$-alkylamino, di-$(C_1-C_6)$-alkylamino, $(C_1-C_4)$-alkoxy, $(C_{1-6})$-alkoxycarbonyl, carboxyl, or $(C_6-C_{10})$-aryl, where the latter in turn is optionally substituted by halogen, trifluoromethyl, $(C_1-C_6)$-alkyl or $(C_1-C_6)$-alkoxy,
represent $(C_3-C_8)$-cycloalkyl where cycloalkyl is optionally substituted by $(C_1-C_4)$-alkyl,
$R^5$ denotes hydrogen, $(C_1-C_4)$-alkyl or $(C_1-C_4)$-alkanoyl, and the respective salts and hydrates thereof.

2. Compounds of the general formula (I) according to claim 1, in which

E represents straight-chain or branched $(C_1-C_4)$-alkyl, $R^1$ represents acetamido or represents a group of the formula —NI—I—CO—CO—A or —NH—CH$_2$—CO—A,
in which
A represents hydroxyl or $(C_1-C_4)$-alkoxy, $R^2$ and $R^3$ are identical or different and denote halogen, methyl or trifluoromethyl, $R^4$ represents a group of the formula

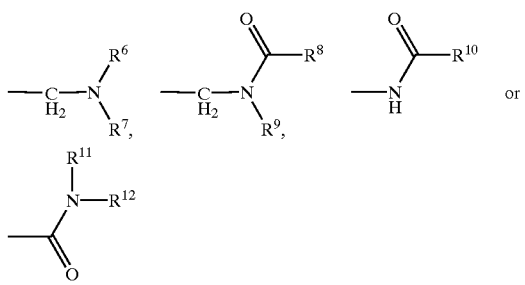

in which
$R^6$ and $R^7$ are identical or different and, independently of one another, represent straight-chain or branched $(C_1-C_{10})$-alkyl which can be substituted one or more times, identically or differently, by $(C_3-C_8)$-cycloalkyl, $(C_1-C_4)$-alkoxy, or by $(C_6-C_{10})$-aryl which in turn is optionally substituted one or more times, identically or differently, by aminocarbonyl, $(C_1-C_4)$-alkanoylamino or halogen, or
represent $(C_3-C_8)$-cycloalkyl which can be substituted by $(C_1-C_4)$-alkoxy, $R^8$ represents straight-chain or branched $(C_1-C_8)$-alkyl, $(C_3-C_8)$-cycloalkyl, $(C_3-C_6)$-cycloalkyliethyl or phenyl, $R^9$ represents straight-chain or branched $(C_1-C_8)$-alkyl whose carbon chain can be interrupted by —O— and which can be substituted by phenyl, or $(C_3-C_8)$-cycloalkyl or phenyl which can be substituted by halogen, trifluoromethyl or $(C_1-C_4)$-alkyl, $R^{10}$ represents straight-chain or branched $(C_1-C_{10})$-alkyl which can be substituted by $(C_3-C_8)$-cycloalkyl, $(C_1-C_4)$-alkoxy, phenyl or phenoxy, where the said aromatic radicals can in turn each be substituted up to three times, identically or differently, by halogen, $(C_1-C_3)$-alkyl or $(C_1-C_4)$-alkoxy,
represents $(C_3-C_8)$-cycloalkyl or represents phenyl which can be substituted up to three times, identically or differently, by $(C_1-C_4)$-alkyl, $(C_1-C_4)$-alkoxy, halogen or phenyl, or
denotes a group of the formula —OR$^{13}$ or —NR$^{14}$R$^{15}$,
in which
$R^{13}$ represents straight-chain or branched $(C_1-C_6)$-alkyl, and
$R^{14}$ and $R^{15}$ are identical or different and, independently of one another,
represent hydrogen or straight-chain or branched $(C_1-C_6)$-alkyl which can be substituted by phenyl which in turn is optionally substituted up to twice, identically or differently, by halogen, $(C_1-C_4)$-alkyl, trifluoromethyl or $(C_1-C_4)$-alkoxy,
represent $(C_3-C_8)$-cycloalkyl which can be substituted by $(C_1-C_4)$-alkyl, or
represent phenyl, naphthyl or biphenylyl, $R^{11}$ and $R^{12}$ are identical or different and, independently of one another,
represent hydrogen or straight-chain or branched $(C_1-C_6)$-alkyl which can be substituted by phenyl which in turn is optionally substituted by halogen, trifluoromethyl, $(C_1-C_4)$-alkyl or $(C_1-C_4)$-alkoxy, or
represent $(C_3-C_8)$-cycloalkyl which can be substituted by $(C_1-C_4)$-alkyl, $R^5$ denotes hydrogen or $(C_1-C_4)$-alkanoyl, and the respective salts and hydrates thereof.

3. Compounds of the general formula (I) according to claim 1, in which

E represents straight-chain or branched $(C_1-C_4)$-alkyl, $R^1$ represents a group of the formula —NH—CO—COOH or —NH—CH$_2$—COOH, $R^2$ and $R^3$ are identical or different and denote chlorine, bromine, methyl or trifluoromethyl, $R^4$ represents a group of the formula

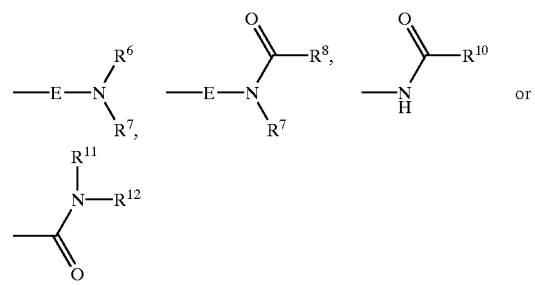

in which
$R^6$ and $R^7$ are identical or different and, independently of one another
represent a straight-chain or branched $(C_1-C_8)$-alkyl which can be substituted by $(C_5-C_8)$-cycloalkyl, or one to three times by methoxy or ethoxy, or which is substituted by phenyl which in turn is optionally substituted once to twice, identically or differently, by fluorine, chlorine, aminocarbonyl or acetamido, or represent $(C_3-C_8)$-cycloalkyl which can be substituted by methoxy or ethoxy, $R^8$ represents straight-chain $(C_1-C_7)$-alkyl, $(C_3-C_6)$-cycloalkyl-methyl, $(C_3-C_6)$-cycloalkyl or phenyl, $R^9$ denotes straight-chain or branched $(C_1-C_4)$-alkyl which can be substituted by phenyl, or $(C_3-C_6)$-cycloalkyl or phenyl which can be substituted by chlorine or fluorine, $R^{10}$ represents straight-chain or branched $(C_1-C_4)$-alkyl which can be substituted by $(C_3-C_6)$-cycloalkyl, phenyl or phenoxy, where the said aromatic radicals can in turn each be substituted up to three times, identically or differently, by fluorine, chlorine or $(C_1-C_3)$-alkyl, or represents biphenylyl, or represents a group of the formula —$NR^{14}R^{15}$, in which $R^{14}$ denotes hydrogen or straight-chain or branched $(C_1-C_3)$-alkyl, and $R^{15}$ represents straight-chain or branched $(C_1-C_4)$-alkyl which can be substituted by phenyl which in turn is optionally substituted by methyl, methoxy, trifluoromethyl, fluorine or chlorine, or represents naphthyl, biphenylyl or $(C_3-C_6)$-cycloalkyl, $R^{11}$ denotes hydrogen or straight-chain or branched $(C_1-C_3)$-alkyl, and $R^{12}$ represents straight-chain or branched $(C_1-C_4)$-alkyl which can be substituted by phenyl which in turn is optionally substituted by methyl, methoxy, trifluoromethyl, fluorine or chlorine, or represents cyclopentyl or cyclohexyl, each of which can be substituted by $(C_1-C_3)$-alkyl, $R^5$ denotes hydrogen or $(C_1-C_4)$-alkyl, and the respective salts and hydrates thereof.

4. Compounds of the general formula (I) according to claim 1, in which $R^1$ represents a group of the formula —NH—CO—COOH or —NH—CH$_2$—COOH, $R^2$ and $R^3$ are identical or different and denote chlorine, bromine, methyl or trifluoromethyl, $R^4$ represents a group of the formula

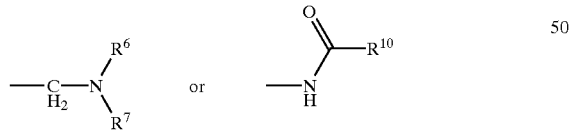

in which $R^6$ and $R^7$ are identical or different and, independently of one another, represent straight-chain or branched $(C_1-C_8)$-alkyl which can be substituted by phenyl which in turn is optionally substituted once to twice, identically or differently, by fluorine, chlorine, aminocarbonyl or acetamido, or can be substituted by $(C_5-C_8)$-cycloalkyl, or once to three times by methoxy or ethoxy, or represent $(C_5-C_8)$-cycloalkyl which can be substituted by methoxy or ethoxy, $R^{10}$ represents straight-chain or branched $(C_1-C_4)$-alkyl which can be substituted by $(C_3-C_6)$-cycloalkyl, phenyl or phenoxy, where the said aromatic radicals can in turn each be substituted up to three times, identically or differently, by fluorine, chlorine or $(C_1-C_3)$-alkyl, or represents biphenylyl, $R^5$ denotes hydrogen, and the respective salts and hydrates thereof.

5. Process for preparing compounds of the general formula (I) according to claim 1, characterized in that (A) compounds of the formula (II)

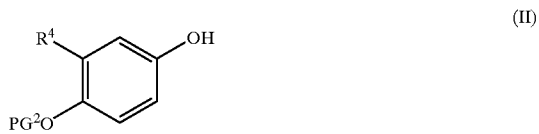

(II)

in which pG$^2$ denotes a hydroxyl protective group or a resin suitable for solid-phase synthesis, and $R^4$ has the meaning indicated in claim 1, are reacted in the presence of a base with compounds of the general formula (III)

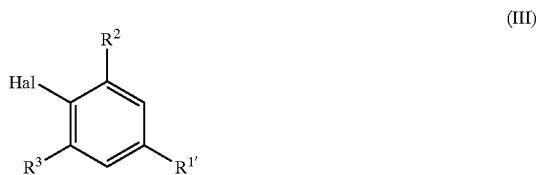

(III)

in which $R^2$ and $R^3$ have the meaning indicated in claim 1, and $R^{1'}$ represents a suitable group from the scope of meanings of $R^1$, preferably represents the NO$_2$ group, and Hal represents chlorine or fluorine, to give compounds of the formula (IV)

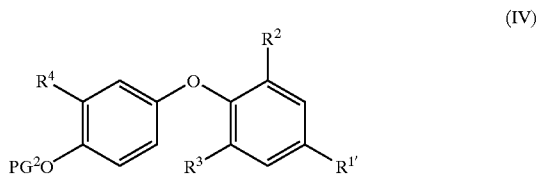

(IV)

in which $R^{1'}$, $R^2$, $R^3$, $R^4$ and PG$^2$ have the meaning indicated above, or (B) compounds of the formula (V)

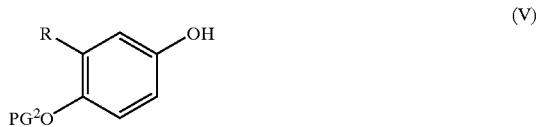

(V)

in which

PG$^2$ has the meaning indicated above, and

R represents a suitable precursor of the $R^4$ group, preferably represents CHO, $(C_1-C_6)$-alkoxycarbonyl or nitro, are reacted in the presence of a base with a compound of the formula (III)

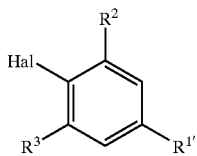
(III)

in which
$R^{1'}, R^2$, Hal and $R^3$ have the meaning indicated above, to give a compound of the formula (VI)

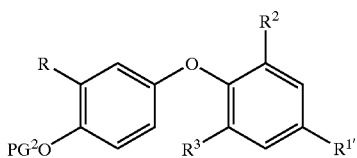
(VI)

in which
R, $R^{1'}, R^2, R^3$ and $PG^2$ have the meaning given above, and the latter is converted into compounds of the formula (IV) by converting the substituent R in a suitable manner to the substituent $R^4$, and in that finally the protective group $PG^2$ is eliminated from the compound of the formula (IV) and, where appropriate, the substituents are modified or derivatized in a suitable way by standard reactions.

6. Pharmaceutical containing at least one compound of the general formula (I) according to claim 1 and a pharmaceutically acceptable carrier.

7. A method of treating arteriosclerosis and/or hypercholesterolaemia, comprising administering to a mammal an effective amount of a compound according claim 1.

8. A method of treating pathological states which can be treated with natural thyroid hormone, comprising administering to a mammal an effective amount of a compound according to claim 1.

* * * * *